United States Patent
Roh et al.

(10) Patent No.: US 11,969,272 B2
(45) Date of Patent: Apr. 30, 2024

(54) COMPUTED TOMOGRAPHY APPARATUS AND METHOD USING PLURALITY OF LIGHT SOURCES

(71) Applicant: KOH YOUNG TECHNOLOGY INC., Seoul (KR)

(72) Inventors: Young Jun Roh, Suwon-si (KR); Min Sik Shin, Yongin-si (KR); Sung Hoon Kang, Suwon-si (KR); Tae Seok Oh, Yongin-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 257 days.

(21) Appl. No.: 17/623,127

(22) PCT Filed: Jun. 26, 2020

(86) PCT No.: PCT/KR2020/008416
§ 371 (c)(1),
(2) Date: Dec. 27, 2021

(87) PCT Pub. No.: WO2020/263044
PCT Pub. Date: Dec. 30, 2020

(65) Prior Publication Data
US 2022/0265227 A1   Aug. 25, 2022

Related U.S. Application Data

(60) Provisional application No. 62/866,967, filed on Jun. 26, 2019.

(51) Int. Cl.
*A61B 6/03*   (2006.01)
*A61B 6/00*   (2006.01)
(Continued)

(52) U.S. Cl.
CPC .............. *A61B 6/035* (2013.01); *A61B 6/027* (2013.01); *A61B 6/0407* (2013.01);
(Continued)

(58) Field of Classification Search
CPC ....... A61B 6/035; A61B 6/027; A61B 6/0407; A61B 6/0487; A61B 6/4007;
(Continued)

(56) References Cited

U.S. PATENT DOCUMENTS 4,196,352 A   4/1980   Berninger et al.
4,384,359 A   5/1983   Franke
(Continued)

FOREIGN PATENT DOCUMENTS

GB   2 022 356   12/1979
JP   S54-152489   11/1979
(Continued)

OTHER PUBLICATIONS

Japanese Office Action with English translation for Japanese Patent Application or Patent No. 2021-577670, dated Sep. 27, 2022.
(Continued)

*Primary Examiner* — David P Porta
*Assistant Examiner* — Mamadou Faye
(74) *Attorney, Agent, or Firm* — KILE PARK REED & HOUTTEMAN PLLC

(57) ABSTRACT

A computed tomography (CT) apparatus according to various embodiments may include a gantry including a first rotation device, a second rotation device and a third rotation device which have a ring shape, share an axis of rotation, and are rotatable independently of one another, a plurality of first light sources provided on the first rotation device at regular intervals and configured to emit X-rays to a subject, a plurality of second light sources provided on the second rotation device at regular intervals and configured to emit
(Continued)

X-rays to the subject, a detector provided on a region of the third rotation device and configured to detect X-rays passing through the subject, and one or more processors.

20 Claims, 41 Drawing Sheets

(51) Int. Cl.
*A61B 6/02* (2006.01)
*A61B 6/04* (2006.01)
*A61B 6/40* (2024.01)
*A61B 6/42* (2024.01)

(52) U.S. Cl.
CPC .......... *A61B 6/0487* (2020.08); *A61B 6/4007* (2013.01); *A61B 6/4014* (2013.01); *A61B 6/4275* (2013.01); *A61B 6/4435* (2013.01); *A61B 6/4447* (2013.01); *A61B 6/4452* (2013.01); *A61B 6/5205* (2013.01)

(58) Field of Classification Search
CPC ... A61B 6/4014; A61B 6/4435; A61B 6/4447; A61B 6/5205; A61B 6/56; A61B 6/4275; A61B 6/4429; A61B 6/4452; A61B 6/4021
See application file for complete search history.

(56) References Cited

U.S. PATENT DOCUMENTS

| | | | |
|---|---|---|---|
| 4,817,119 | A | 3/1989 | Ledley et al. |
| 5,966,422 | A * | 10/1999 | Dafni .................. A61B 6/482 378/15 |
| 2004/0013239 | A1 | 1/2004 | Gregerson et al. |
| 2005/0100124 | A1 | 5/2005 | Hsieh et al. |
| 2005/0111623 | A1 | 5/2005 | Bruder et al. |
| 2007/0238957 | A1 | 10/2007 | Yared |
| 2008/0043912 | A1 | 2/2008 | Harding |
| 2008/0101537 | A1 | 5/2008 | Sendai |
| 2011/0268246 | A1 | 11/2011 | Dafni |
| 2014/0023178 | A1 | 1/2014 | Kim et al. |
| 2015/0230766 | A1 | 8/2015 | Wang et al. |
| 2015/0312998 | A1 | 10/2015 | Tamura et al. |
| 2015/0366522 | A1 | 12/2015 | Besson |
| 2016/0213336 | A1 | 7/2016 | Kim et al. |
| 2016/0235382 | A1 | 8/2016 | Besson |
| 2016/0310086 | A1 | 10/2016 | Besson |
| 2017/0172526 | A1 | 6/2017 | Chiang |
| 2017/0249759 | A1 | 8/2017 | Hsieh et al. |
| 2017/0303868 | A1 | 10/2017 | Lee et al. |
| 2019/0209868 | A1 * | 7/2019 | Stahl ................. A61N 5/1039 |

FOREIGN PATENT DOCUMENTS

| | | |
|---|---|---|
| JP | S55-42663 | 3/1980 |
| JP | S56-97440 | 8/1981 |
| JP | 62-167538 | 7/1987 |
| JP | S62-249639 | 10/1987 |
| JP | H5-7583 | 1/1993 |
| JP | 2005-152638 | 6/2005 |
| JP | 2008-104673 | 5/2008 |
| JP | 2009-160270 | 7/2009 |
| KR | 10-2010-0055972 | 5/2010 |
| KR | 10-2014-0013403 | 2/2014 |
| KR | 10-2015-0024736 | 3/2015 |
| KR | 10-2016-0027574 | 3/2016 |
| KR | 10-2016-0057935 | 5/2016 |
| WO | 2014/047518 | 3/2014 |
| WO | 2015/030472 | 3/2015 |
| WO | 2016/076525 | 5/2016 |
| WO | 2017/165835 | 9/2017 |
| WO | 2018/115025 | 6/2018 |

OTHER PUBLICATIONS

Japanese Office Action with English translation for Japanese Patent Application or Patent No. 2021-577664, dated Sep. 27, 2022.
Japanese Office Action with English translation for Japanese Patent Application or Patent No. 2021-577632, dated Sep. 27, 2022.
Extended European Search Report for European Patent Application or Patent No. 20830804.9 dated Jul. 12, 2022.
Extended European Search Report for European Patent Application or Patent No. 20832899.7, dated Jul. 11, 2022.
Extended European Search Report for European Patent Application or Patent No. 20831813.9, dated Jul. 21, 2022.
International Search Report, with English translation, corresponding to International Application No. PCT/KR2020/008411, dated Sep. 28, 2020.
Written Opinion, with English translation, corresponding to International Application No. PCT/KR2020/008411, dated Sep. 28, 2020.
International Search Report, with English translation, for International Application No. PCT/KR2020/008416, dated Oct. 8, 2020.
Written Opinion, with English translation, for International Application No. PCT/KR2020/008416, dated Oct. 8, 2020.
International Search Report, with English translation, corresponding to International Application No. PCT/KR2020/008414, dated Sep. 28, 2020.
Written Opinion, with English translation, corresponding to International Application No. PCT/KR2020/008414, dated Sep. 28, 2020.
Japanese Office Action with English translation for Japanese Patent Application No. 2021-577664 dated Feb. 14, 2023.
Korean Office Action with English translation for Korean Patent Application No. 10-2021-7042631, dated Jun. 16, 2023.
Korean Office Action with English translation for Korean Patent Application No. 10-2021-7042637, dated Jun. 19, 2023.
Korean Office Action with English translation for Korean Patent Application No. 10-2021-7042641, dated Jun. 20, 2023.
Japanese Office Action with English translation for Japanese Patent Application or Patent No. 2023-042222, dated Dec. 12, 2023.
U.S. Office Action for U.S. Appl. No. 17/623,131, dated Dec. 21, 2023.
U.S. Office Action for U.S. Appl. No. 17/623,115, dated Dec. 21, 2023.

* cited by examiner

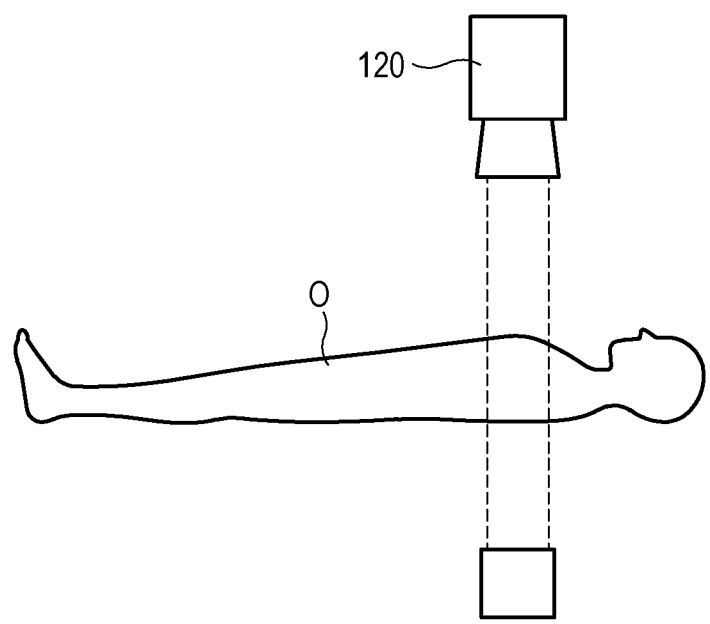

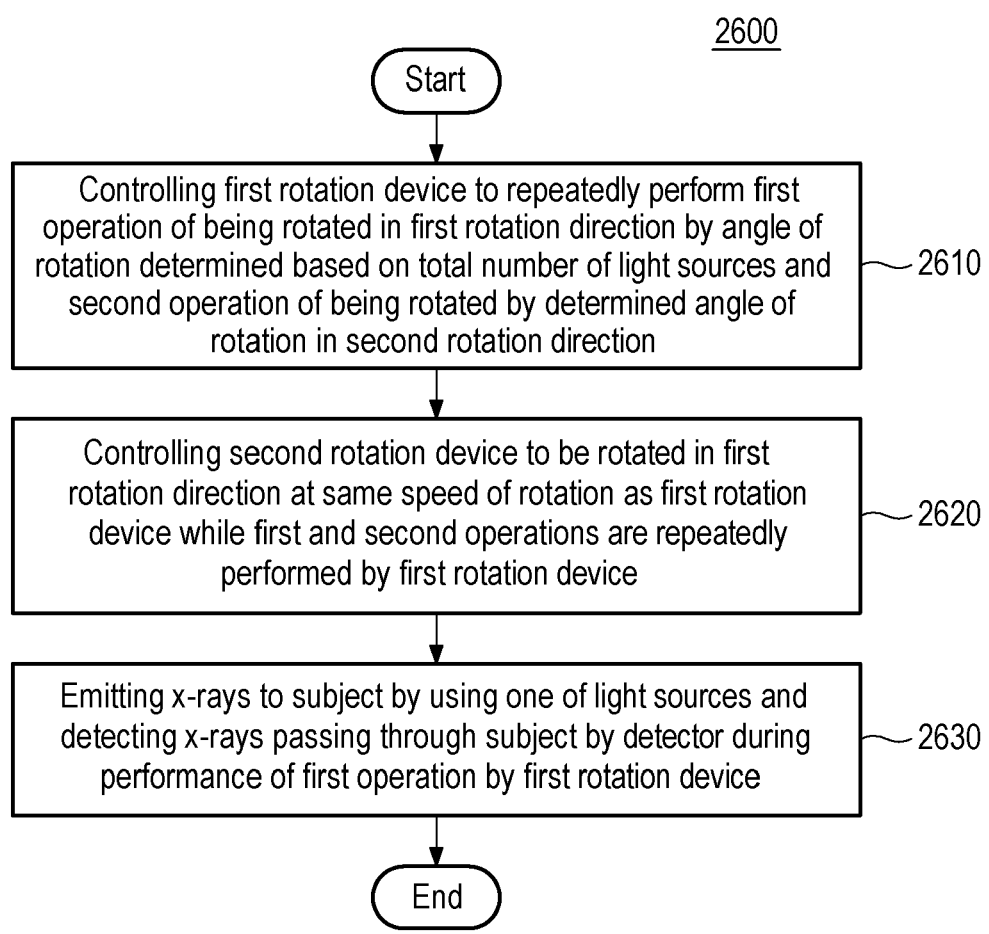

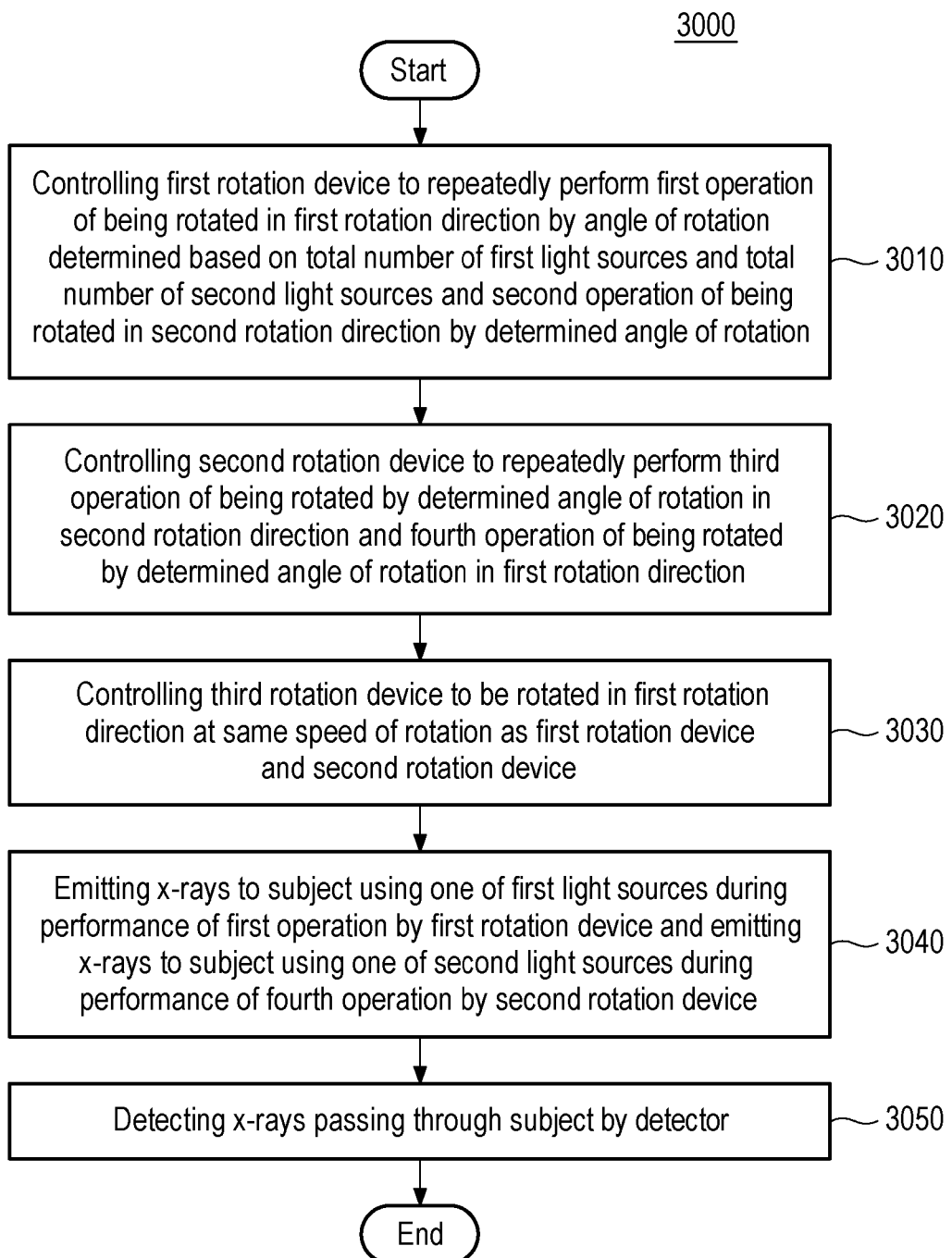

COMPUTED TOMOGRAPHY APPARATUS AND METHOD USING PLURALITY OF LIGHT SOURCES

TECHNICAL FIELD

The present disclosure relates to a computed tomography (CT) apparatus and method using a plurality of light sources.

BACKGROUND

Computed tomography (CT) is a non-invasive biometric imaging method. A CT apparatus is capable of obtaining a CT image of a subject by emitting X-rays to the subject in various directions, detecting some X-rays passing through the subject by a detector, converting output data of the detector into an electric signal, and reconstructing an image. In general, a CT apparatus is capable of obtaining a three-dimensional (3D) image of a subject by placing the subject in a ring-shaped gantry in which X-ray sources are arranged, emitting X-rays to the subject during rotation of the gantry to obtain images of cross sections of the subject, and reconstructing the images of the cross sections of the subject.

SUMMARY

A computed tomography (CT) apparatus using one light source (e.g., an X-ray source) emits X-rays to a subject while rotating around the subject by 360 degrees to obtain a CT image of the subject. When an angle of rotation of the gantry in which the light source is disposed increases, lines (e.g., lines for supplying power to the light source) connected to the gantry may be twisted.

Because high power is needed to emit X-rays from a light source, a CT apparatus using a plurality of light sources may not be capable of operating the plurality of light sources simultaneously. In this case, a CT image of a subject may be obtained by appropriately setting an arrangement of the plurality of light sources and an order of emitting X-rays.

A computed tomography (CT) apparatus according to various embodiments of the present disclosure may include: a gantry including a first rotation device, a second rotation device and a third rotation device which have a ring shape, share an axis of rotation, and are rotatable independently of one another; a plurality of first light sources provided on the first rotation device at regular intervals and configured to emit X-rays to a subject; a plurality of second light sources provided on the second rotation device at regular intervals and configured to emit X-rays to the subject; a detector provided on a region of the third rotation device and configured to detect X-rays passing through the subject; and one or more processors. The one or more processors may be configured to control the first rotation device to repeatedly perform a first operation of being rotated in a first rotation direction by an angle of rotation determined based on a total number of the plurality of first light sources and a total number of the plurality of second light sources and a second operation of being rotated by the determined angle of rotation in a second rotation direction opposite to the first rotation direction, control the second rotation device to repeatedly perform a third operation of being rotated by the determined angle of rotation in the second rotation direction and a fourth operation of being rotated by the determined angle of rotation in the first rotation direction, control the third rotation device to be rotated in the first rotation direction at the same speed of rotation as the first rotation device and the second rotation device while the first rotation device repeatedly performs the first operation and the second operation and the second rotation device repeatedly performs the third operation and the fourth operation, emit X-rays to the subject from one of the plurality of first light sources during the performance of the first operation by the first rotation device and emit X-rays to the subject from one of the plurality of second light sources during the performance of the fourth operation by the second rotation device, and detect X-rays passing through the subject by the detector.

A CT method according to various embodiments of the present disclosure, which is performed by a CT apparatus including a gantry with a first rotation device, a second rotation device, and a third rotation device that have a ring shape, share an axis of rotation, and are rotatable independently of one another, a plurality of first light sources arranged on the first rotation device at regular intervals and configured to emit X-rays to a subject, a plurality of second light sources arranged on the second rotation device at regular intervals and configured to emit X-rays to the subject, and a detector provided on a region of the third rotation device and configured to detect X-rays passing through subject, includes controlling the first rotation device to repeatedly perform a first operation of being rotated in a first rotation direction by an angle of rotation determined based on a total number of the plurality of first light sources and a total number of the plurality of second light sources and a second operation of being rotated by the determined angle of rotation in a second rotation direction opposite to the first rotation direction, controlling the second rotation device to repeatedly perform a third operation of being rotated by the determined angle of rotation in the second rotation direction and a fourth operation of being rotated by the determined angle of rotation in the first rotation direction, controlling the third rotation device to be rotated in the first rotation direction at the same speed of rotation as the first rotation device and the second rotation device, emitting X-rays to the subject from one of the plurality of first light sources during the performance of the first operation by the first rotation device and emitting X-rays to the subject from one of the plurality of second light sources during the performance of the fourth operation by the second rotation device, and detecting X-rays passing through the subject by the detector.

BRIEF DESCRIPTION OF DRAWINGS

FIGS. 3A and 3B are diagrams illustrating a method of obtaining a circular CT image of a subject according to various embodiments of the present disclosure.

FIG. 26 is a flowchart of operations of the CT apparatus according to the fifth embodiment.

FIG. 30 is a flowchart of operations of the CT apparatus according to the sixth embodiment.

DETAILED DESCRIPTION

Figure 1:
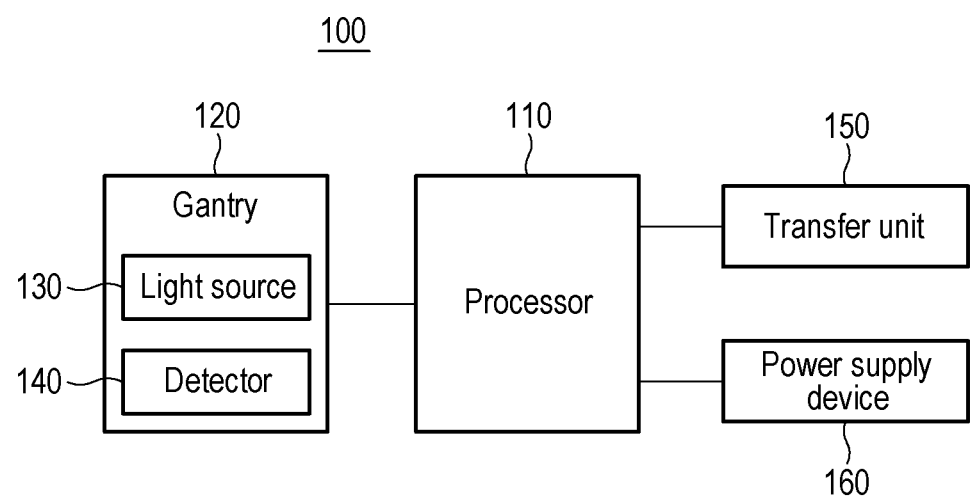
FIG. 1 is a block diagram of a computed tomography (CT) apparatus according to various embodiments of the present disclosure.

Embodiments of the present disclosure are illustrated for describing the technical spirit of the present disclosure. The scope of the claims according to the present disclosure is not limited to the embodiments described below or to the detailed descriptions of these embodiments.

All technical or scientific terms used herein have meanings that are generally understood by a person having ordinary knowledge in the art to which the present disclosure pertains, unless otherwise specified. The terms used herein are selected only for more clear illustration of the present disclosure and are not intended to limit the scope of claims in accordance with the present disclosure.

The expressions "include," "provided with," "have," and the like used herein should be understood as open-ended terms including the possibility of inclusion of other embodiments, unless otherwise mentioned in a phrase or sentence including the expressions.

A singular expression may include the plural meaning, unless otherwise mentioned, and the same is applicable to a singular expression stated in the claims.

The terms "first," "second," etc. used herein are used to identify a plurality of components from one another and are not intended to limit the order or importance of the relevant components.

The term "unit" used in these embodiments means a software component or hardware component, such as a field-programmable gate array (FPGA) and an application specific integrated circuit (ASIC). However, a "unit" is not limited to software and hardware. A "unit" may be configured to be stored in an addressable storage medium or may be configured to operate one or more processors. For example, a "unit" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "units" may be combined into a smaller number of components and "units" or further subdivided into additional components and "units."

The expression "based on" used herein is used to describe one or more factors that influence a decision, an action of judgment or an operation described in a phrase or sentence including the relevant expression, and this expression does not exclude additional factors influencing the decision, the action of judgment, or the operation.

When a certain component is described as "coupled to" or "connected to" another component, this should be understood as meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, identical or corresponding components are indicated by identical reference numerals. In the following description of embodiments, repeated descriptions of the identical or corresponding components will be omitted. However, even when a description of a component is omitted, such a component is not intended to be excluded from an embodiment.

FIG. 1 is a block diagram of a computed tomography (CT) apparatus 100 according to various embodiments of the present disclosure.

Referring to FIG. 1, the CT apparatus 100 according to various embodiments may include a processor 110 and a gantry 120. The CT apparatus 100 according to various embodiments may further include a transfer unit 150 and a power supply device 160. Even when some of the components shown in FIG. 1 are omitted or replaced with other components, there will be no difficulties in implementing various embodiments set forth herein.

The processor 110 according to various embodiments may be a component that controls the components of the CT apparatus 100 and/or performs an operation for communication or data processing. The processor 110 may be operatively connected to, for example, the components of the CT apparatus 100. The processor 110 may load a command or data received from another component of the CT apparatus 100 to a memory (not shown), process the command or data stored in the memory, and store result data. The CT apparatus 100 according to various embodiments may include one or more processors 110.

The gantry 120 according to various embodiments may be a structure in which a plurality of light sources 130 and a detector 140 are arranged. The gantry 120 may be a ring-shaped (or tunnel type) structure configured to rotate the plurality of light sources 130 and the detector 140 about a certain axis.

The light source 130 according to various embodiments may be an X-ray source for emitting X-rays. The light source 130 may emit X-rays to a subject under control of the processor 110. The subject may be located, for example, in a bore (or an inner hole) of the gantry 120. The CT apparatus 100 according to various embodiments may include a plurality of light sources 130. The plurality of light sources 130 may be, for example, X-ray sources using carbon nanotubes (CNTs).

The detector 140 according to various embodiments may be an X-ray detector 140 for detecting the amount (or intensity) of X-rays. The detector 140 may detect the amount of X-rays passing through a subject among X-rays emitted to the subject from the light source 130. When a density in the subject is not uniform, the amount of X-rays absorbed by the subject may vary according to a direction in which the X-rays are emitted. The detector 140 may measure a reduction rate of the amount of X-rays passing through the subject when the X-rays are emitted at various angles, and the processor 110 may determine a density in the subject based on data measured by the detector 140 and create a three-dimensional (3D) image by reconstructing cross sections of the inside of the subject using the determined density in the subject. The CT apparatus 100 according to various embodiments may include at least one detector 140.

The CT apparatus 100 according to an embodiment may include a gantry 120, a plurality of light sources 130, and a detector 140. The gantry 120 may include a first rotation device and a second rotation device that have a ring shape, share an axis of rotation, and are rotatable independently of each other. The plurality of light sources 130 may be arranged on the first rotation device at regular intervals, and the detector 140 may be arranged on the second rotation device. For example, the plurality of light sources 130 may be arranged on an inner side of the first rotation device at regular intervals to emit X-rays to the subject in the gantry 120. For example, the detector 140 may be configured to surround all of the inner sides of the second rotation device. In this case, even when X-rays are emitted from one of the plurality of light sources 130, the detector 140 may detect X-rays passing through the subject.

The CT apparatus 100 according to an embodiment may include a gantry 120, a plurality of light sources 130, and a plurality of detectors 140. The gantry 120 may include a ring-shaped rotation device rotatable about an axis of rotation. The plurality of light sources 130 may be arranged on the rotation device at regular intervals. Each of the plurality of detectors 140 may be arranged at a position facing and corresponding to one of the plurality of light sources 130. The plurality of light sources 130 may emit X-rays to a subject loaded on the transfer unit 150, and the plurality of detectors 140 may detect X-rays passing through the subject. The plurality of light sources 130 may be located at the same position on an axis of rotation of the rotation device. For example, the plurality of light sources 130 may be located at the same position on a z-axis.

The CT apparatus 100 according to an embodiment may include a gantry 120, a plurality of light sources 130, and a plurality of detectors 140. The gantry 120 may include a ring-shaped rotation device rotatable about an axis of rotation. The plurality of light sources 130 may be arranged on the rotation device at regular intervals. Each of the plurality of detectors 140 may be arranged at a position facing and corresponding to one of the plurality of light sources 130. The plurality of light sources 130 may be arranged at positions on an axis of rotation of the rotation device to be spaced a certain distance from each other. For example, positions of the plurality of light sources 130 on the z-axis may be different from each other.

The CT apparatus 100 according to an embodiment may include a gantry 120, a plurality of light sources 130, and a detector 140. The gantry 120 may include a ring-shaped rotation device rotatable about an axis of rotation. The gantry 120 may be divided into a first sub-device and a second sub-device. The plurality of light sources 130 may be arranged on the first sub-device to be spaced a certain distance from each other. The detector 140 may be arranged on the second sub-device.

The CT apparatus 100 according to an embodiment may include a gantry 120, a plurality of light sources 130, and a detector 140. The gantry 120 may include a first rotation device and a second rotation device that have a ring shape, share an axis of rotation, and are rotatable independently of each other. The plurality of light sources 130 may be arranged on the first rotation device at regular intervals. The detector 140 may be arranged in a region of the second rotation device.

The CT apparatus 100 according to an embodiment may include a gantry 120, a plurality of first light sources 130, a plurality of light sources 130, and a detector 140. The gantry 120 may include a first rotation device, a second rotation device, and a third rotation device that have a ring shape, share an axis of rotation, and are rotatable independently of one another. The plurality of first light sources 130 may be arranged on the first rotation device at regular intervals. The plurality of second light sources 130 may be arranged on the second rotation device at regular intervals. The detector 140 may be arranged in a region of the third rotation device.

The transfer unit 150 according to various embodiments may be a device movable in a bore of the gantry 120 having a ring shape in a direction of an axis of rotation of the gantry 120. A subject that is a computed tomography target may be loaded on the transfer unit 150.

The power supply device 160 according to various embodiments may supply power to operate each component of the CT apparatus 100. The power supply device 160 may supply power required to output X-rays from the plurality of light sources 130.

Figure 2:
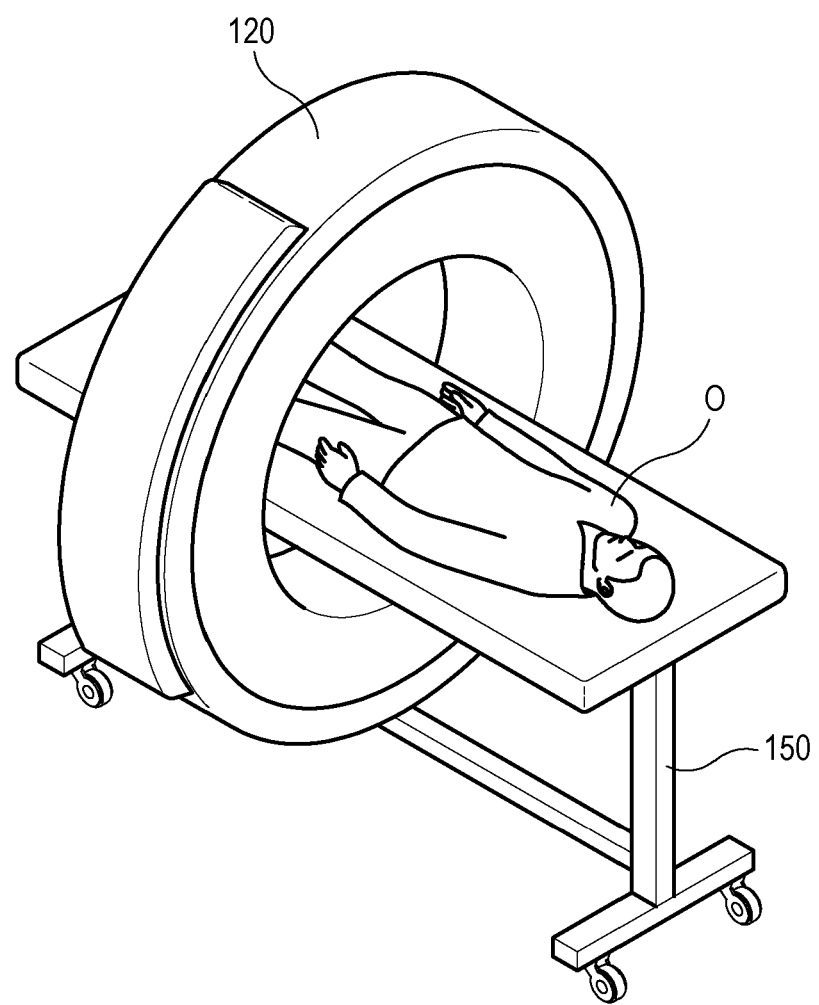
FIG. 2 is a diagram illustrating a CT apparatus according to various embodiments.

FIG. 2 is a diagram illustrating a CT apparatus 100 according to various embodiments. For example, FIG. 2 is a diagram schematically showing only components indispensable for describing an operating method of the CT 100.

Referring to FIG. 2, the CT apparatus 100 according to various embodiments may include a plurality of light sources and at least one detector, emit X-rays to a subject O using the plurality of light sources, and detect X-rays passing through the subject O using the at least one detector.

According to various embodiments, the subject O may be located on a transfer unit 150, and the transfer unit 150 may be moved in a direction of an axis of rotation of a gantry 120 through a bore of the gantry 120.

In order to obtain a CT image of a subject O located in the bore of the gantry 120, the CT apparatus 100 according to various embodiments may emit X-rays to the subject O and detect X-rays passing through the subject O using the at least one detector while the plurality of light sources arranged on the gantry 120 are rotated about the subject O.

Figure 3A:
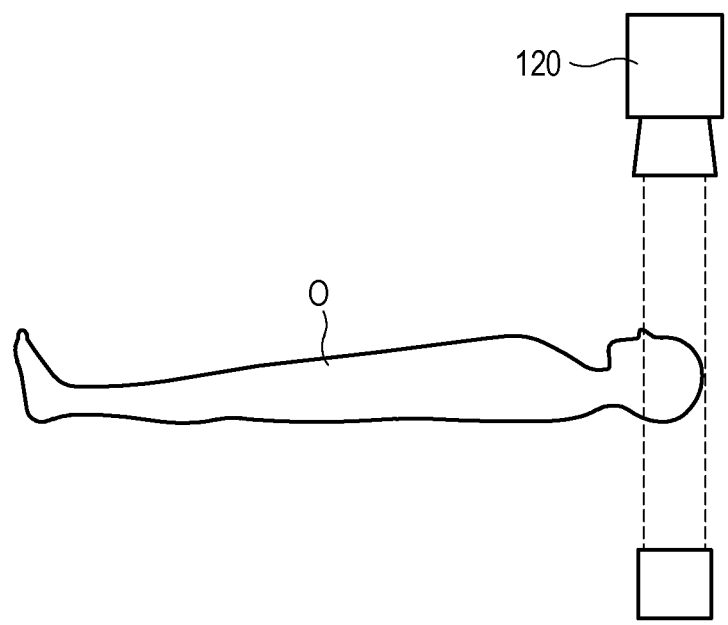

FIGS. 3A and 3B are diagrams illustrating a method of obtaining a circular CT image of a subject according to various embodiments of the present disclosure.

Referring to FIGS. 3A and 3B, the CT apparatus 100 according to various embodiments may obtain circular CT images of different parts of a subject O and create an image of the entire subject O from a combination of the circular CT images. The processor 110 of the CT apparatus 100 may move the transfer unit 150, on which the subject O is loaded, by a predetermined distance and repeatedly obtain a CT image of the subject O a predetermined number of times.

As shown in the example of FIG. 3A, the processor 110 may move the transfer unit 150, on which the subject O is loaded, in a direction of an axis of rotation of the gantry 120 and stop the transfer unit 150 when a head part of the subject O is located in the bore. The processor 110 may obtain a circular CT image of the head part of the subject O using a plurality of light sources 130 and at least one detector 140 in a state in which the transfer unit 150 is stopped. Thereafter, the processor 110 may stop the transfer unit 150 after moving the transfer unit 150 by a predetermined distance. In this case, as shown in FIG. 3B, a chest part of the subject O may be located in the bore. The processor 110 may obtain a circular CT image of the chest part of the subject O using the plurality of light sources 130 and at least one detector 140. The processor 110 may repeatedly perform the above operation a plurality of times to obtain circular CT images of other parts of the subject O and create an image of the entire subject O from a combination of the obtained circular CT images.

Figure 4:
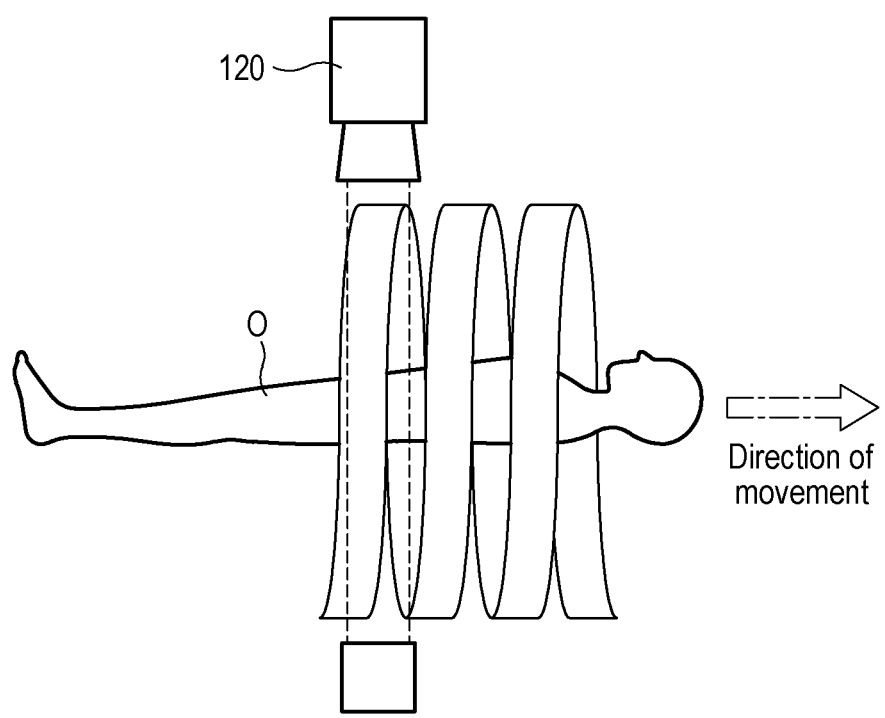
FIG. 4 is a diagram illustrating a method of obtaining a helical CT image of a subject according to various embodiments of the present disclosure.

FIG. 4 is a diagram illustrating a method of obtaining a helical CT image of a subject according to various embodiments of the present disclosure.

Referring to FIG. 4, the CT apparatus 100 according to various embodiments may obtain helical CT images of a subject O and create an image of the entire subject O using the helical CT images. For example, the processor 110 of the CT apparatus 100 may move the transfer unit 150, on which the subject O is loaded, constantly at a predetermined constant speed. The processor 110 may obtain helical CT images of the subject O using the plurality of light sources 130 and at least one detector 140 while the transfer unit 150 is moving at the predetermined speed. The processor 110 may create an image of the entire subject O using the helical CT images of the subject O.

First Embodiment

FIGS. 5 to 9 are diagrams for describing a CT apparatus 100 according to a first embodiment and a CT method using the same.

Figure 5:
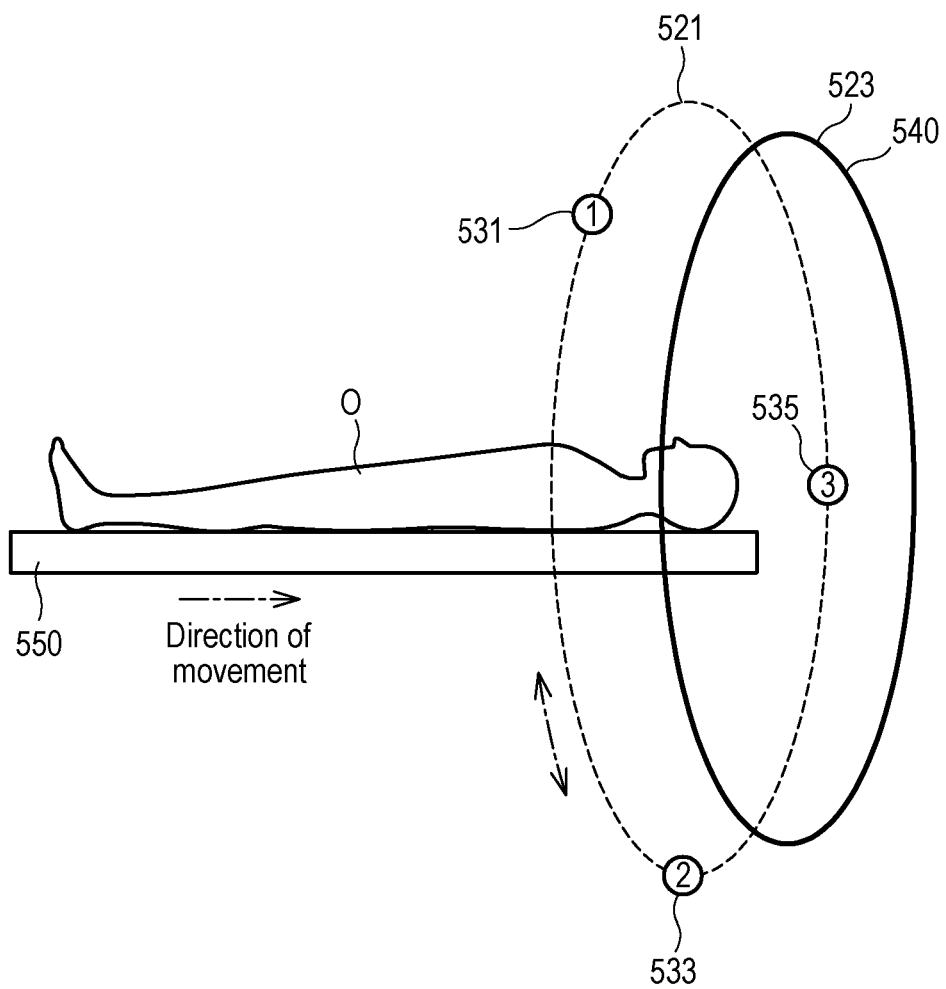
FIG. 5 is a diagram illustrating a CT apparatus according to a first embodiment.
Figure 6:
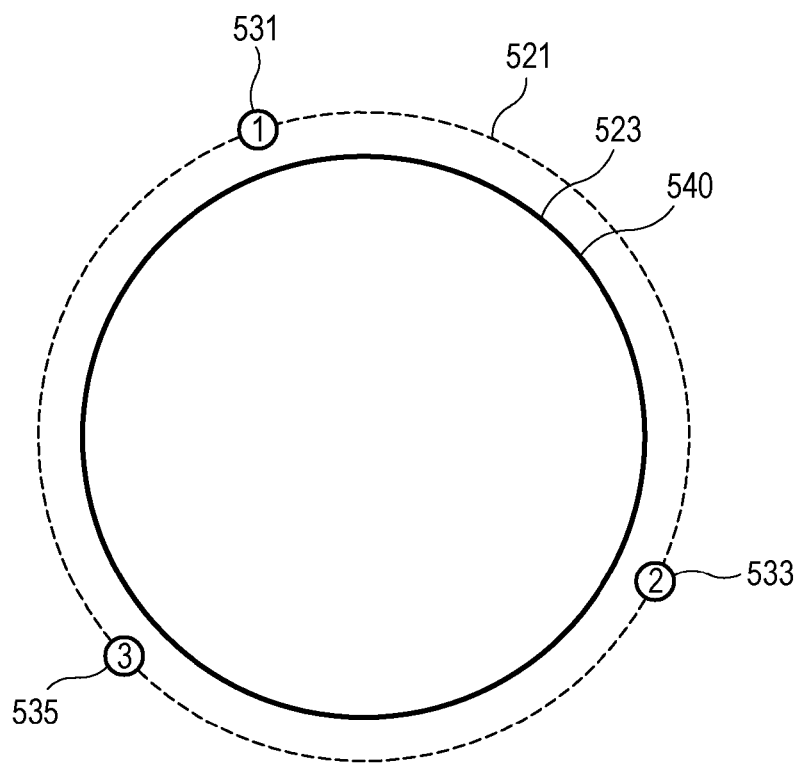
FIG. 6 is a cross-sectional view of an x-y plane of a gantry according to the first embodiment.

FIG. 5 is a diagram illustrating the CT apparatus 100 according to the first embodiment, and FIG. 6 is a cross-sectional view of an x-y plane of a gantry according to the first embodiment.

Referring to FIGS. 5 and 6, the CT apparatus 100 according to various embodiments may include a gantry, a plurality of light sources 531, 533 and 535, and a detector 540. The gantry may include a first rotation device 521 and a second rotation device 523 that have a ring shape, share an axis of rotation, and are rotatable independently of each other. The plurality of light sources 531, 533 and 535 may be arranged on the first rotation device 521 at regular intervals. The detector 540 may be configured to surround all of the inner sides of the second rotation device 523. The plurality of light sources 531, 533 and 535 may emit X-rays to a subject O loaded on a transfer unit 550, and the detector 540 may detect X-rays passing through the subject O. Although in these drawings it is assumed for convenience of description that a total number of the plurality of light sources is three, the number of the plurality of light sources is not limited to three and may be two or greater than three.

According to various embodiments, the processor 110 may determine an interval between angles of the plurality of light sources 531, 533 and 535 arranged on the first rotation device 521 and an angle of rotation of the first rotation device 521 based on the total number of the plurality of light sources 531, 533 and 535. The processor 110 may determine a value obtained by dividing 360 degrees by the total number of the plurality of light sources 531, 533 and 535 as an interval between angles of the plurality of light sources 531, 533 and 535 arranged on the first rotation device 521 and as an angle of rotation of the first rotation device 521. For example, when the total number of the plurality of light sources 531, 533 and 535 is three, the plurality of light sources 531, 533 and 535 may be arranged at intervals of 120 degrees on the first rotation device 521, and an angle of rotation of the first rotation device 521 may be determined to be 120 degrees. In this case, even when the first rotation device 521 is rotated only by 120 degrees, it is possible to create a 3D image of the subject O because there are three light sources arranged at intervals of 120 degrees.

When the detector 540 according to various embodiments is configured to surround all of the inner sides of the second rotation device 523, the processor 110 may cause the detector 540 to detect X-rays passing through the subject O even when X-rays are emitted to the subject O from one of the plurality of light sources 531, 533 and 535.

Figure 7:
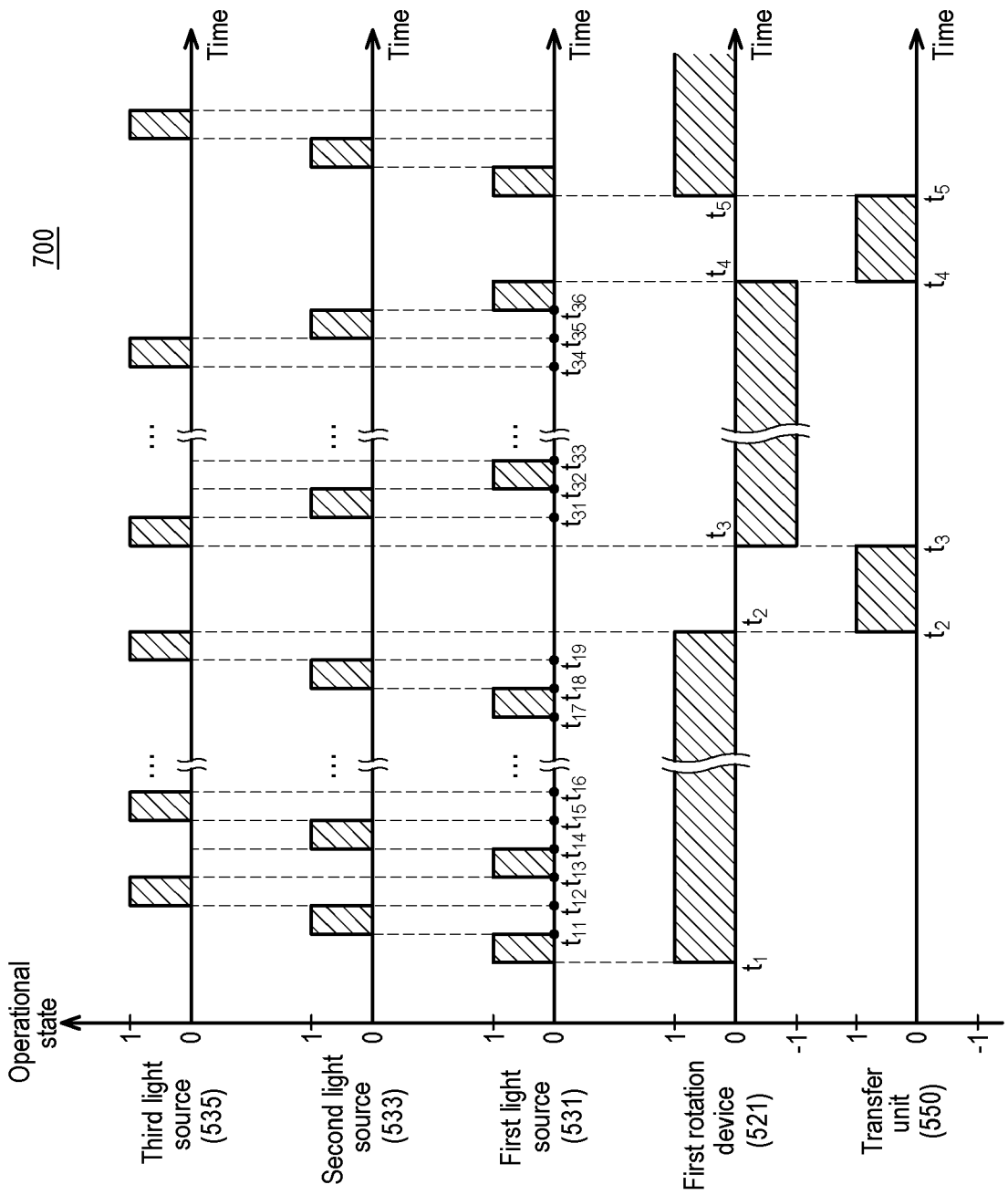
FIG. 7 is a graph showing a CT method performed by the CT apparatus according to the first embodiment.

FIG. 7 is a graph showing a CT method performed by the CT apparatus 100 according to the first embodiment. Specifically, FIG. 7 is a graph showing operational states of the plurality of light sources 531, 533 and 535, the first rotation device 521, and the transfer unit 550 over time when the total number of the plurality of light sources 531, 533 and 535 is three.

In the graph of the first rotation device 521 among the graphs 700, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 531, the second light source 533, and the third light source 535 among the graphs 700, an operational state 1 may represent a state in which X-rays are emitted and an operational state 0 may represent a state in which X-rays are not emitted. In the graph of the transfer unit 550 among the graphs 700, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain circular CT images of different parts of a subject by an operating method shown in the graphs 700 and combine the circular CT images to create an image of the entire subject.

The processor 110 according to various embodiments may rotate the first rotation device 521 in the first rotation direction by an angle of rotation determined based on the total number of the plurality of light sources 531, 533 and 535. For example, when the total number of the plurality of light sources 531, 533 and 535 is three, the angle of rotation of the first rotation device 521 may be determined to be 120 degrees. Referring to the graph of the first rotation device 521 among the graphs 700, the processor 110 may rotate the first rotation device 521 by 120 degrees in the first rotation direction from $t_1$ to $t_2$.

The processor 110 according to various embodiments may emit X-rays to the subject by using at least one of the plurality of light sources 531, 533 and 535 during the rotation of the first rotation device 521 in the first rotation direction. During the rotation of the first rotation device 521 in the first rotation direction, the processor 110 may control the plurality of light sources 531, 533 and 535 to alternately emit X-rays to the subject in units of a unit angle in a predetermined order. For example, whenever the first rotation device 521 is rotated by 1 degree, it is possible to change a light source to emit X-rays in the predetermined order.

Referring to the graphs of the first light source 531, the second light source 533, and the third light source 535 among the graphs 700, the processor 110 may control the first light source 531, the second light source 533, and the third light source 535 to emit X-rays to the subject sequentially and alternately during the rotation of the first rotation device 521 from 0 degrees to 1 degree in the first rotation direction, i.e., from $t_1$ to $t_{13}$. For example, the processor 110 may emit X-rays to the subject by using the first light source 531 among the plurality of light sources 531, 533 and 535 during the rotation of the first rotation device 521 from 0 degrees to ⅓ degrees in the first rotation direction, i.e., $t_1$ to $t_{11}$. The processor 110 may emit X-rays to the subject by using the second light source 533 among the plurality of light sources 531, 533 and 535 during the rotation of the first rotation device 521 from ⅓ degrees to ⅔ degrees, i.e., from $t_{11}$ to $t_{12}$. The processor 110 may control the plurality of light sources 531, 533 and 535 such that X-rays are emitted to the subject by using the third light source 535 among the plurality of light sources 531, 533 and 535 during the rotation of the first rotation device 521 from ⅔ degrees to 1 degree, i.e., from $t_{12}$ to $t_{13}$ Thereafter, the processor 110 may control the plurality of light sources 531, 533 and 535 such that the first light source 531, the second light source 533, and the third light source 535 emit X-rays to the subject sequentially and alternately. When it is assumed that emitting X-rays sequentially from the first light source 531, the second light source 533, and the third light source 535 during the rotation of the first rotation device 521 by 1 degree in the first rotation direction is one sequence, the processor 110 may repeatedly perform the sequence 120 times at an interval of 1 degree to control the plurality of light sources 531, 533 and 535 to alternately emit X-rays to the subject in the predetermined order during the rotation of the first rotation device 521 from 0 degrees to 120 degrees.

The processor 110 according to various embodiments may detect X-rays passing through the subject by the detector 540 during the rotation of the first rotation device 521 in the first rotation direction. In this case, the processor 110 may create at least one raw image of the subject based on the X-rays detected by the detector 540. The processor 110 may create a 3D image of the subject based on the at least one raw image of the subject. In this case, the 3D image of the subject may be a circular CT image. The processor 110 according to various embodiments may rotate the second rotation device 523 on which the detector 540 is arranged in the same direction as the first rotation device 521 or may not rotate the second rotation device 523 during the rotation of the first rotation device 521.

The processor 110 according to various embodiments may stop the first rotation device 521 and move the transfer unit 550 by a predetermined distance after the first rotation device 521 is rotated by a determined angle of rotation in the first rotation direction. Referring to the graph of the transfer unit 550 among the graphs 700, the processor 110 may move the transfer unit 550 by the predetermined distance from $t_2$ to $t_3$. The processor 110 may neither operate the plurality of light sources 531, 533 and 535 nor rotate the first rotation device 521 between $t_2$ and $t_3$.

The processor 110 according to various embodiments may rotate the first rotation device by the determined angle of rotation in a second rotation direction opposite to the first rotation direction. Referring to the graph of the first rotation device 521 among the graphs 700, the processor 110 may rotate the first rotation device 521 by 120 degrees in the second rotation direction from $t_3$ to $t_4$.

The processor 110 according to various embodiments may emit X-rays to the subject by using at least one of the plurality of light sources 531, 533 and 535 during the rotation of the first rotation device 521 in the second rotation direction. During the rotation of the first rotation device 521 in the second rotation direction, the processor 110 may control the plurality of light sources 531, 533 and 535 to alternately emit X-rays to the subject in units of a unit angle in a predetermined order. For example, whenever the first rotation device 521 is rotated by 1 degree, it is possible to change a light source to emit X-rays in the predetermined order.

Referring to the graphs of the first light source 531, the second light source 533, and the third light source 535 among the graphs 700, the processor 110 may control the third light source 535, the second light source 533, and the first light source 531 to emit X-rays to the subject sequentially and alternately during the rotation of the first rotation device 521 from 120 degrees to 119 degrees in the second rotation direction, i.e., from $t_3$ to $t_{33}$. For example, the processor 110 may emit X-rays to the subject by using the third light source 535 among the plurality of light sources 531, 533 and 535 during the rotation of the first rotation device 521 from 120 degrees to $$119\frac{2}{3}$$

degrees, i.e., from $t_3$ to $t_{31}$, in the second rotation direction. The processor 110 may emit X-rays to the subject by using the second light source 533 among the plurality of light sources 531, 533 and 535 during the rotation of the first rotation device 521 from degrees to $119\frac{2}{3}$ degrees, i.e., from $t_{31}$ to $t_{32}$. The processor 110 may control the plurality of light sources 531, 533 and 533 to emit X-rays to the subject by using the first light source 531 among the plurality of light sources 531, 533 and 533 during the rotation of the first rotation device 521 from $119\frac{1}{3}$ to 119 degrees, i.e., from $t_{32}$ to $t_{33}$. Thereafter, the processor 110 may control the plurality of light sources 531, 533 and 535 such that the third light source 535, the second light source 533, and the first light source 531 emit X-rays to the subject sequentially and alternately. When it is assumed that emitting X-rays sequentially from the third light source 535, the second light source 533, and the first light source 531 during the rotation of the first rotation device 521 by 1 degree in the second rotation direction is one sequence, the processor 110 may repeatedly perform the sequence 120 times at an interval of 1 degree to control the plurality of light sources 531, 533 and 535 to alternately emit X-rays to the subject in the predetermined order during the rotation of the first rotation device 521 from 120 degrees to 0 degrees in the second rotation direction. Although it is described above with reference to this drawing that the third light source 535, the second light source 533, and the first light source 531 emit X-rays to the subject sequentially and alternately during the rotation of the first rotation device 521 in the second rotation direction, X-rays may be emitted to the subject sequentially and alternately from the first light source 531, the second light source 533, and the third light source 535.

According to various embodiments, the processor 110 may repeatedly perform a predetermined number of times a cycle of rotating the first rotation device 521 by a determined angle of rotation in the first rotation direction, moving the transfer unit 550 by a predetermined distance in a direction of an axis of rotation after the rotation of the first rotation device 521 by the determined angle of rotation in the first rotation direction, rotating the first rotation device 521 by the determined angle of rotation in the second rotation direction, and moving the transfer unit 550 by the predetermined distance in the direction of the axis of rotation after the rotation of the first rotation device 521 by the determined angle of rotation in the second rotation direction. When the cycle is repeatedly performed the predetermined number of times, circular CT images of different parts of the subject may be obtained. The processor 110 may combine the obtained circular CT images to obtain a 3D image of the entire subject.

Figure 8:
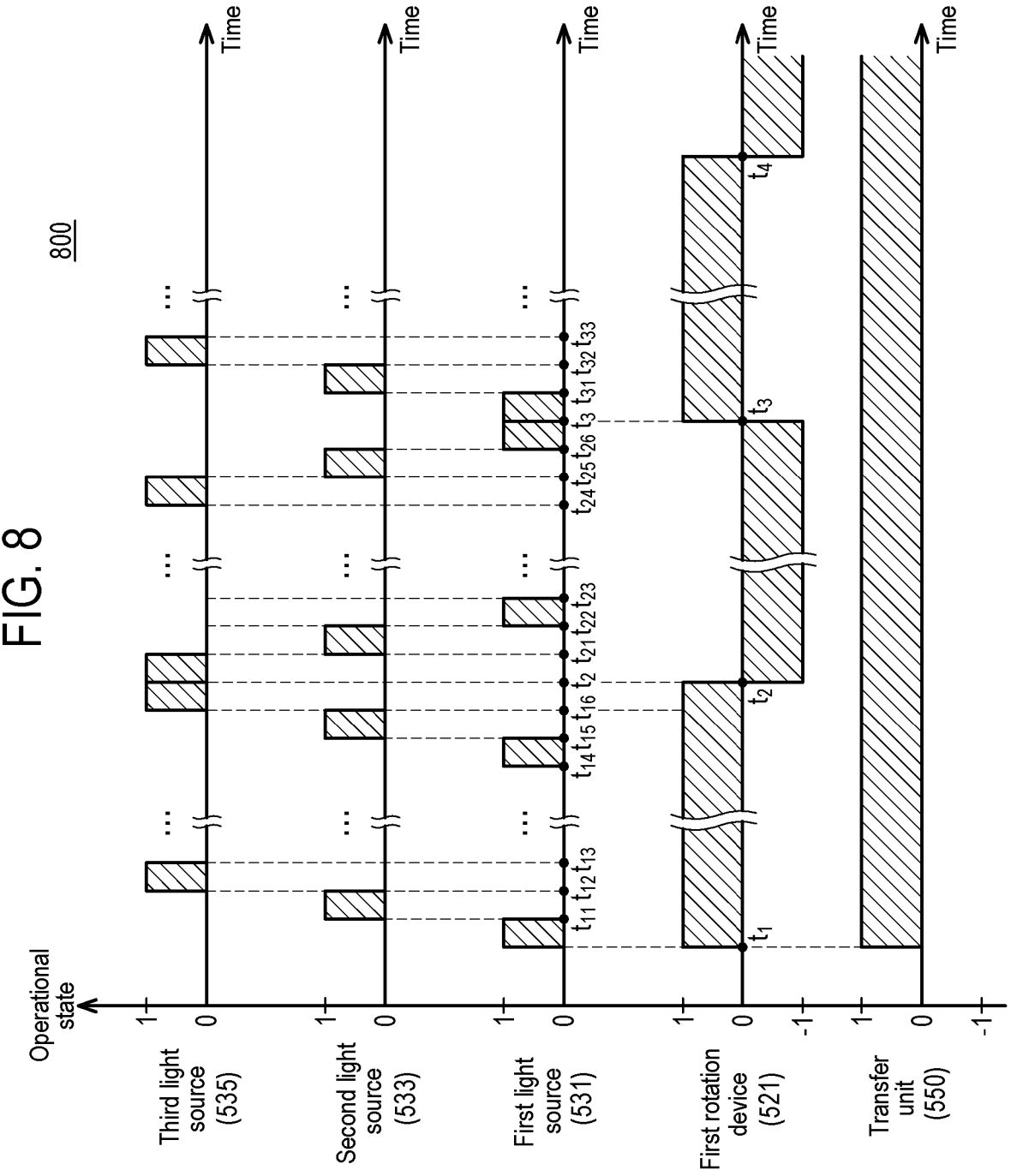
FIG. 8 is a graph showing a CT method performed by the CT apparatus according to the first embodiment.

FIG. 8 is a graph showing a CT method performed by the CT apparatus 100 according to the first embodiment. Specifically, FIG. 8 is a graph showing operational states of the plurality of light sources 531, 533 and 535, the first rotation device 521, and the transfer unit 550 over time when the total number of the plurality of light sources 531, 533 and 535 is three.

In the graph of the first rotation device 521 among the graphs 800, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 531, the second light source 533, and the third light source 535 among the graphs 800, an operational state 1 may represent a state in which X-rays are emitted and an operational state 0 may represent a state in which X-rays are not emitted. In the graph of the transfer unit 550 among the graphs 800, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain helical CT images of a subject by an operating method shown in the graphs 800 and create a 3D image of the entire subject using the obtained helical CT images.

The processor 110 according to various embodiments may rotate the first rotation device 521 in the first rotation direction by an angle of rotation determined based on the total number of the plurality of light sources 531, 533 and 535. For example, when the total number of the plurality of light sources is three, the angle of rotation of the first rotation device 521 may be determined to be 120 degrees. Referring to the graph of the first rotation device 521 among the graphs 800, the processor 110 may rotate the first rotation device 521 in the first rotation direction by 120 degrees from $t_1$ to $t_2$.

The processor 110 according to various embodiments may control the transfer unit 550 to be moved at a predetermined speed in a direction of an axis of rotation in response to the start of the rotation of the first rotation device 521 in the first rotation direction. Referring to the graph of the transfer unit 550 among the graphs 800, the processor 110 may control the transfer unit 550 to be moved constantly at the predetermined speed in a positive direction of the axis of rotation, starting from $t_1$.

The processor 110 according to various embodiments may emit X-rays to the subject by using at least one of the plurality of light sources 531, 533 and 535 during the rotation of the first rotation device 521 in the first rotation direction. During the rotation of the first rotation device 521 in the first rotation direction, the processor 110 may control the plurality of light sources 531, 533 and 535 to alternately emit X-rays to the subject in units of a unit angle in a predetermined order. For example, whenever the first rotation device 521 is rotated by 1 degree, it is possible to change a light source to emit X-rays in the predetermined order.

Referring to the graphs of the first light source 531, the second light source 533, and the third light source 535 among the graphs 800, the processor 110 may control the first light source 531, the second light source 533, and the third light source 535 to emit X-rays to the subject sequentially and alternately during the rotation of the first rotation device 521 from 0 degrees to 1 degree in the first rotation direction, i.e., from $t_1$ to $t_{13}$. For example, the processor 110 may emit X-rays to the subject by using the first light source 531 among the plurality of light sources 531, 533 and 535 during the rotation of the first rotation device 521 from 0 degrees to ⅓ degrees in the first rotation direction, i.e., from $t_1$ to $t_{11}$. The processor 110 may emit X-rays to the subject by using the second light source 533 among the plurality of light sources 531, 533 and 535 during the rotation of the first rotation device 521 from ⅓ degrees to ⅔ degrees, i.e., from $t_{11}$ to $t_{12}$. The processor 110 may control the plurality of light sources 531, 533 and 535 to emit X-rays to the subject by using the third light source 535 among the plurality of light sources 531, 533 and 535 during the rotation of the first rotation device 521 from ⅔ degrees to 1 degree, i.e., from $t_{12}$ to $t_{13}$. Thereafter, the processor 110 may control the plurality of light sources 531, 533 and 535 such that the first light source 531, the second light source 533, and the third light source 535 emit X-rays to the subject sequentially and alternately. When it is assumed that emitting X-rays sequentially from the first light source 531, the second light source 533, and the third light source 535 during the rotation of the first rotation device 521 by 1 degree in the first rotation direction is one sequence, the processor 110 may repeatedly perform the sequence 120 times at an interval of 1 degree to control the plurality of light sources 531, 533 and 535 to alternately emit X-rays to the subject in the predetermined order during the rotation of the first rotation device 521 from 0 degrees to 120 degrees.

The processor 110 according to various embodiments may detect X-rays passing through the subject by the detector 540 during the rotation of the first rotation device 521 in the first rotation direction. In this case, the processor 110 may create at least one raw image of the subject based on the X-rays detected by the detector 540. The processor 110 may create a 3D image of the subject based on the at least one raw image of the subject. In this case, the 3D image of the subject may be a helical CT image of the subject.

The processor 110 according to various embodiments may rotate the first rotation device 521 by a determined angle of rotation in a second rotation direction opposite to the first rotation direction after the rotation of the first rotation device 521 by the determined angle of rotation in the first rotation direction. Referring to the graph of the first rotation device 521 among the graphs 800, the processor 110 may rotate the first rotation device 521 in the second rotation direction by 120 degrees from $t_2$ to $t_3$. In this case, the processor 110 may continuously move the transfer unit 550 at a constant speed in the direction of the axis of rotation.

The processor 110 according to various embodiments may emit X-rays to the subject by using at least one of the plurality of light sources 531, 533 and 535 during the rotation of the first rotation device 521 in the second rotation direction. During the rotation of the first rotation device 521 in the second rotation direction, the processor 110 may control the plurality of light sources 531, 533 and 535 to emit X-rays to the subject in units of a unit angle sequentially and alternately in a predetermined order. For example, whenever the first rotation device 521 is rotated by 1 degree, it is possible to change a light source to emit X-rays in the predetermined order.

Referring to the graphs of the first light source 531, the second light source 533, and the third light source 535 among the graphs 800, the processor 110 may control the third light source 535, the second light source 533, and the first light source 531 to emit X-rays to the subject sequentially and alternately during the rotation of the first rotation device 521 from 120 degrees to 119 degrees, i.e., from $t_2$ to $t_{23}$, in the second rotation direction. For example, the processor 110 may emit X-rays to the subject by using the third light source 535 among the plurality of light sources 531, 533 and 535 during the rotation of the first rotation device 521 from 120 degrees to $$119\tfrac{2}{3}$$

degrees, i.e., from $t_2$ to $t_{21}$, in the second rotation direction. The processor 110 may emit X-rays by using the second light source 533 among the plurality of light sources 531, 533 and 535 during the rotation of the first rotation device 521 from $$119\tfrac{2}{3}$$

to $$119\tfrac{1}{3},$$

i.e., from $t_{21}$ to $t_{22}$. The processor 110 may control the plurality of light sources 531, 533 and 535 to emit X-rays to the subject by using the first light source 531 among the plurality of light sources 531, 533 and 535 during the rotation of the first rotation device 521 from $$119\tfrac{1}{3}$$

degrees to 119 degrees, i.e., from $t_{22}$ to $t_{23}$. Thereafter, the processor 110 may control the plurality of light sources 531, 533 and 535 such that the third light source 535, the second light source 533, and the first light source 531 emit X-rays to the subject sequentially and alternately. When it is assumed that emitting X-rays sequentially from the third light source 535, the second light source 533, and the first light source 531 during the rotation of the first rotation device 521 by 1 degree in the second rotation direction is one sequence, the processor 110 may repeatedly perform the sequence 120 times at an interval of 1 degree to control the plurality of light sources 531, 533 and 535 to alternately emit X-rays to the subject in the predetermined order during the rotation of the first rotation device 521 from 120 degrees to 0 degrees in the second rotation direction. Although it is described above with reference to this drawing that the third light source 535, the second light source 533, and the first light source 531 emit X-rays to the subject sequentially and alternately during the rotation of the first rotation device 521 in the second rotation direction, X-rays may be emitted to the subject sequentially and alternately from the first light source 531, the second light source 533, and the third light source 535.

According to various embodiments, the processor 110 may repeatedly perform a predetermined number of times a cycle of rotating the first rotation device 521 by a determined angle of rotation in a first rotation direction during the movement of the transfer unit 550 at a predetermined speed in a direction of an axis of rotation and rotating the first rotation device 521 by the determined angle of rotation in a second rotation direction during the movement of the transfer unit 550 at the predetermined speed in the direction of the axis of rotation. When the cycle is repeatedly performed the predetermined number of times, helical CT images of the subject may be obtained. The processor 110 may combine the obtained helical CT images to obtain a 3D image of the entire subject.

Figure 9:
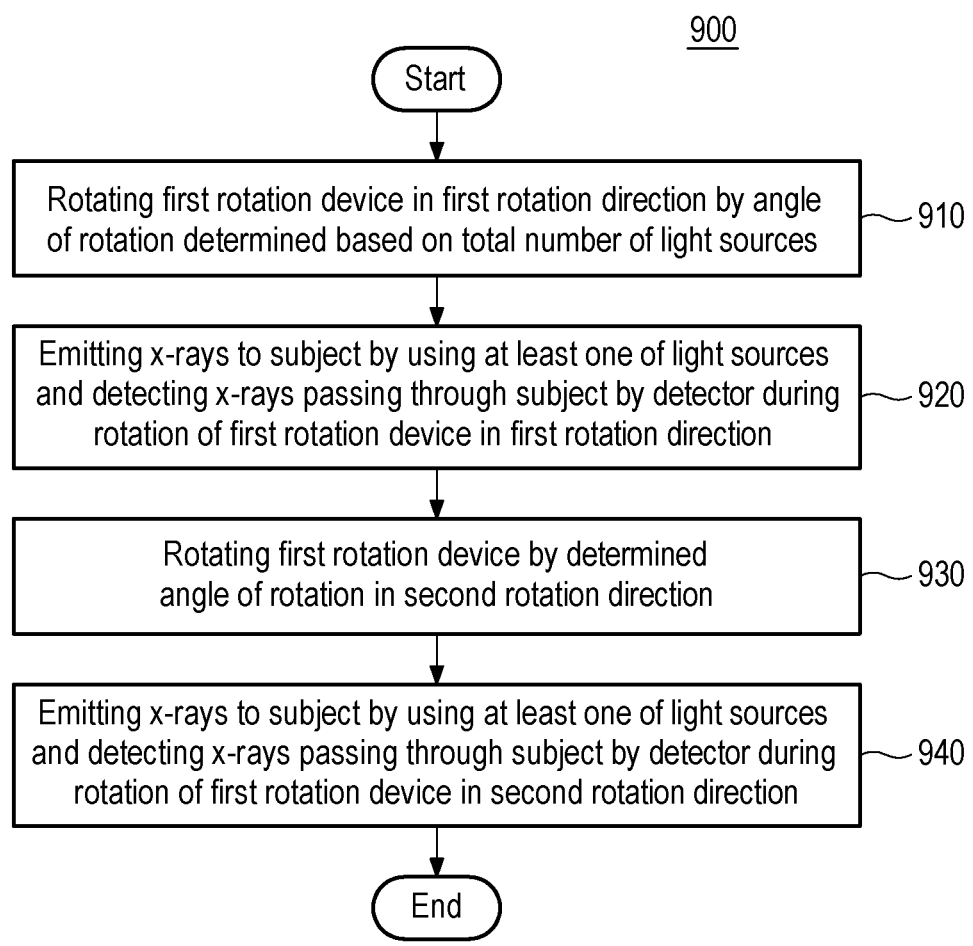
FIG. 9 is a flowchart of operations of the CT apparatus according to the first embodiment.

FIG. 9 is a flowchart 900 of operations of the CT apparatus 100 according to the first embodiment.

Referring to the flowchart 900, in operation 910, the processor 110 of the CT apparatus 100 according to various embodiments may rotate the first rotation device 521 in a first rotation direction by an angle of rotation determined based on the total number of the plurality of light sources 531, 533 and 535. The plurality of light sources 531, 533 and 535 may be arranged on the first rotation device 521 at regular intervals. The determined angle of rotation may be a value obtained by dividing 360 degrees by the total number of the plurality of light sources 531, 533 and 535. For example, when the total number of the plurality of light sources 531, 533 and 535 is three, the processor 110 may rotate the first rotation device 521 by 120 degrees in the first rotation direction.

In operation 920, the processor 110 according to various embodiments may emit X-rays to a subject by using at least one of the plurality of light sources 531, 533 and 535 and detect X-rays passing through the subject by the detector 540 during the rotation of the first rotation device 521 in the first rotation direction. During the rotation of the first rotation device 521 in the first rotation direction, the processor 110 may control the plurality of light sources 531, 533 and 535 to alternately emit X-rays to the subject in units of a unit angle in a predetermined order. The detector 540 may be configured to surround the second rotation device 523. The processor 110 may rotate the second rotation device 523 by the determined angle of rotation in the first rotation direction or may not rotate the second rotation device 523 during the rotation of the first rotation device 521 by the determined angle of rotation in the first rotation direction. The processor 110 according to various embodiments may move the transfer unit 550, on which the subject is loaded, by a predetermined distance in a direction of an axis of rotation of the first rotation device 521 after the rotation of the first rotation device 521 by the determined angle of rotation in the first rotation direction.

In operation 930, the processor 110 according to various embodiments may rotate the first rotation device 521 by the determined angle of rotation in a second rotation direction opposite to the first rotation direction.

In operation 940, the processor 110 according to various embodiments may emit X-rays to the subject by using at least one of the plurality of light sources 531, 533 and 535 and detect X-rays passing through the subject by the detector 540 during the rotation of the first rotation device 521 in the second rotation direction. During the rotation of the first rotation device 521 in the second rotation direction, the processor 110 may control the plurality of light sources 531, 533 and 535 to sequentially and alternately emit X-rays to the subject in units of a unit angle in a predetermined order. The processor 110 may rotate the second rotation device 523 by the determined angle of rotation in the second rotation direction or may not rotate the second rotation device 523 during the rotation of the first rotation device 521 by the determined angle of rotation in the second rotation direction. The processor 110 according to various embodiments may move the transfer unit 550, on which the subject is loaded, by a predetermined distance in the direction of the axis of rotation of the first rotation device 521 after the rotation of the first rotation device 521 by the determined angle of rotation in the second rotation direction.

Second Embodiment

FIGS. 10 to 14 are diagrams for describing a CT apparatus 100 according to a second embodiment and a CT method using the same. A description of parts of the second embodiment that are the same as those of the first embodiment is omitted here.

Figure 10:
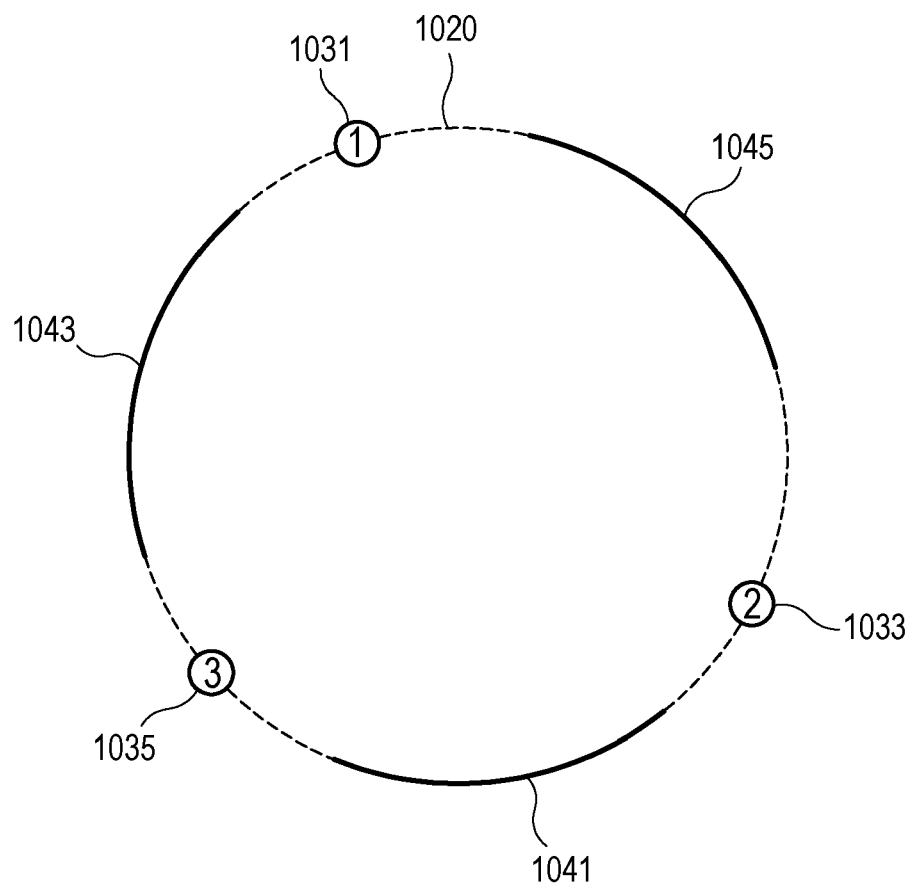
FIG. 10 is a cross-sectional view of an x-y plane of a gantry of a CT apparatus according to a second embodiment.

FIG. 10 is a cross-sectional view of an x-y plane of a gantry of the CT apparatus 100 according to the second embodiment.

Referring to FIG. 10, the CT apparatus 100 according to various embodiments may include a gantry, a plurality of light sources 1031, 1033 and 1035 and a plurality of detectors 1041, 1043 and 1045. The gantry may include a ring-shaped rotation device 1020 rotatable about an axis of rotation. The plurality of light sources 1031, 1033 and 1035 may be arranged on the rotation device 1020 at regular intervals. The plurality of detectors 1041, 1043 and 1045 may be arranged at positions on the rotation device 1020 facing and corresponding to the plurality of light sources 1031, 1033 and 1035 on the rotation device 1020. The plurality of light sources 1031, 1033 and 1035 may emit X-rays to a subject loaded on the transfer unit 1050, and the plurality of detectors 1041, 1043 and 1045 may detect X-rays passing through the subject. Although in this drawing, it is assumed for convenience of description that a total number of the plurality of light sources is three, the total number of the plurality of light sources is not limited to three and may be two or greater than three.

According to various embodiments, the processor 110 may determine an interval between angles of the plurality of light sources 1031, 1033 and 1035 arranged on the rotation device 1020 and an angle of rotation of the rotation device 1020 based on the total number of the plurality of light sources 1031, 1033 and 1035. The processor 110 may determine a value obtained by dividing 360 degrees by the total number of the plurality of light sources 1031, 1033 and 1035 as an interval between angles of the plurality of light sources 1031, 1033 and 1035 arranged on the rotation device 1020 and an angle of rotation of the rotation device 1020.

When the plurality of detectors 1041, 1043 and 1045 according to various embodiments are arranged at positions facing and corresponding to the plurality of light sources 1031, 1033 and 1035 and even when one of the plurality of light sources 1031, 1033 and 1035 emits X-rays to the subject, the processor 110 may detect X-rays passing through the subject by a detector at a position corresponding to the light source 1031, 1033 or 1035 emitting the X-rays. For example, X-rays passing through the subject among X-rays emitted to the subject from the first light source 1031 may be detected by the first detector 1041 arranged at the position corresponding to the first light source 1031, X-rays passing through the subject among X-rays emitted to the subject from the second light source 1033 may be detected by the second detector 1043 arranged at the position corresponding to the second light source 1033, and X-rays passing through the subject among X-rays emitted to the subject from the third light source 1035 may be detected by the third detector 1045 arranged at the position corresponding to the third light source 1035.

Figure 11:
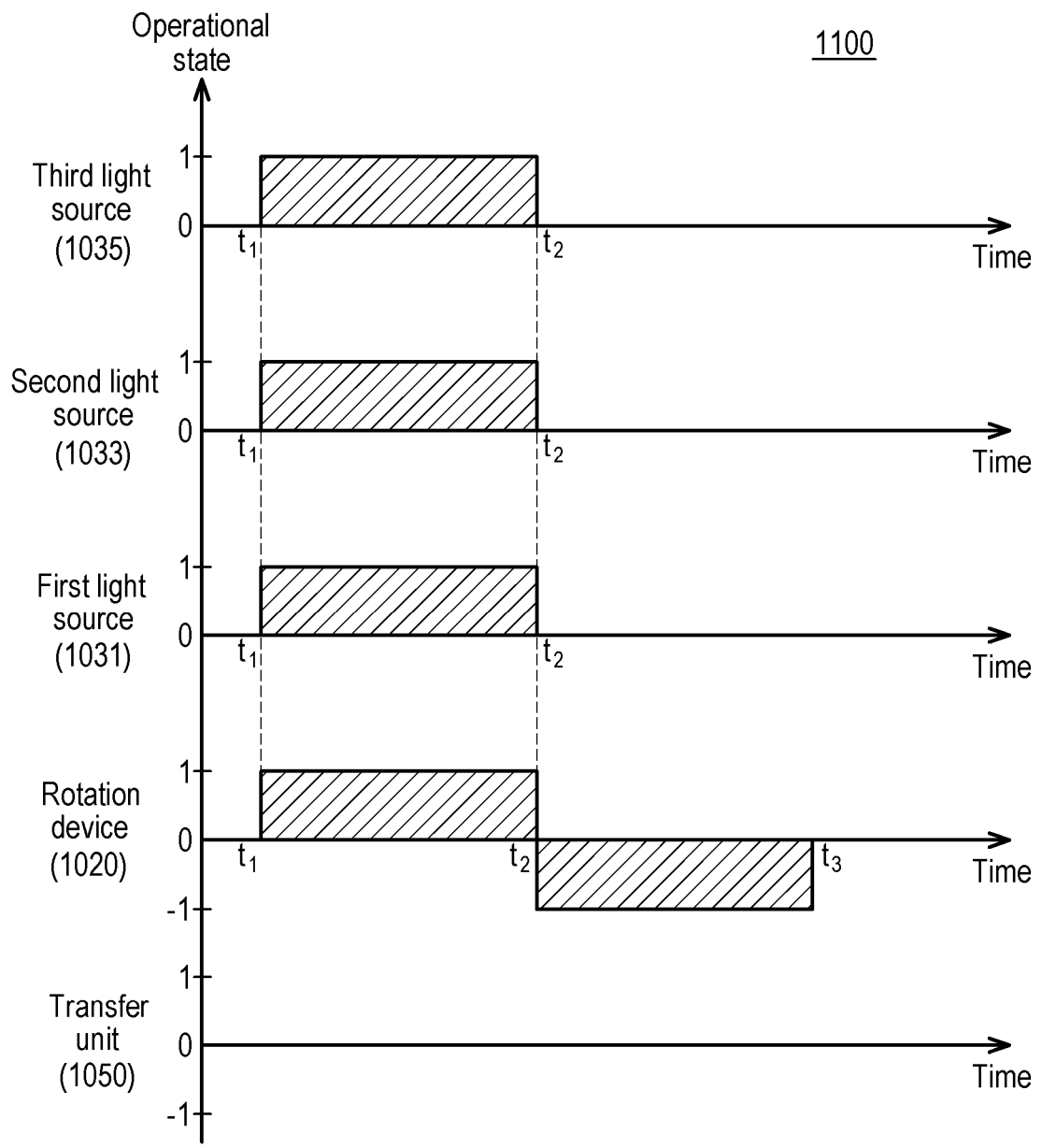
FIG. 11 is a graph showing a CT method performed by the CT apparatus according to the second embodiment.

FIG. 11 is a graph showing a CT method performed by the CT apparatus 100 according to the second embodiment. Specifically, FIG. 11 is a graph showing operational states of the plurality of light sources 1031, 1033 and 1035, the rotation device 1020, and the transfer unit 1050 over time when the total number of the plurality of light sources 1031, 1033 and 1035 is three.

In the graph of the rotation device 1020 among the graphs 1100, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 1031, the second light source 1033, and the third light source 1035 among the graphs 1100, an operational state 1 may represent a state in which X-rays are emitted and an operational state 0 may represent a state in which X-rays are not emitted. In the graph of the transfer unit 1050 among the graphs 1100, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain circular CT images of a subject by an operation method shown in the graphs 1100.

The processor 110 according to various embodiments may rotate the rotation device 1020 in a first rotation direction by an angle of rotation determined based on the total number of the plurality of light sources 1031, 1033 and 1035. For example, when the total number of the plurality of light sources 1031, 1033 and 1035 is three, the angle of rotation of the rotation device 1020 may be determined to be 120 degrees. Referring to the graph of the rotation device 1020 among the graphs 1100, the processor 110 may rotate the rotation device 1020 by 120 degrees from $t_1$ to $t_2$ in the first rotation direction.

Referring to the graph of the transfer unit 1050 among the graphs 1100, the processor 110 according to various embodiments may not move the transfer unit 1050 to obtain a circular CT image of the subject.

The processor 110 according to various embodiments may emit X-rays to the subject by using at least one of the plurality of light sources 1031, 1033 and 1035 during the rotation of the rotation device 1020 in the first rotation direction. For example, the processor 110 may control the plurality of light sources 1031, 1033 and 1035 to emit X-rays to the subject from all of the plurality of light sources 1031, 1033 and 1035 during the rotation of the rotation device 1020 in the first rotation direction. For example, the processor 110 may control the plurality of light sources 1031, 1033 and 1035 to alternately emit X-rays to the subject in units of a unit angle in a predetermined order during the rotation of the rotation device 1020 in the first rotation direction.

For example, referring to the graphs of the first light source 1031, the second light source 1033, and the third light source 1035 among the graphs 1100, the processor 110 may emit X-rays to the subject using all of the first light source 1031, the second light source 1033, and the third light source 1035 during the rotation of the rotation device 1020 from 0 degrees to 120 degrees in the first rotation direction, i.e., from $t_1$ to $t_2$.

For example, as shown in FIG. 7, the processor 110 may control the plurality of light sources 1031, 1033 and 1035 to emit X-rays to the subject sequentially and alternately from the first light source 1031, the second light source 1033, and the third light source 1035. When it is assumed that emitting X-rays sequentially from the first light source 1031, the second light source 1033, and the third light source 1035 during the rotation of the rotation device 1020 by 1 degree in the first rotation direction is one sequence, the processor 110 may repeatedly perform the sequence 120 times at an interval of 1 degree to control the plurality of light sources 1031, 1033 and 1035 to alternately emit X-rays to the subject in the predetermined order during the rotation of the rotation device 1020 from 0 degrees to 120 degrees. The processor 110 according to various embodiments may detect X-rays passing through the subject through the plurality of detectors 1041, 1043 and 1045 during the rotation of the rotation device 1020 in the first rotation direction. In this case, the processor 110 may create at least one raw image of the subject based on the X-rays detected using the plurality of detectors 1041, 1043 and 1045. The processor 110 may create a 3D image of the subject based on the at least one raw image of the subject. In this case, the 3D image of the subject may be a circular CT image.

Figure 12:
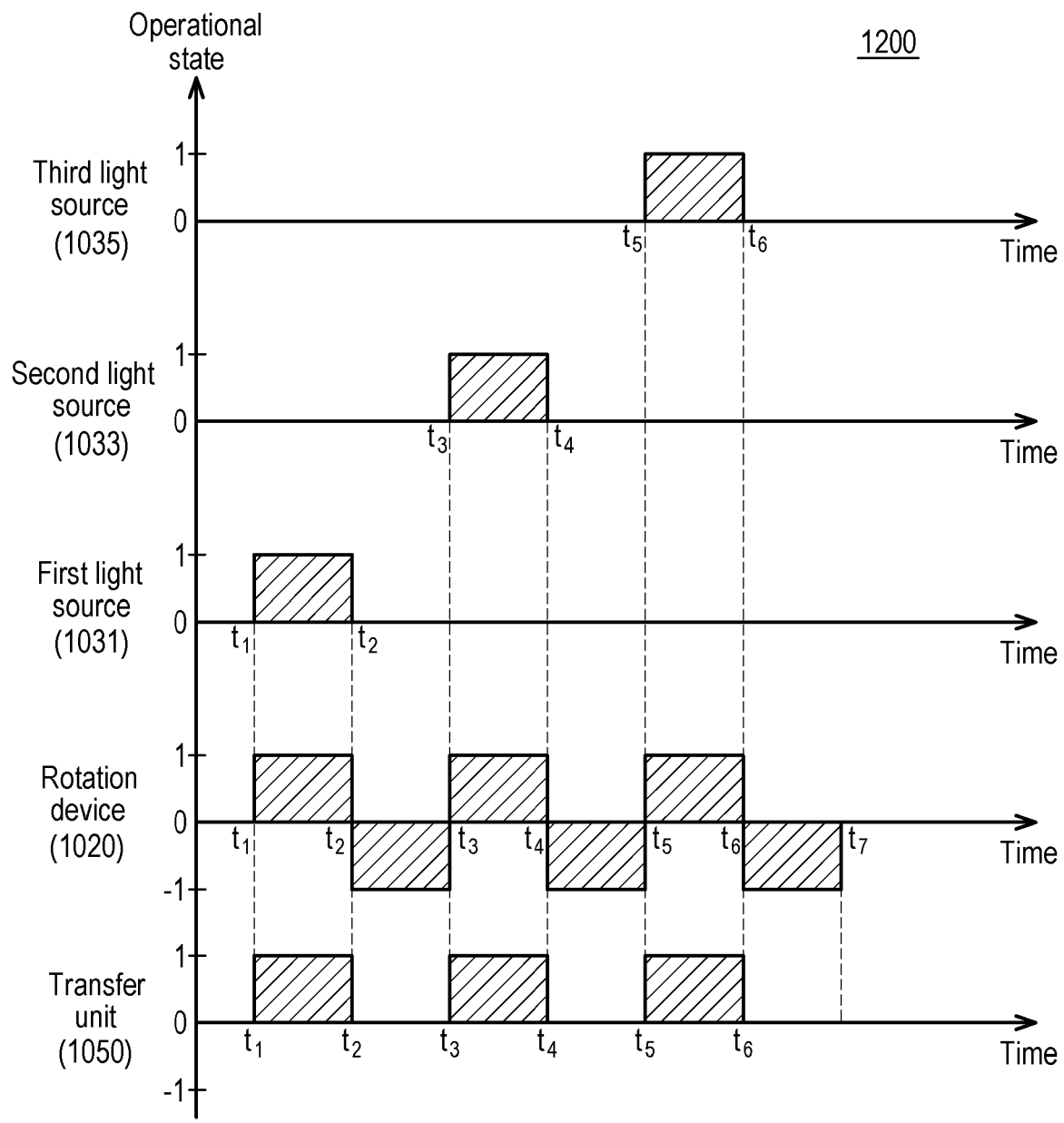
FIG. 12 is a graph showing a CT method performed by the CT apparatus according to the second embodiment.

FIG. 12 is a graph showing a CT method performed by the CT apparatus 100 according to the second embodiment. Specifically, FIG. 12 is a graph showing operational states of the plurality of light sources 1031, 1033 and 1035, the rotation device 1020, and the transfer unit 1050 over time when the total number of the plurality of light sources 1031, 1033 and 1035 is three.

The CT apparatus 100 according to various embodiments may obtain helical CT images of a subject by an operation method shown in graphs 1200.

The processor 110 according to various embodiments may rotate the rotation device 1020 in a first rotation direction by an angle of rotation determined based on the total number of the plurality of light sources 1031, 1033 and 1035. For example, when the total number of the plurality of light sources 1031, 1033 and 1035 is three, the processor 110 may determine the angle of rotation of the rotation device 1020 to be 120 degrees. Referring to the graph of the rotation device 1020 among the graphs 1200, the processor 110 may rotate the rotation device 1020 by 120 degrees from $t_1$ to $t_2$ in the first rotation direction.

The processor 110 according to various embodiments may control the transfer unit 1050 to be moved by a predetermined distance in a direction of the axis of rotation for a predetermined time in response to the start of the rotation of the rotation device 1020 in the first rotation direction. Referring to the graph of the transfer unit 1050 among the graphs 1200, the processor 110 may control the transfer unit 1050 to be moved by the predetermined distance from $t_1$ to $t_2$ in a positive direction of the axis of rotation.

The processor 110 according to various embodiments may emit X-rays to the subject by using one of the plurality of light sources 1031, 1033 and 1035 during the rotation of the rotation device 1020 in the first rotation direction. The processor 110 may emit X-rays to the subject using the first light source 1031 during the rotation of the rotation device 1020 in the first rotation direction from $t_1$ to $t_2$. In this case, the second light source 1033 and the third light source 1035 may not emit X-rays. The first detector 1041 disposed at the position facing and corresponding to the first light source 1031 may detect X-rays passing through the subject during the emission of the X-rays from the first light source 1031. The processor 110 may create at least one raw image of the subject based on the X-rays detected by the first detector 1041.

The processor 110 according to various embodiments may rotate the rotation device 1020 in a second rotation direction opposite to the first rotation direction. The processor 110 may control the rotation device 1020 to be rotated by a determined angle of rotation in the second rotation direction after the rotation of the rotation device 1020 by the determined angle of rotation in the first rotation direction. Referring to the graph of the rotation device 1020 among the graphs 1200, the processor 110 may rotate the rotation device 1020 by 120 degrees from $t_2$ to $t_3$ in the second rotation direction. That is, the processor 110 may return the rotation device 1020 to an original position before the rotation of the rotation device 1020 in the first rotation direction.

The processor 110 according to various embodiments may control the transfer unit 1050 to not be moved, i.e., to be stopped, in response to the start of the rotation of the rotation device 1020 in the second rotation direction. Referring to the graph of the transfer unit 1050 among the graphs 1200, the processor 110 may control the transfer unit 1050 not to be moved from $t_2$ to $t_3$.

The processor 110 according to various embodiments may control all of the plurality of light sources 1031, 1033 and 1035 not to emit X-rays to the subject during the rotation of the rotation device 1020 in the second rotation direction. Referring to the graphs of the first light source 1031, the second light source 1033, and the third light source 1035 among the graphs 1200, the processor 110 may control all of the first light source 1031, the second light source 1033, and the third light source 1035 not to emit X-rays from $t_2$ to $t_3$.

The processor 110 according to various embodiments may repeatedly perform rotating of the rotation device 1020 by the determined angle of rotation in the first rotation direction and rotating of the rotation device 1020 by the determined angle of rotation in the second rotation direction a number of times corresponding to the total number of the plurality of light sources 1031, 1033 and 1035.

The processor 110 according to various embodiments may rotate the rotation device 1020 again by the determined angle of rotation in the first rotation direction. Referring to the graph of the rotation device 1020 among the graphs 1200, the processor 110 may rotate the first rotation device 1020 again by 120 degrees in the first rotation direction from $t_3$ to $t_4$.

The processor 110 according to various embodiments may control the transfer unit 1050 to be moved by a predetermined distance in a direction of an axis of rotation for a predetermined time in response to the start of the rotation of the rotation device 1020 again in the first rotation direction. Referring to the graph of the transfer unit 1050 among the graphs 1200, the processor 110 may control the transfer unit 1050 to be moved by a predetermined distance in a positive direction of the axis of rotation from $t_3$ to $t_4$.

The processor 110 according to various embodiments may emit X-rays to the subject by using one of the plurality of light sources 1031, 1033 and 1035 during the rotation of the rotation device 1020 in the first rotation direction. The processor 110 may emit X-rays to the subject by using the second light source 1033 during the rotation of the rotation device 1020 from $t_3$ to $t_4$. For example, the second light source 1033 may be a light source closest to the first light source 1031 in the first rotation direction. In this case, the first light source 1031 and the third light source 1035 may not emit X-rays. The second detector 1043 disposed at the position facing and corresponding to the second light source 1033 may detect X-rays passing through the subject during the emission of the X-rays from the second light source 1033. The processor 110 may create at least one raw image of the subject based on the X-rays detected by the second detector 1043.

The processor 110 according to various embodiments may rotate the rotation device 1020 again in the second rotation direction opposite to the first rotation direction. Referring to the graph of the rotation device 1020 among the graphs 1200, the processor 110 may rotate the rotation device 1020 again by 120 degrees in the second rotation direction in the second rotation direction from $t_4$ to $t_5$.

The processor 110 according to various embodiments may control the transfer unit 1050 to not be moved, i.e., to be stopped, in response to the start of the rotation of the rotation device 1020 again in the second rotation direction. Referring to the graph of the transfer unit 1050 among the graphs 1200, the processor 110 may control the transfer unit 1050 not to be moved from $t_4$ to $t_5$.

The processor 110 according to various embodiments may control all of the plurality of light sources 1031, 1033 and 1035 not to emit X-rays to the subject during the rotation of the rotation device 1020 again in the second rotation direction. Referring to the graphs of the first light source 1031, the second light source 1033, and the third light source 1035 among the graphs 1200, the processor 110 may control all of the first light source 1031, the second light source 1033, and the third light source 1035 not to emit X-rays from $t_4$ to $t_5$.

The processor 110 according to various embodiment may perform rotating of the rotation device 1020 in the first rotation direction and thereafter rotating of the rotation device 1020 again in the second rotation direction once again from $t_5$ to $t_7$. The processor 110 may emit X-rays to the subject by using the third light source 1035 among the plurality of light sources 1031, 1033 and 1035 during the rotation of the rotation device 1020 in the first rotation direction from $t_5$ to $t_6$.

The processor 110 may create at least one raw image of the subject through the above operations and create a helical CT image of the subject based on the at least one raw image.

Figure 13:
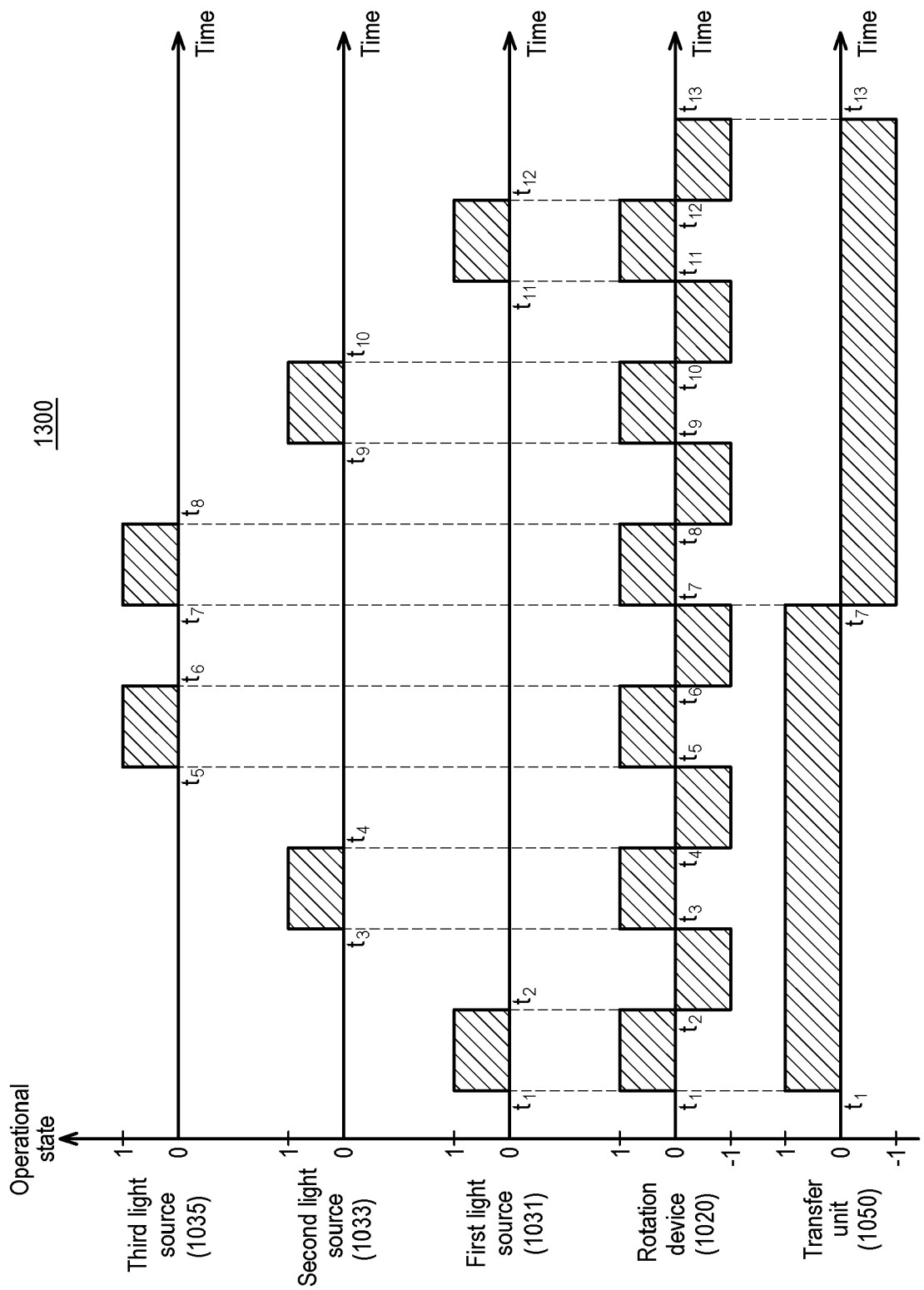
FIG. 13 is a graph showing a CT method performed by the CT apparatus according to the second embodiment.

FIG. 13 is a graph showing a CT method performed by the CT apparatus 100 according to the second embodiment. Specifically, FIG. 13 is a graph showing operational states of the plurality of light sources 1031, 1033 and 1035, the rotation device 1020, and the transfer unit 1050 over time when the total number of the plurality of light sources 1031, 1033 and 1035 is three.

The CT apparatus 100 according to various embodiments may obtain helical CT images of a subject by an operating method shown in graphs 1300 and create a 3D image of the entire subject using the obtained helical CT images. A description of parts of FIG. 13 that are the same as those of FIG. 12 is omitted here.

According to various embodiments, operational states of the rotation device 1020, the first light source 1031, the second light source 1033, and the third light source 1035 from $t_1$ to $t_7$ are the same as the above states described with reference to FIG. 12. Referring to graphs of the rotation device 1020, the first light source 1031, the second light source 1033, and the third light source 1035 among the graphs 1300, the processor 110 may control the rotation device 1020 to be repeatedly rotated by a determined angle of rotation in a first rotation direction and thereafter rotated in a second rotation direction. The processor 110 may emit X-rays to the subject using one of the plurality of light sources 1031, 1033 and 1035 during the rotation of the rotation device 1020 in the first rotation direction. For example, as shown in the graphs 1300, the processor 110 may control the plurality of light sources 1031, 1033 and 1035 to emit X-rays to the subject sequentially from the first light source 1031, the second light source 1033, and the third light source 1035.

Referring to a graph of the transfer unit 1050 among the graphs 1300, the processor 110 according to various embodiments may control the transfer unit 1050 to be moved constantly at a predetermined speed in a positive direction of an axis of rotation from $t_1$ to $t_7$. Some data of helical CT images of the subject may be lost when the transfer unit 1050 is not stopped during the rotation of the rotation device 1020 in the second rotation direction, i.e., during restoration of the rotation device 1020 to an original position. To supplement the lost data, the processor 110 may move the transfer unit 1050 again at the predetermined speed in a negative direction of the axis of rotation. For example, the processor 110 may control the transfer unit 1050 to be moved constantly at the predetermined speed in the negative direction of the axis of rotation from $t_7$ to $t_{13}$.

Referring to graphs of the rotation device 1020, the first light source 1031, the second light source 1033, and the third light source 1035 among the graphs 1300, the processor 110 may control the rotation device 1020 to be repeatedly rotated by a determined angle of rotation in the first rotation direction and thereafter rotated in the second rotation direction from $t_7$ to $t_{13}$. The processor 110 may emit X-rays to the subject using one of the plurality of light sources 1031, 1033 and 1035 during the rotation of the rotation device 1020 in the first rotation direction. For example, as shown in the graphs 1300, the processor 110 may control the plurality of light sources 1031, 1033 and 1035 to emit X-rays to the subject sequentially from the third light source 1035, the second light source 1033 and the first light source 1031 from $t_7$ to $t_{13}$.

The processor 110 may create at least one raw image of the subject through the above operations and create a helical CT image of the subject based on the at least one raw image.

Figure 14:
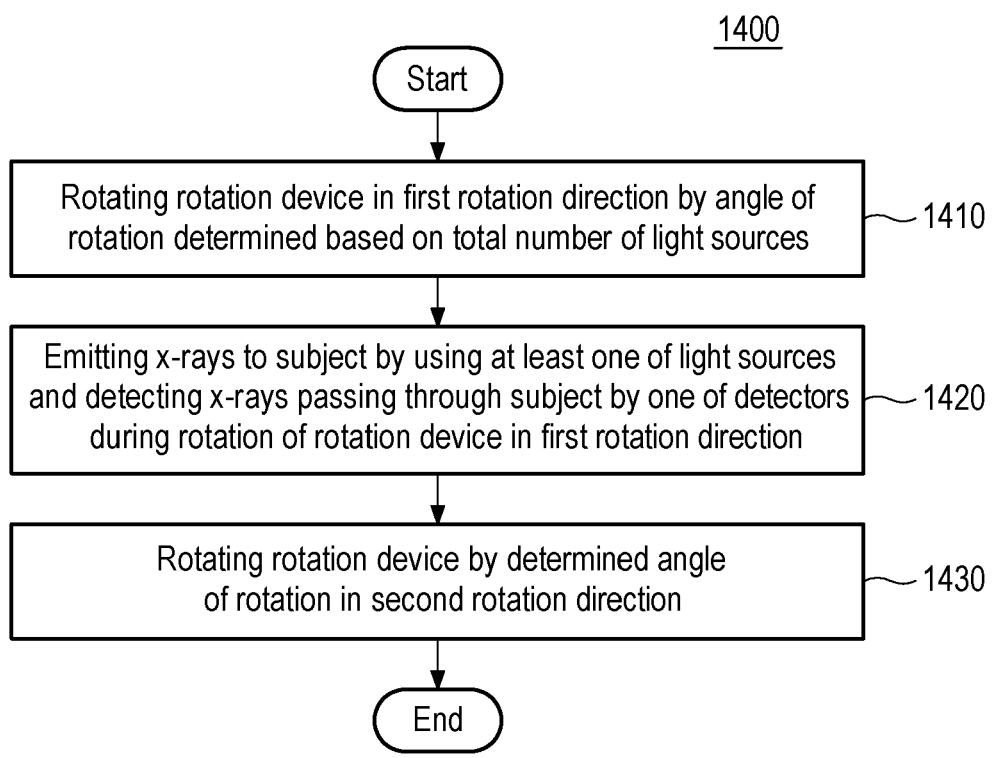
FIG. 14 is a flowchart of operations of the CT apparatus according to the second embodiment.

FIG. 14 is a flowchart 1400 of operations of the CT apparatus 100 according to the second embodiment.

Referring to the flowchart 1400, in operation 1410, the processor 110 of the CT apparatus 100 according to various embodiments may rotate the rotation device 1020 in a first rotation direction by an angle of rotation determined based on the total number of the plurality of light sources 1031, 1033 and 1035.

In operation 1420, the processor 110 according to various embodiments may emit X-rays to a subject by using at least one of the plurality of light sources 1031, 1033 and 1035 and detect X-rays passing through the subject by one of the plurality of detectors 1041, 1043 and 1045 during the rotation of the rotation device 1020 in the first rotation direction. The processor 110 may create at least one raw image of the subject based on the X-rays detected using one of the plurality of detectors 1041, 1043 and 1045. The processor 110 may create a 3D image of the subject using the at least one raw image of the subject.

In operation 1430, the processor 110 according to various embodiments may rotate the rotation device 1020 by the determined angle of rotation in the second rotation direction. The processor 110 according to various embodiments may control all of the plurality of light sources 1031, 1033 and 1035 not to emit X-rays to the subject during the rotation of the rotation device 1020 by the determined angle of rotation in the second rotation direction.

Third Embodiment

Figure 15A:
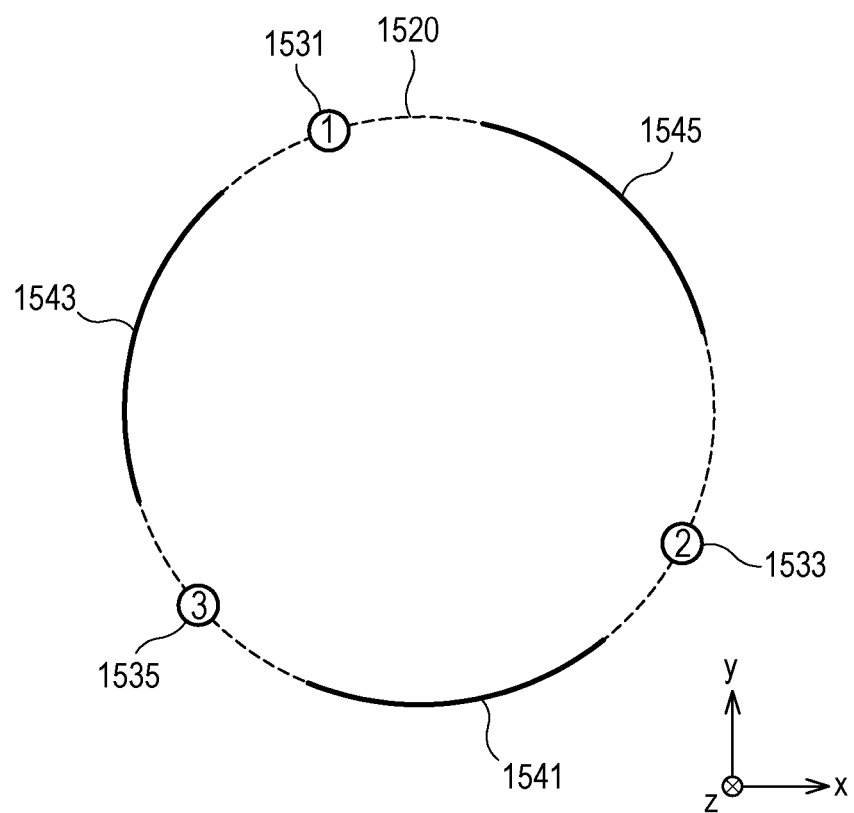
FIG. 15A is a cross-sectional view of an x-y plane of a gantry of a CT apparatus according to a third embodiment.
Figure 15B:
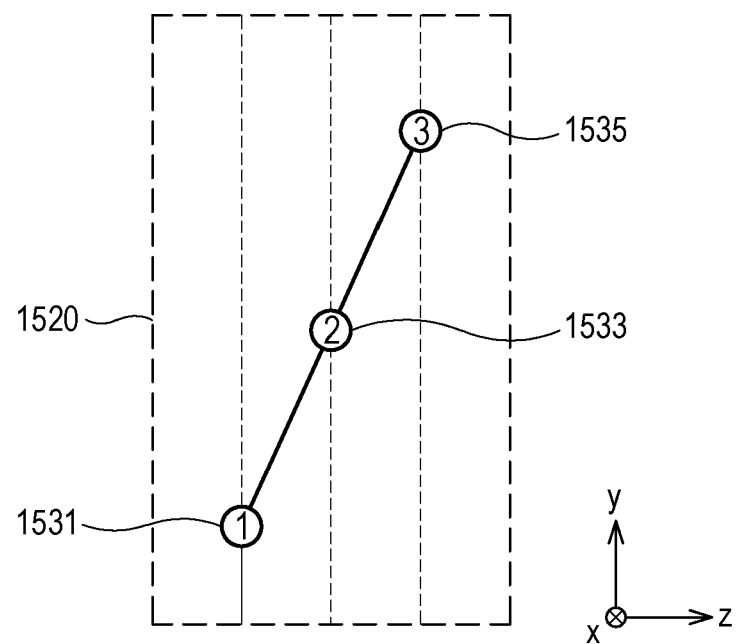
FIG. 15B is a cross-sectional view of a y-z plane of the gantry according to the third embodiment.
Figure 16:
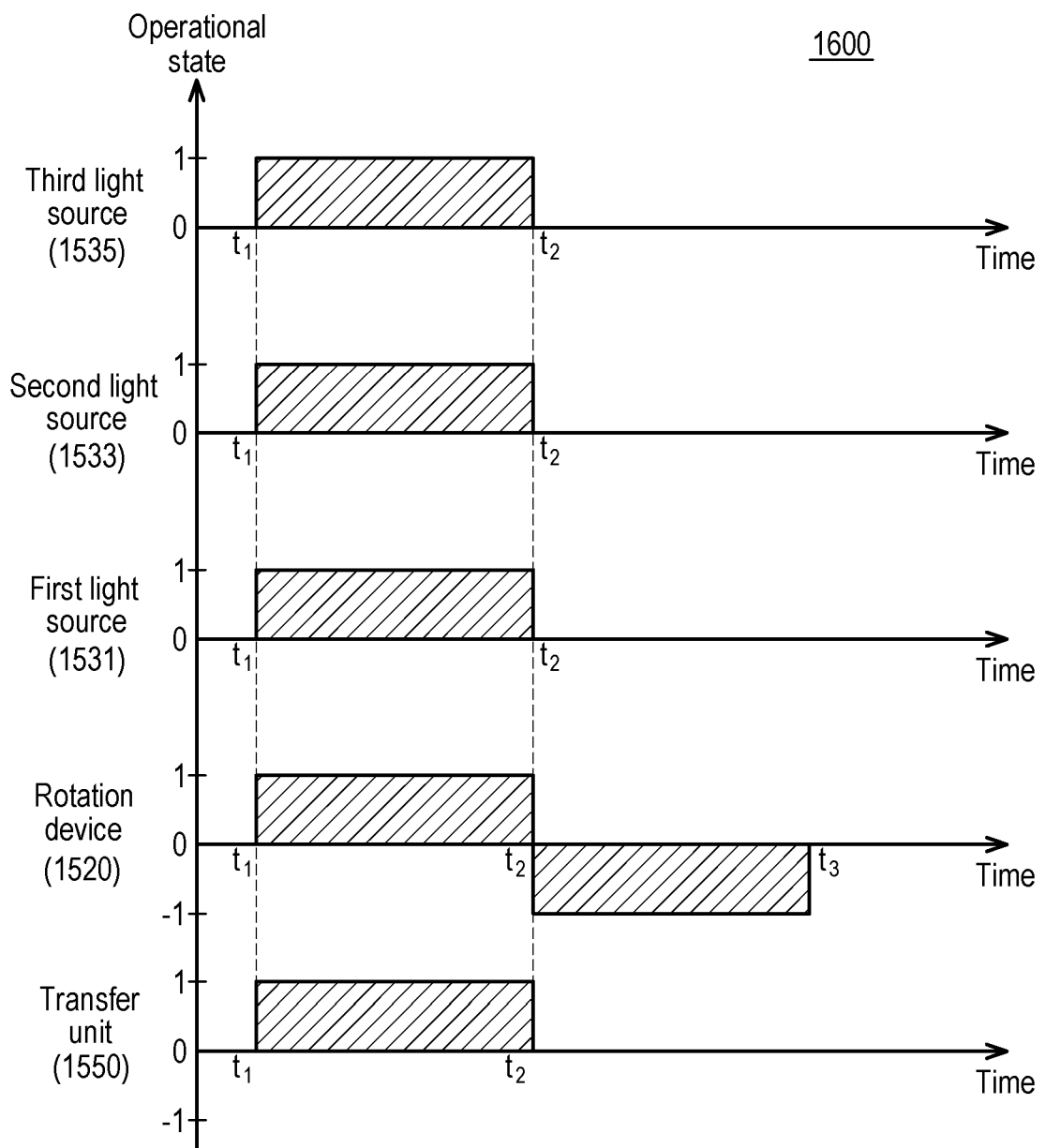
FIG. 16 is a graph showing a CT method performed by the CT apparatus according to the third embodiment.

FIGS. 15A to 16 are diagrams for describing a CT apparatus 100 according to a third embodiment and a CT method using the same. A description of parts of the third embodiment that are the same as those of the second embodiment is omitted here.

FIG. 15A is a cross-sectional view of an x-y plane of a gantry of the CT apparatus 100 according to the third embodiment, and FIG. 15B is a cross-sectional view of a y-z plane of the gantry according to the third embodiment. In the CT apparatus 100 according to the third embodiment, positions of a plurality of light sources on a z-axis in the CT apparatus 100 according to the second embodiment are changed.

Referring to FIG. 15A, the CT apparatus 100 according to various embodiments may include a gantry, a plurality of light sources 1531, 1533 and 1535 and a plurality of detectors 1541, 1543 and 1545. The gantry may include a ring-shaped rotation device 1520 rotatable about an axis of rotation. The plurality of light sources 1531, 1533 and 1535 may be arranged on the rotation device 1520 at regular intervals. The plurality of detectors 1541, 1543 and 1545 may be arranged at positions facing and corresponding to the plurality of light sources 1531, 1533 and 1535. The plurality of light sources 1531, 1533 and 1535 may emit X-rays to a subject loaded on a transfer unit 1550, and the plurality of detectors 1541, 1543 and 1545 may detect X-rays passing through the subject. Although in this drawing, it is assumed for convenience of description that a total number of the plurality of light sources is three, the total number of the plurality of light sources is not limited to three and may be two or greater than three.

According to various embodiments, the processor 110 may determine an interval between angles of the plurality of light sources 1531, 1533 and 1535 arranged in the rotation device 1520 and an angle of rotation of the rotation device 1520 based on the total number of the plurality of light sources 1531, 1533 and 1535. The processor 110 may determine a value obtained by dividing 360 degrees by the total number of the plurality of light sources 1531, 1533 and 1535 as an interval between angles of the plurality of light sources 1531, 1533 and 1535 arranged in the rotation device 1520 and as an angle of rotation of the rotation device 1520.

When the plurality of detectors 1541, 1543 and 1545 according to various embodiments are arranged at positions facing and corresponding to the plurality of light sources 1531, 1533 and 1535 and even when one of the plurality of light sources 1531, 1533 and 1535 emits X-rays to the subject, the processor 110 may detect X-rays passing through the subject by the detector 1541, 1543 or 1545 at a position corresponding to the light source 1531, 1533 or 1535 emitting the X-rays. For example, X-rays passing through the subject among X-rays emitted to the subject from the first light source 1531 may be detected by the first detector 1541 arranged at the position corresponding to the first light source 1531, X-rays passing through the subject among X-rays emitted to the subject from the second light source 1533 may be detected by the second detector 1543 arranged at the position corresponding to the second light source 1533, and X-rays passing through the subject among X-rays emitted to the subject from the third light source 1535 may be detected by the third detector 1545 arranged at the position corresponding to the third light source 1535.

Referring to FIG. 15B, the plurality of light sources 1531, 1533 and 1535 according to various embodiments may be arranged at positions on an axis of rotation of the rotation device 1520 that are spaced a certain distance from one another. For example, positions of the plurality of light sources 1531, 1533 and 1535 on a z-axis may be different from one another. For example, the position of the first light source 1531 on the z-axis, the position of the second light source 1533 on the z-axis, and the position of the third light source 1535 on the z-axis may be different from one another. For example, the difference between the positions of the first light source 1531 and the second light source 1533 on the z-axis may be the same as the difference between the positions of the second light source 1533 and the third light source 1535 on the z-axis.

FIG. 16 is a graph showing a CT method performed by the CT apparatus 100 according to the third embodiment. Specifically, FIG. 16 is a graph showing operational states of the plurality of light sources 1531, 1533 and 1535, the rotation device 1520, and the transfer unit 1550 over time when the total number of the plurality of light sources 1531, 1533 and 1535 is three.

In the graph of the rotation device 1520 among the graphs 1600, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 1531, the second light source 1533, and the third light source 1535 among the graphs 1600, an operational state 1 may represent a state in which X-rays are emitted, and an operational state 0 may represent a state in which X-rays are not emitted. In the graph of the transfer unit 1550 among the graphs 1600, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain helical CT images of a subject by an operation method shown in graphs 1600.

The processor 110 according to various embodiments may rotate the rotation device 1520 in the first rotation direction by an angle of rotation determined based on the total number of the plurality of light sources. For example, when the total number of the plurality of light sources is three, it may be determined that the angle of rotation of the rotation device 1520 is 120 degrees. Referring to the graph of the rotation device 1520 among the graphs 1600, the processor 110 may rotate the rotation device 1520 by 120 degrees in the first rotation direction from $t_1$ to $t_2$.

Referring to the graph of the transfer unit 1550 among the graphs 1600, the processor 110 according to various embodiments may move the transfer unit 1550 at a predetermined speed in the direction of the axis of rotation to obtain helical CT images of the subject from $t_1$ to $t_2$. In the CT apparatus 100 according to the third embodiment, the positions of the plurality of light sources 1531, 1533 and 1535 on the z-axis are different from one another and thus helical CT images of the subject may be obtained even when the transfer unit 1550 is moved during the rotation of the rotation device 1520 in the first rotation direction.

The processor 110 according to various embodiments may emit X-rays to the subject through at least one of the plurality of light sources 1531, 1533 and 1535 during the rotation of the rotation device 1520 in the first rotation direction. For example, the processor 110 may control the plurality of light sources 1531, 1533 and 1535 to emit X-rays to the subject from all of the plurality of light sources 1531, 1533 and 1535 during the rotation of the rotation device 1520 in the first rotation direction. For example, the processor 110 may control the plurality of light sources 1531, 1533 and 1535 to alternately emit X-rays to the subject in units of a unit angle in a predetermined order during the rotation of the rotation device 1520 in the first rotation direction.

For example, referring to the graphs of the first light source 1531, the second light source 1533, and the third light source 1535 among the graphs 1600, the processor 110 may emit X-rays to the subject using all of the first light source 1531, the second light source 1533, and the third light source 1535 during the rotation of the rotation device 1520 from 0 degrees to 120 degrees in the first rotation direction, i.e., from $t_1$ to $t_2$.

For example, as shown in FIG. 7, the processor 110 may control the plurality of light sources 1531, 1533 and 1535 to emit X-rays to the subject sequentially and alternately from the first light source 1531, the second light source 1533, and the third light source 1535. When it is assumed that emitting X-rays sequentially from the first light source 1531, the second light source 1533, and the third light source 1535 during the rotation of the rotation device 1520 by 1 degree in the first rotation direction is one sequence, the processor 110 may repeatedly perform the sequence 120 times at an interval of 1 degree to control the plurality of light sources 1531, 1533 and 1535 to alternately emit X-rays to the subject in the predetermined order during the rotation of the rotation device 1520 from 0 degrees to 120 degrees.

The processor 110 according to various embodiments may detect X-rays passing through the subject through the plurality of detectors 1541, 1543 and 1545 during the rotation of the rotation device 1520 in the first rotation direction. In this case, the processor 110 may create at least one raw image of the subject based on the X-rays detected using the plurality of detectors 1541, 1543 and 1545. The processor 110 may create a 3D image of the subject based on the at least one raw image of the subject. In this case, the 3D image of the subject may be a helical CT image.

The processor 110 according to various embodiments may rotate the rotation device 1520 by a determined angle of rotation in the second rotation direction. That is, the processor 110 may return the rotation device 1520 to an original position before the rotation of the rotation device 1520 in the first rotation direction. Referring to the graph of the rotation device 1520 among the graphs 1600, the processor 110 may rotate the rotation device 1520 by 120 degrees in the second rotation direction from $t_2$ to $t_3$.

Fourth Embodiment

FIGS. 17 to 21 are diagrams for describing a CT apparatus 100 according to a fourth embodiment and a CT method using the same.

Figure 17:
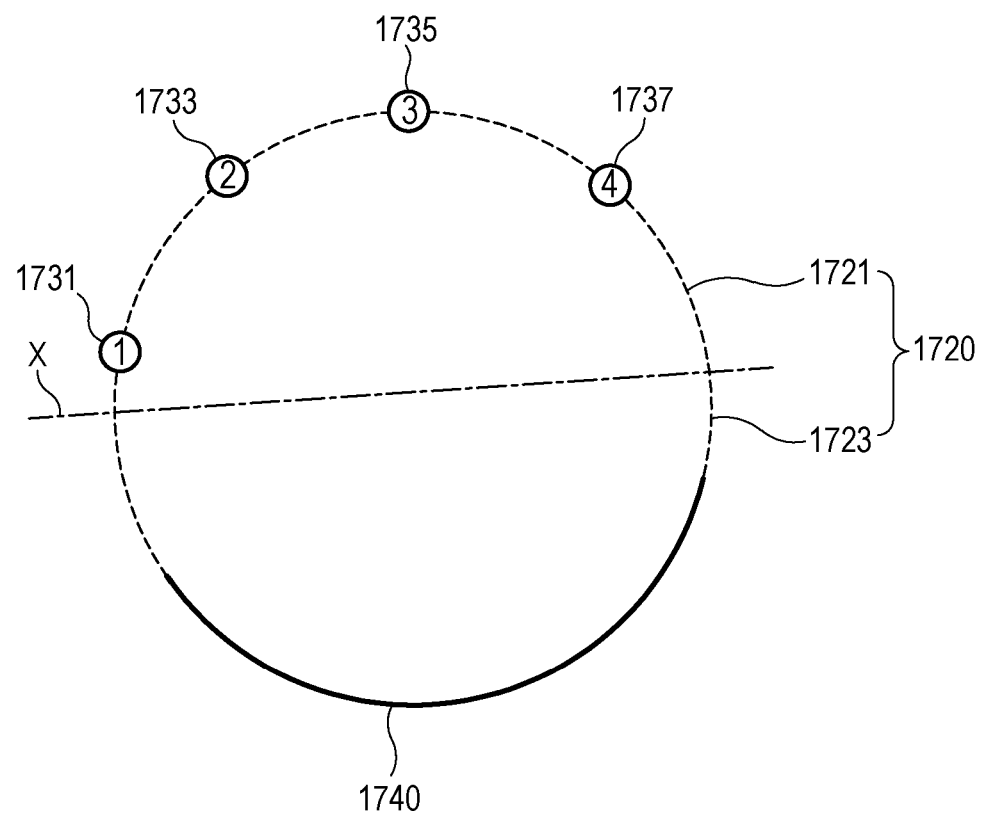
FIG. 17 is a cross-sectional view of an x-y plane of a gantry of a CT apparatus according to a fourth embodiment.

FIG. 17 is a cross-sectional view of an x-y plane of a gantry of the CT apparatus 100 according to the fourth embodiment.

Referring to FIG. 17, the CT apparatus 100 according to various embodiments may include a gantry, a plurality of light sources 1731, 1733, 1735 and 1737, and a detector 1740. The gantry may include a ring-shaped rotation device 1720 rotatable about an axis of rotation. The gantry may be divided into a first sub-device 1721 and a second sub-device 1723 along a division line X. In this case, a subject may be easily placed inside the gantry, because it is possible to combine the second sub-device 1723 with the first sub-device 1721 after the object is placed inside the first sub-device 1721 of the rotation device 1720. Although for convenience of description, it is described above that the rotation device 1720 is divided in half along the division line X, the rotation device 1720 is not necessarily divided into the first sub-device 1721 and the second sub-device 1723 along a 180-degree line passing the center thereof and may be divided into various-sized parts. When the first sub-device 1721 and the second sub-device 1723 are combined with each other, the first sub-device 1721 and the second sub-device 1723 may be rotated together with the rotation of the rotation device 1720.

The plurality of light sources 1731, 1733, 1735 and 1737 according to various embodiments may be spaced a certain distance from the first sub-device 1721. The plurality of light sources 1731, 1733, 1735 and 1737 may emit X-rays to a subject loaded on the transfer unit 1750. Although in this drawing, it is assumed for convenience of description that a total number of the plurality of light sources is four, the total number of the plurality of light sources is not limited to four and may be two or three or greater than four.

The detector 1740 according to various embodiments may be provided on the second sub-device 1723. For example, when it is assumed that the plurality of light sources 1731, 1733, 1735 and 1737 are point light sources, a cone beam angle of the plurality of light sources 1731, 1733, 1735 and 1737 is about 30 degrees, and thus, the second sub-device 1723 has a size occupying 210 degrees (180 degrees+30 degrees) of an entire circumference of the rotation device 1720 with respect to the center of the rotation device 1720, and the detector 1740 may be configured to entirely surround inner sides of the second sub-device 1723.

According to various embodiments, the processor 110 may determine an interval between angles of the plurality of light sources 1731, 1733, 1735 and 1737 arranged in the first sub-device 1721 and an angle of rotation of the rotation device 1720 based on the total number of the plurality of light sources 1731, 1733, 1735 and 1737. The processor 110 may determine a value obtained by dividing 180 degrees by the total number of the plurality of light sources 1731, 1733, 1735 and 1737 as an interval between angles of the plurality of light sources 1731, 1733, 1735 and 1737 arranged in the first sub-device 1721 and as the angle of rotation of the rotation device 1720. For example, when the total number of the plurality of light sources 1731, 1733, 1735 and 1737 is four, the plurality of light sources 1731, 1733, 1735 and 1737 may be arranged at 45-degree intervals on the first sub-device 1721, and it may be determined that the angle of rotation of the rotation device 1720 is 45 degrees.

When the detector 1740 according to various embodiments is configured to entirely surround the second sub-device 1723, the processor 110 is capable of detecting X-rays passing through the subject by the detector 1740 even when one of the plurality of light sources 1731, 1733, 1735 and 1737 arranged in the first sub-device 1721 emits X-rays to the subject.

Figure 18:
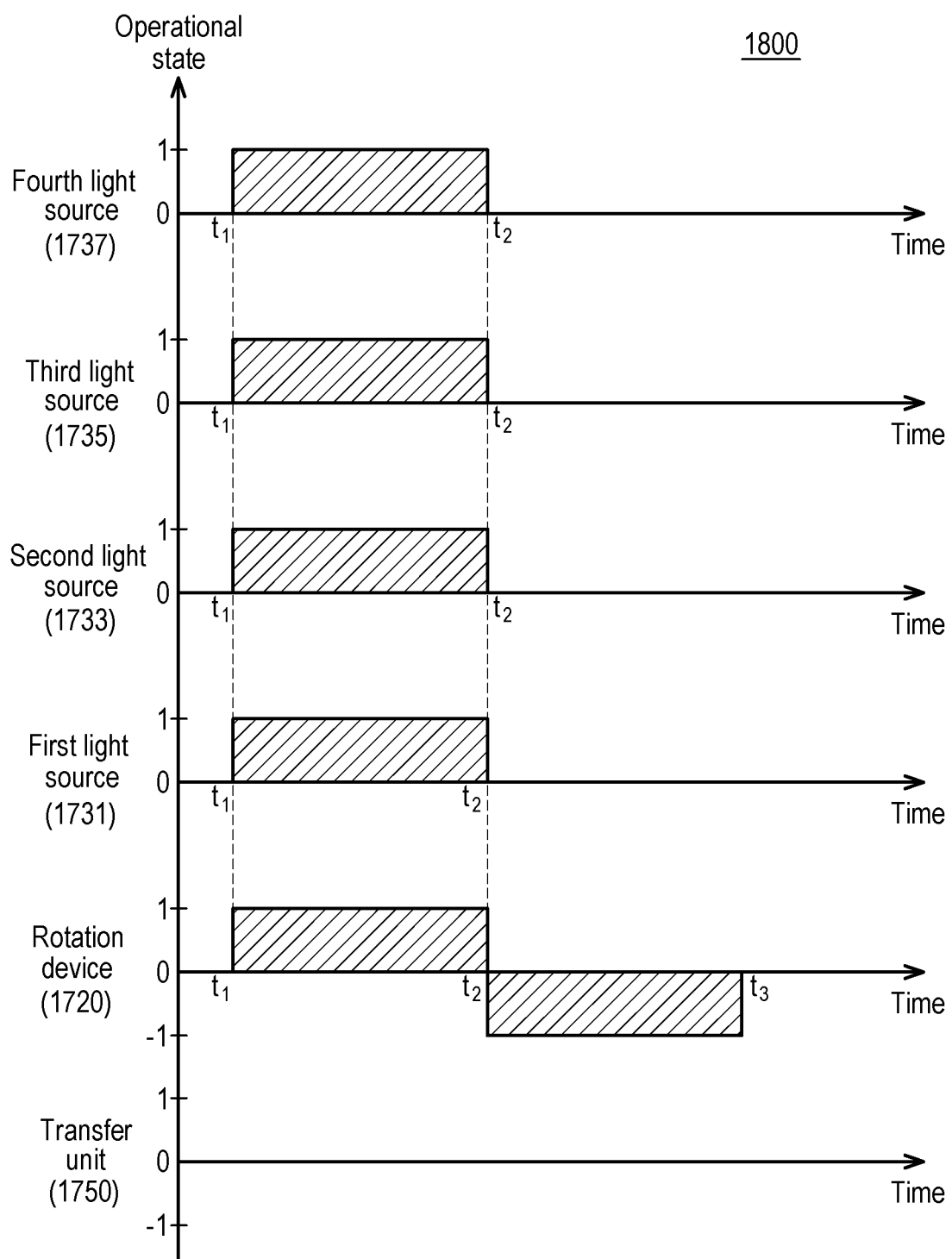
FIG. 18 is a graph showing a CT method performed by the CT apparatus according to the fourth embodiment.

FIG. 18 is a graph showing a CT method performed by the CT apparatus 100 according to the fourth embodiment. Specifically, FIG. 18 is a graph showing operational states of the plurality of light sources 1731, 1733, 1735 and 1737, the rotation device 1720, and the transfer unit 1750 over time when the total number of the plurality of light sources 1731, 1733, 1735 and 1737 is four.

In the graph of the rotation device 1720 among the graphs 1800, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 1731, the second light source 1733, the third light source 1735, and the fourth light source 1737 among the graphs 1800, an operational state 1 may represent a state in which X-rays are emitted and an operational state 0 may represent a state in which X-rays are not emitted. In the graph of the transfer unit 1750 among the graphs 1800, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain circular CT images of a subject by an operation method shown in the graphs 1800.

The CT apparatus 100 according to various embodiments may obtain circular CT images of a subject by an operation method shown in the graphs 1800.

The processor 110 according to various embodiments may rotate the rotation device 1720 in the first rotation direction by an angle of rotation determined based on the total number of the plurality of light sources 1731, 1733, 1735 and 1737. For example, when the total number of the plurality of light sources 1731, 1733, 1735 and 1737 is four, the angle of rotation of the rotation device 1720 may be determined to be 45 degrees. Referring to the graph of the rotation device 1720 among the graphs 1800, the processor 110 may rotate the rotation device 1720 by 45 degrees in the first rotation direction from $t_1$ to $t_2$.

Referring to the graph of the transfer unit 1750 among the graphs 1800, the processor 110 according to various embodiments may not move the transfer unit 1750 to obtain a circular CT image of the subject.

The processor 110 according to various embodiments may emit X-rays to the subject by using at least one of the plurality of light sources 1731, 1733, 1735 and 1737 during the rotation of the rotation device 1720 in the first rotation direction. For example, the processor 110 may control the plurality of light sources 1731, 1733, 1735 and 1737 to emit X-rays to the subject from all of the plurality of light sources 1731, 1733, 1735 and 1737 during the rotation of the rotation device 1720 in the first rotation direction. The processor 110 may control the plurality of light sources 1731, 1733, 1735 and 1737 to repeatedly perform a sequence of alternately emitting X-rays to the subject in units of a unit angle from the plurality of light sources 1731, 1733, 1735 and 1737 in a predetermined order during the rotation of the rotation device 1720 in the first rotation direction.

For example, referring to the graphs of the first light source 1731, the second light source 1733, the third light source 1735, and the fourth light source 1737 among the graphs 1800, the processor 110 may emit X-rays to the subject using all of the first light source 1731, the second light source 1733, the third light source 1735, and the fourth light source 1737 during the rotation of the rotation device 1720 from 0 degrees to 45 degrees, i.e., from $t_1$ to $t_2$, in the first rotation direction.

For example, as shown in FIG. 7, the processor 110 may control the plurality of light sources 1731, 1733, 1735 and 1737 to repeatedly perform a sequence of emitting X-rays to the subject in units of a unit angle alternately and sequentially from the plurality of light sources 1731, 1733, 1735 and 1737.

The processor 110 according to various embodiments may detect X-rays passing through the subject by the detector 1740 during the rotation of the rotation device 1720 in the first rotation direction. In this case, the processor 110 may create at least one raw image of the subject based on the X-rays detected by the detector 1740. The processor 110 may create a 3D image of the subject based on the at least one raw image of the subject. In this case, the 3D image of the subject may be a circular CT image.

The processor 110 according to various embodiments may rotate the rotation device 1720 by the determined angle of rotation in the second rotation direction. That is, the processor 110 may return the rotation device 1720 to an original position before the rotation of the rotation device 1720 in the first rotation direction. Referring to the graph of the rotation device 1720 among the graphs 1800, the processor 110 may rotate the rotation device 1720 by 45 degrees in the second rotation direction from $t_2$ to $t_3$.

Figure 19:
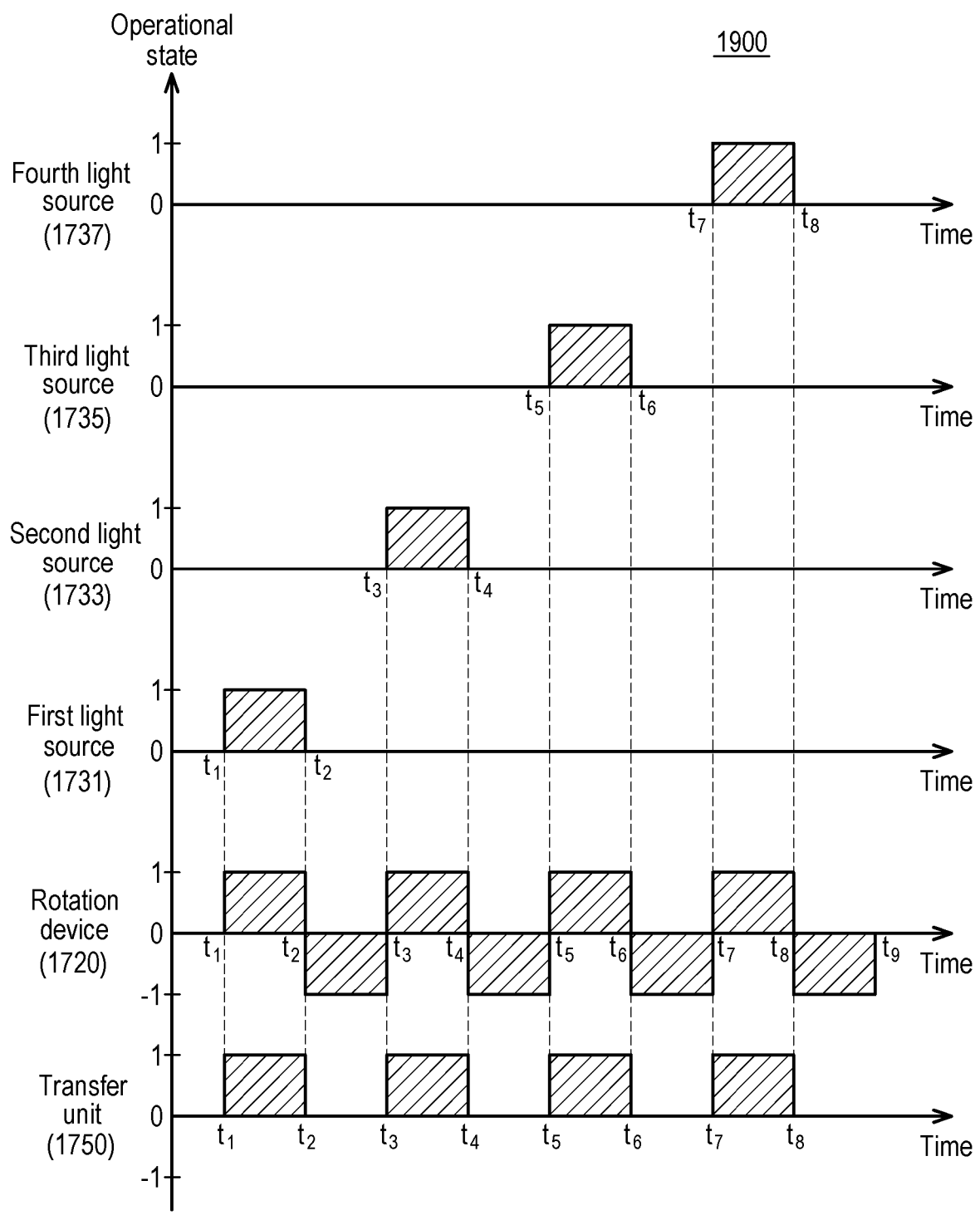
FIG. 19 is a graph showing a CT method performed by the CT apparatus according to the fourth embodiment.

FIG. 19 is a graph showing a CT method performed by the CT apparatus 100 according to the fourth embodiment. Specifically, FIG. 19 is a graph showing operational states of the plurality of light sources 1731, 1733, 1735 and 1737, the rotation device 1720, and the transfer unit 1750 over time when the total number of the plurality of light sources 1731, 1733, 1735 and 1737 is four.

The CT apparatus 100 according to various embodiments may obtain helical CT images of a subject by an operation method shown in graphs 1900.

The processor 110 according to various embodiments may rotate the rotation device 1720 in the first rotation direction by an angle of rotation determined based on the total number of the plurality of light sources 1731, 1733, 1735 and 1737. For example, when the total number of the plurality of light sources 1731, 1733, 1735 and 1737 is four, it may be determined that the angle of rotation of the rotation device 1720 is 45 degrees. Referring to a graph of the rotation device 1720 among the graphs 1900, the processor 110 may rotate the rotation device 1720 by 45 degrees in the first rotation direction from $t_1$ to $t_2$.

The processor 110 according to various embodiments may control the transfer unit 1750 to be moved by a predetermined distance in a direction of an axis of rotation for a predetermined time in response to the start of the rotation of the rotation device 1720 in the first rotation direction. Referring to a graph of the transfer unit 1750 among the graphs 1900, the processor 110 may control the transfer unit 1750 by the predetermined distance in a positive direction of the axis of rotation from $t_1$ to $t_2$.

The processor 110 according to various embodiments may emit X-rays to the subject by using one of the plurality of light sources 1731, 1733, 1735 and 1737 during the rotation of the rotation device 1720 in the first rotation direction. The processor 110 may emit X-rays to the subject by using the first light source 1731 during the rotation of the rotation device 1720 in the first rotation direction from $t_1$ to $t_2$. In this case, the second light source 1733, the third light source 1735, and the fourth light source 1737 may not emit X-rays. The detector 1740 may detect X-rays passing through the subject during the emission of the X-rays from the first light source 1731. The processor 110 may create at least one raw image of the subject based on the X-rays detected by the detector 1740.

The processor 110 according to various embodiments may rotate the rotation device 1720 in a second rotation direction opposite to the first rotation direction. The processor 110 may control the rotation device 1720 to be rotated by a determined angle of rotation in the second rotation direction after the rotation of the rotation device 1720 by the determined angle of rotation in the first rotation direction. Referring to the graph of the rotation device 1720 among the graphs 1900, the processor 110 may rotate the rotation device 1720 by 45 degrees in the second rotation direction from $t_2$ to $t_3$. That is, the processor 110 may return the rotation device 1720 to an original position before the rotation of the rotation device 1720 in the first rotation direction.

The processor 110 according to various embodiments may control the transfer unit 1750 to not be moved, i.e., to be stopped, in response to the start of the rotation of the rotation device 1720 in the second rotation direction. Referring to the graph of the transfer unit 1750 among the graphs 1900, the processor 110 may control the transfer unit 1750 not to be moved from $t_2$ to $t_3$.

The processor 110 according to various embodiments may control all of the plurality of light sources 1731, 1733, 1735 and 1737 not to emit X-rays to the subject during the rotation of the rotation device 1720 in the second rotation direction. Referring to the graphs of the first light source 1731, the second light source 1733, the third light source 1735, and the fourth light source 1737 among the graphs 1900, the processor 110 may control all of the first light source 1731, the second light source 1733 and the third light source 1735 not to emit X-rays from $t_2$ to $t_3$.

The processor 110 according to various embodiments may repeatedly perform rotating of the rotation device 1720 by the determined angle of rotation in the first rotation direction and rotating of the rotation device 1720 by the determined angle of rotation in the second rotation direction a number of times corresponding to the total number of the plurality of light sources.

The processor 110 according to various embodiments may rotate the rotation device 1720 again by the determined angle of rotation in the first rotation direction. Referring to the graph of the rotation device 1720 among the graphs, the processor 110 may rotate the rotation device 1720 again by 45 degrees in the first rotation direction from $t_3$ to $t_4$.

The processor 110 according to various embodiments may control the transfer unit 1750 to be moved by a predetermined distance in a direction of an axis of rotation for a predetermined time in response to the start of the rotation of the rotation device 1720 again in the first rotation direction. Referring to the graph of the transfer unit 1750 among the graphs 1900, the processor 110 may control the transfer unit 1750 to be moved by a predetermined distance in a positive direction of the axis of rotation from $t_3$ to $t_4$.

The processor 110 according to various embodiments may emit X-rays to the subject by using one of the plurality of light sources 1731, 1733, 1735 and 1737 during the rotation of the rotation device 1720 in the first rotation direction. The processor 110 may emit X-rays to the subject using the second light source 1733 during the rotation of the rotation device 1720 in the first rotation direction from $t_3$ to $t_4$. For example, the second light source 1733 may be the light source closest to the first light source 1731 in the first rotation direction. In this case, the first light source 1731, the third light source 1735 and the fourth light source 1737 may not emit X-rays. The detector 1740 may detect X-rays passing through the subject during the emission of the X-rays from the second light source 1733. The processor 110 may create at least one raw image of the subject based on the X-rays detected by the detector 1740.

The processor 110 according to various embodiments may rotate the rotation device 1720 again in the second rotation direction opposite to the first rotation direction. Referring to the graph of the rotation device 1720 among the graphs 1900, the processor 110 may rotate the rotation device 1720 again by 45 degrees in the second rotation direction from $t_4$ to $t_5$.

The processor 110 according to various embodiments may control the transfer unit 1750 to not be moved, i.e., to be stopped, in response to the start of the rotation of the rotation device 1720 again in the second rotation direction. Referring to the graph of the transfer unit 1750 among the graphs 1900, the processor 110 may control the transfer unit 1750 not to be moved from $t_4$ to $t_5$.

The processor 110 according to various embodiments may control all of the plurality of light sources 1731, 1733, 1735 and 1737 not to emit X-rays to the subject during the rotation of the rotation device 1720 again in the second rotation direction. Referring to the graphs of the first light source 1731, the second light source 1733, the third light source 1735, and the fourth light source 1737, the processor 110 may control all of the first light source 1731, the second light source 1733, the third light source 1735, and the fourth light source 1737 not to emit X-rays from $t_4$ to $t_5$.

The processor 110 according to various embodiments may repeatedly perform rotating of the rotation device 1720 in the first rotation direction and rotating of the rotation device 1720 in the second rotation direction two times from $t_5$ to $t_9$. The processor 110 may emit X-rays to the subject using the third light source 1735 among the plurality of light sources during the rotation of the rotation device 1720 in the first rotation direction from $t_5$ to $t_6$. The processor 110 may emit X-rays to the subject using the fourth light source 1737 among the plurality of light sources during the rotation of the rotation device 1720 in the first rotation direction from $t_7$ to $t_8$.

The processor 110 may create at least one raw image of the subject through the above operations and create a helical CT image of the subject based on the at least one raw image.

Figure 20:
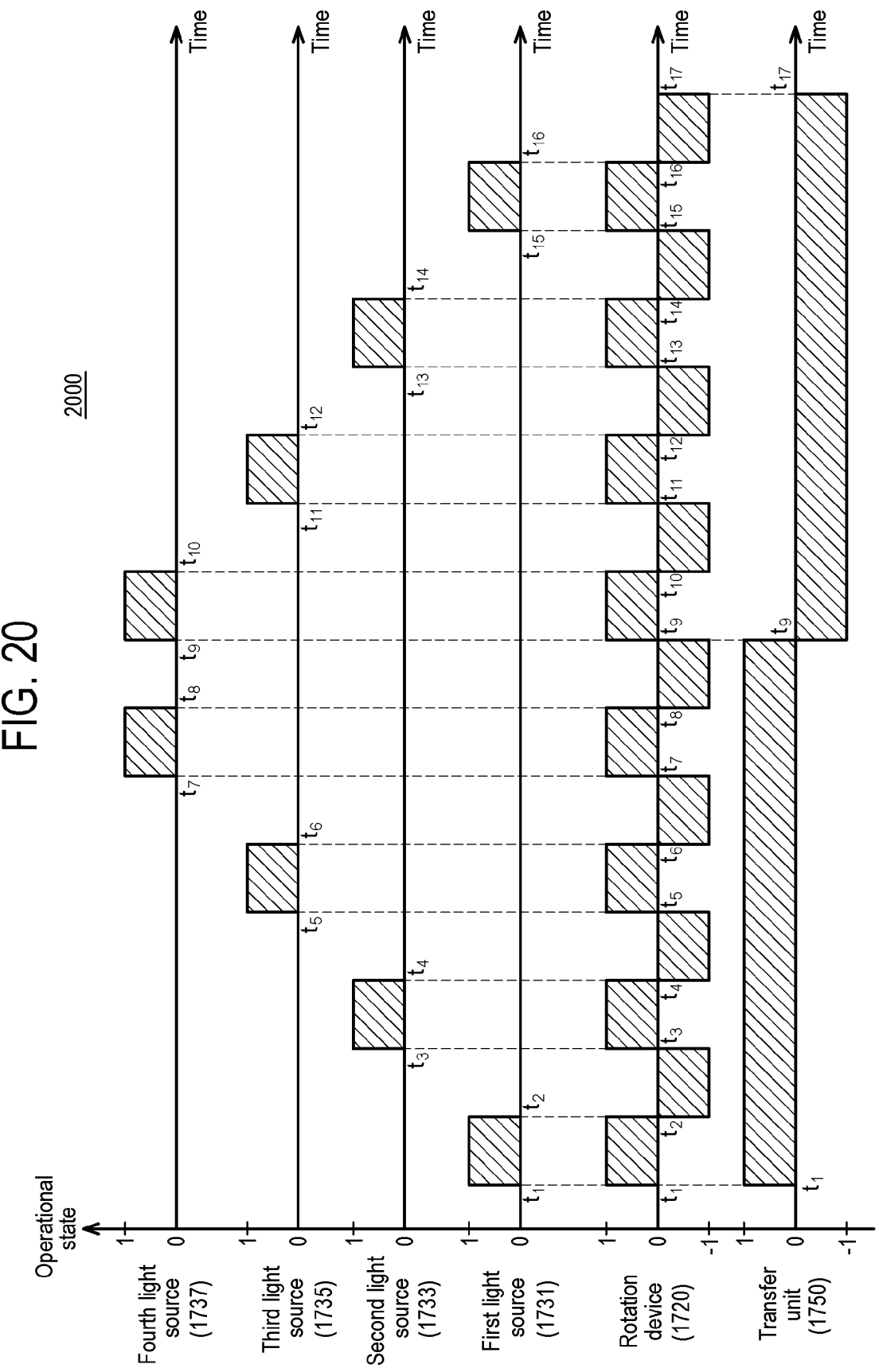
FIG. 20 is a graph showing a CT method performed by the CT apparatus according to the fourth embodiment.

FIG. 20 is a graph showing a CT method performed by the CT apparatus 100 according to the fourth embodiment. Specifically, FIG. 20 is a graph showing operational states of the plurality of light sources 1731, 1733, 1735 and 1737, the rotation device 1720, and the transfer unit 1750 over time when the total number of the plurality of light sources 1731, 1733, 1735 and 1737 is four.

The CT apparatus 100 according to various embodiments may obtain helical CT images of a subject by an operating method shown in graphs 1300 and create a 3D image of the entire subject using the obtained helical CT images. A description of parts of FIG. 20 that are the same as those of FIG. 19 is omitted here.

According to various embodiments, operational states of the rotation device 1720, the first light source 1731, the second light source 1733, the third light source 1735, and the fourth light source 1737 from $t_1$ to $t_9$ are the same as the above states described with reference to FIG. 19. Referring to graphs of the rotation device 1720, the first light source 1731, the second light source 1733, the third light source 1735 and the fourth light source 1737 among the graphs 2000, the processor 110 may control the rotation device 1720 to be repeatedly rotated by a determined angle of rotation in a first rotation direction and thereafter rotated in a second rotation direction. The processor 110 may emit X-rays to the subject using one of the plurality of light sources 1731, 1733, 1735 and 1737 during the rotation of the rotation device 1720 in the first rotation direction. For example, as shown in the graphs 2000, the processor 110 may control the plurality of light sources 1731, 1733, 1735 and 1737 to emit X-rays to the subject sequentially from the first light source 1731, the second light source 1733, the third light source 1735, and the fourth light source 1737.

According to various embodiments, referring to the graph of the transfer unit 1750 among the graphs 2000, the processor 110 may control the transfer unit 1750 to be moved constantly at a predetermined speed in a positive direction of an axis of rotation from $t_1$ to $t_9$. Some data of helical CT images of the subject may be lost when the transfer unit 1750 is not stopped during the rotation of the rotation device 1720 in the second rotation direction, i.e., during restoration of the rotation device 1720 to an original position. To supplement the lost data, the processor 110 may move the transfer unit 1750 again at the predetermined speed in a negative direction of the axis of rotation. For example, the processor 110 may control the transfer unit 1750 to be moved constantly at a predetermined speed in the negative direction of the axis of rotation from $t_9$ to $t_{17}$.

Referring to the graphs of the rotation device 1720, the first light source 1731, the second light source 1733, the third light source 1735, and the fourth light source 1737 among the graphs 2000, the processor 110 may control the rotation device 1720 to be repeatedly rotated by a determined angle of rotation in the first rotation direction and thereafter rotated in the second rotation direction from $t_9$ to $t_{17}$. The processor 110 may emit X-rays to the subject using one of the plurality of light sources 1731, 1733, 1735 and 1737 during the rotation of the rotation device 1720 in the first rotation direction. For example, as shown in the graphs 2000, the processor 110 may control the plurality of light sources 1731, 1733, 1735 and 1737 to emit X-rays to the subject sequentially from the fourth light source 1737, the third light source 1735, the second light source 1733, and the first light source 1731 from $t_9$ to $t_{17}$.

The processor 110 may create at least one raw image of the subject through the above operations and create a helical CT image of the subject based on the at least one raw image.

Figure 21:
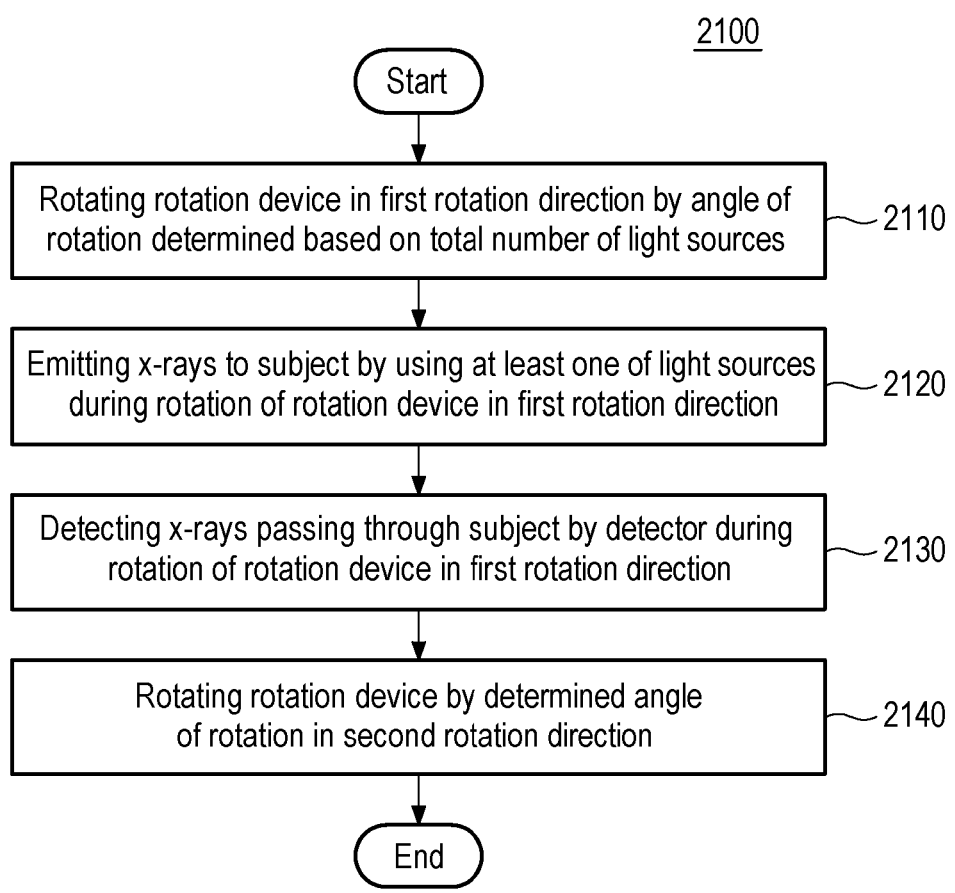
FIG. 21 is a flowchart of operations of the CT apparatus according to the fourth embodiment.

FIG. 21 is a flowchart 2100 of operations of the CT apparatus 100 according to the fourth embodiment.

Referring to the flowchart 2100, in operation 2110, the processor 110 of the CT apparatus 100 according to various embodiments may rotate the rotation device 1720 in a first rotation direction by an angle of rotation determined based on the total number of the plurality of light sources 1731, 1733, 1735 and 1737.

In operation 2120, the processor 110 according to various embodiments may emit X-rays to a subject by using at least one of the plurality of light sources 1731, 1733, 1735 and 1737 during the rotation of the rotation device 1720 in the first rotation direction.

In operation 2130, the processor 110 according to various embodiments may detect X-rays passing through the subject by the detector 1740 during the rotation of the rotation device 1720 in the first rotation direction. The processor 110 may create at least one raw image of the subject based on the X-rays detected by the detector 1740. The processor 110 may create a 3D image of the subject using the at least one raw image of the subject.

In operation 2140, the processor 110 according to various embodiments may rotate the rotation device 1720 by the determined angle of rotation in a second rotation direction. The processor 110 according to various embodiments may control all of the plurality of light sources 1731, 1733, 1735 and 1737 not to emit X-rays to the subject during the rotation of the rotation device 1720 by the determined angle of rotation in the second rotation direction.

Fifth Embodiment

FIGS. 22 to 26 are diagrams for describing a CT apparatus 100 according to a fifth embodiment and a CT method using the same. A description of parts of the fifth embodiment that are the same as those of the other embodiments is omitted here.

Figure 22:
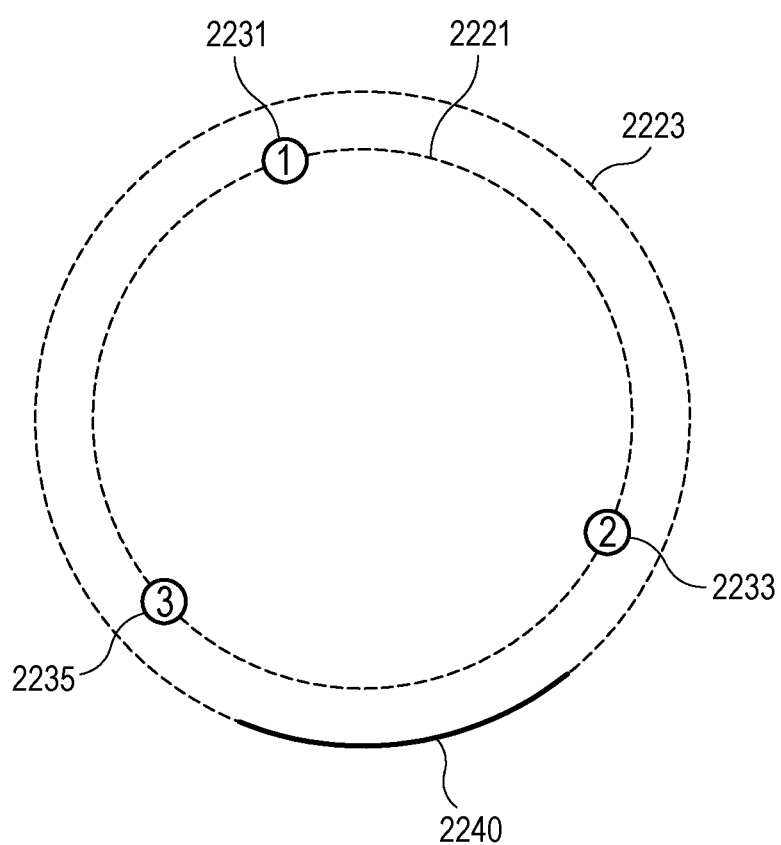
FIG. 22 is a cross-sectional view of an x-y plane of a gantry of a CT apparatus according to a fifth embodiment.

FIG. 22 is a cross-sectional view of an x-y plane of a gantry of the CT apparatus 100 according to the fifth embodiment.

Referring to FIG. 22, the CT apparatus 100 according to various embodiments may include a gantry, a plurality of light sources 2231, 2233 and 2235 and a detector 2240. The gantry may include a first rotation device 2221 and a second rotation device 2223 that have a ring shape, share an axis of rotation, and are rotatable independently of each other. The plurality of light sources 2231, 2233 and 2235 may be arranged on the first rotation device 2221 at regular intervals. The plurality of light sources 2231, 2233, and 2235 may emit X-rays to a subject loaded on a transfer unit 2250. Although in this drawing, it is assumed for convenience of description that a total number of the plurality of light sources 2231, 2233 and 2235 is three, the total number of the plurality of light sources 2231, 2233 and 2235 is not limited to three and may be two or greater than three.

The detector 2240 according to various embodiments may be disposed in one area of the second rotation device 2223 and detect X-rays passing through the subject. An initial position of the second rotation device 2223 may be set to a position facing and corresponding to a light source set to first emit X-rays among the plurality of light sources 2231, 2233 and 2235. For example, when the first light source 2231 among the plurality of light sources 2231, 2233 and 2235 is set to first emit X-rays at an initial stage, the processor 110 may set a position at which the detector 2240 faces and corresponds to the first light source 2231 to an initial position of the second rotation device 2223.

Figure 23:
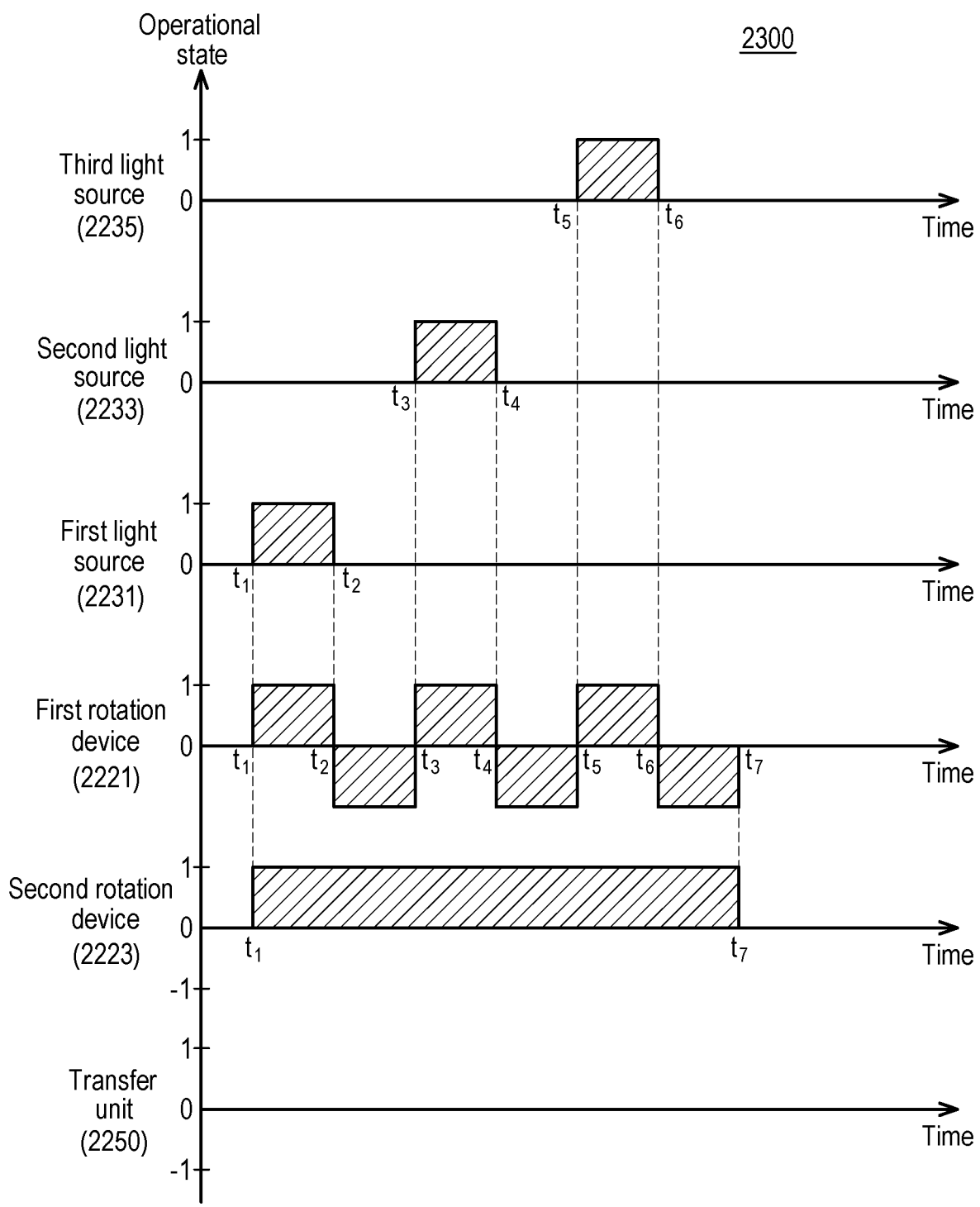
FIG. 23 is a graph showing a CT method performed by the CT apparatus according to the fifth embodiment.

FIG. 23 is a graph showing a CT method performed by the CT apparatus 100 according to the fifth embodiment. Specifically, FIG. 23 is a graph showing operational states of the plurality of light sources 2231, 2233 and 2235, the first rotation device 2221, the second rotation device 2223, and the transfer unit 2250 over time when the total number of the plurality of light sources 2231, 2233 and 2235 is three.

In the graphs of the first rotation device 2221 and the second rotation device 2223 among graphs 2300, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 2231, the second light source 2233, and the third light source 2235 among the graphs 2300, an operational state 1 may represent a state in which X-rays are emitted and an operational state 0 may represent a state in which X-rays are not emitted. In the graph of the transfer unit 2250 among the graphs 2300, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain circular CT images of a subject by an operation method shown in the graphs 2300.

The processor 110 according to various embodiments may control the first rotation device 2221 to repeatedly perform a first operation of being rotated in the first rotation direction by an angle of rotation determined based on the total number of the plurality of light sources 2231, 2233 and 2235 and a second operation of being rotated by the determined angle of rotation in the second rotation direction. For example, when the total number of the plurality of light sources 2231, 2233 and 2235 is three, the processor 110 may determine the angle of rotation of the first rotation device 2221 to be 120 degrees. The processor 110 may determine a number of times the first operation and the second operation are repeatedly performed by the first rotation device 2221 based on the total number of the plurality of light sources. For example, when the total number of the plurality of light sources 2231, 2233 and 2235 is three, the processor 110 may determine the number of times the first operation and the second operation are repeatedly performed by the first rotation device 2221 to be three.

Referring to the graph of the transfer unit 2250 among the graphs 2300, the processor 110 according to various embodiments may not move the transfer unit 2250 to obtain a circular CT image of the subject.

The processor 110 according to various embodiments may control the second rotation device 2223 to be rotated in the first rotation direction at the same speed of rotation as the first rotation device 2221 while the first and second operations are repeatedly performed by the first rotation device 2221. Referring to the graph of the second rotation device 2223 among the graphs 2300, the second rotation device 2223 may be rotated in the first rotation direction from $t_1$ to $t_7$. For example, the processor 110 may rotate the second rotation device 2223 in the first rotation direction at the same speed of rotation as the first rotation device 2221.

The processor 110 according to various embodiments may emit X-rays to the subject by using at least one of the plurality of light sources 2231, 2233 and 2235 during the rotation of the first rotation device 2221 in the first rotation direction. The processor 110 may emit X-rays to the subject using the first light source 2231 during the rotation of the first light source 2231 in the first rotation direction from $t_1$ to $t_2$. In this case, the second light source 2233 and the third light source 2235 may not emit X-rays. The processor 110 may detect X-rays passing through the subject using the detector 2240 disposed at a position facing and corresponding to the first light source 2231 during the emission of the X-rays from the first light source 2231. The processor 110 may create at least one raw image of the subject based on the X-rays detected by the detector 2240. As described above, the processor 110 may emit X-rays to the subject using the second light source 2233 from $t_3$ to $t_4$ and emit X-rays to the subject using the third light source 2235 from $t_5$ to $t_6$.

The processor 110 according to various embodiments may rotate the first rotation device 2221 in the second rotation direction. The processor 110 may control the first rotation device 2221 to be rotated by a determined angle of rotation in the second rotation direction after the rotation of the first rotation device 2221 by the determined angle of rotation in the first rotation direction. Referring to the graph of the first rotation device 2221 among the graphs 2300, the processor 110 may rotate the first rotation device 2221 by 120 degrees in the second rotation direction from $t_2$ to $t_3$. That is, the processor 110 may return the first rotation device 2221 to an original position before the rotation of the first rotation device 2221 in the first rotation direction. As described above, the processor 110 may rotate the first rotation device 2221 by 120 degrees in the second rotation direction from $t_4$ to $t_5$ and rotate the first rotation device 2221 by 120 degrees in the second rotation direction from $t_6$ to $t_7$.

The processor 110 may create at least one raw image of the subject through the above operations and create a circular CT image of the subject based on the at least one raw image.

Figure 24:
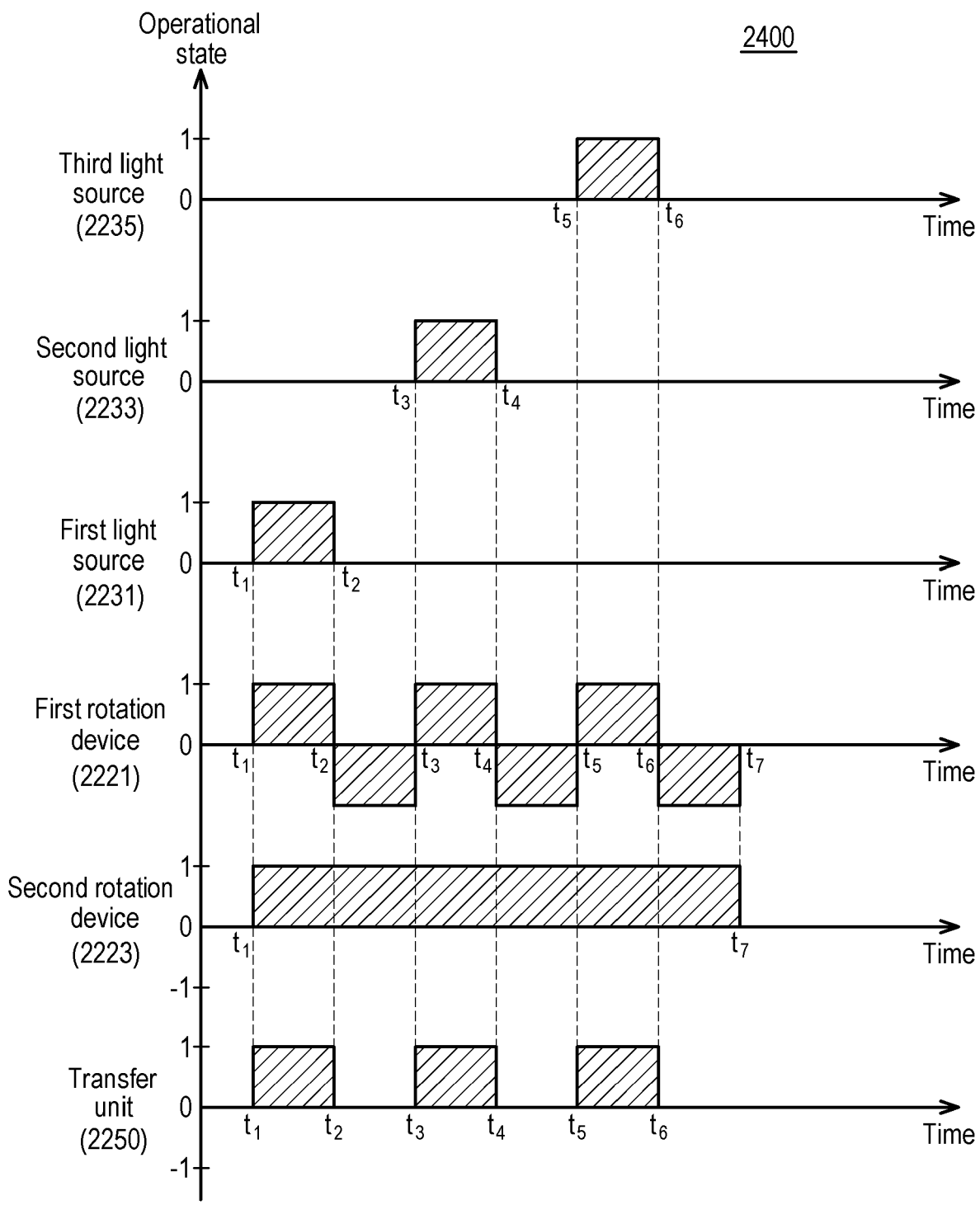
FIG. 24 is a graph showing a CT method performed by the CT apparatus according to the fifth embodiment.

FIG. 24 is a graph showing a CT method performed by the CT apparatus 100 according to the fifth embodiment. Specifically, FIG. 24 is a graph showing operational states of the plurality of light sources 2231, 2233 and 2235, the first rotation device 2221, the second rotation device 2223, and the transfer unit 2250 over time when the total number of the plurality of light sources 2231, 2233 and 2235 is three.

The CT apparatus 100 according to various embodiments may obtain helical CT images of a subject by an operating method shown in graphs 2400 and create a 3D image of the entire subject using the obtained helical CT images. A description of parts of FIG. 24 that are the same as those of FIG. 23 is omitted here.

According to an embodiment, operational states of the first rotation device 2221, the second rotation device 2223, the first light source 2231, the second light source 2233, and the third light source 2235 from $t_1$ to $t_7$ are the same as the above states described with reference to FIG. 23. Referring to graphs of the first rotation device 2221, the second rotation device 2223, the first light source 2231, the second light source 2233, and the third light source 2235 among the graphs 2400, the processor 110 may control the first rotation device 2221 to be repeatedly rotated by a determined angle of rotation in a first rotation direction and thereafter rotated in a second rotation direction. The processor 110 may control the second rotation device 2223 to be rotated at the same speed of rotation as the first rotation device 2221 while the first rotation device 2221 repeatedly performs the above operations. The processor 110 according to various embodiments may emit X-rays to the subject by using one of the plurality of light sources 2231, 2233 and 2235 during the rotation of the first rotation device 2221 in the first rotation direction. For example, as shown in the graphs 2400, the processor 110 may control the plurality of light sources 2231, 2233 and 2235 to emit X-rays to the subject sequentially from the first light source 2231, the second light source 2233, and the third light source 2235.

The processor 110 according to various embodiments may control the transfer unit 2250 to be moved by a predetermined distance in a positive direction of an axis of rotation during the rotation of the first rotation device 2221 in the first rotation direction. Referring to the graph of the transfer unit 2250 among the graphs 2400, the processor 110 may move the transfer unit 2250 by the predetermined distance from $t_1$ to $t_2$, from $t_3$ to $t_4$, and from $t_5$ to $t_6$.

The processor 110 may create at least one raw image of the subject through the above operations and create a helical CT image of the subject based on the at least one raw image. When the method shown in the graphs 2400 is used, the transfer unit 2250 is moved only during emission of X-rays by using one of the plurality of light sources 2231, 2233 and 2235 and thus helical CT images of the subject may be obtained.

Figure 25:
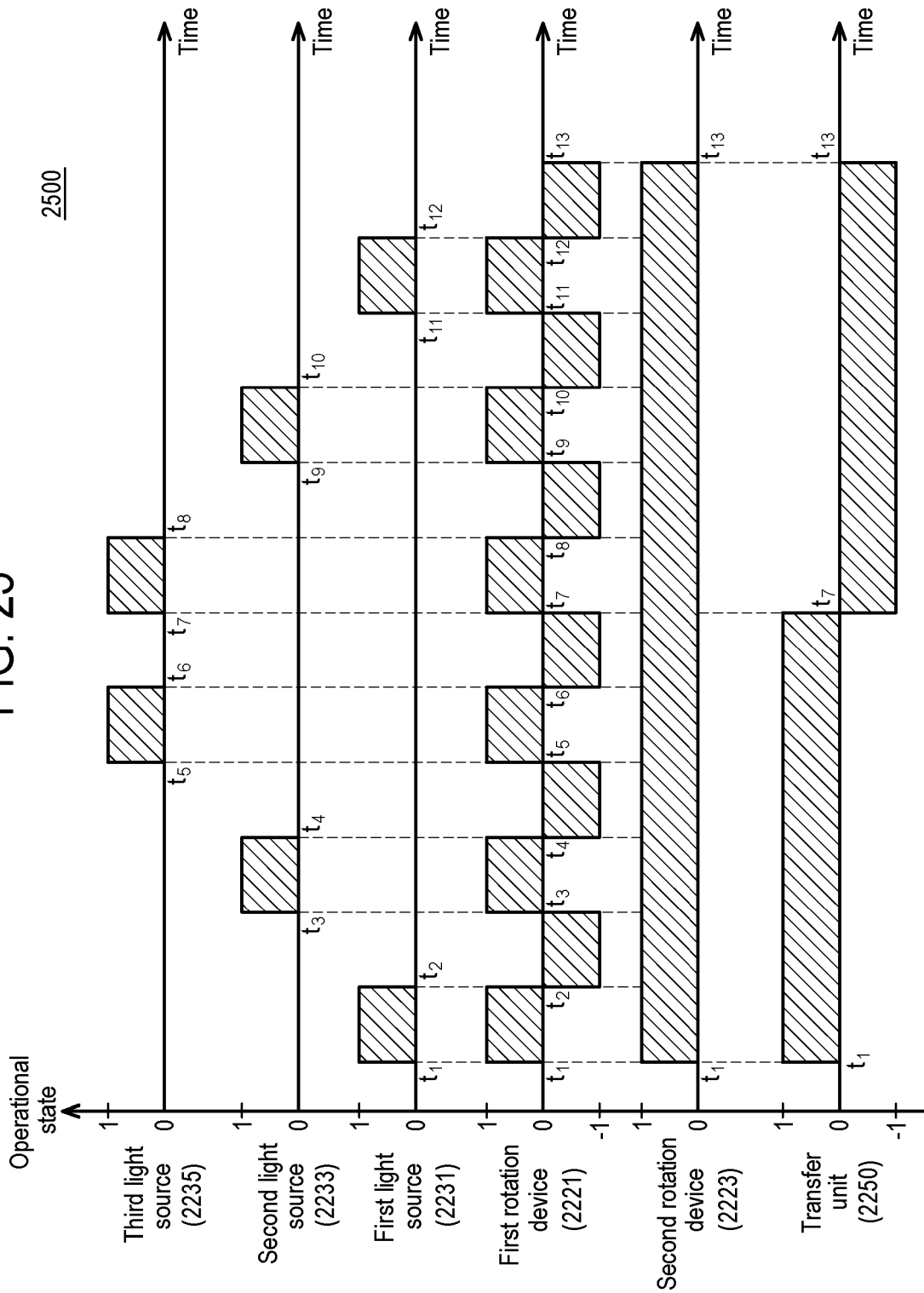
FIG. 25 is a graph showing a CT method performed by the CT apparatus according to the fifth embodiment.

FIG. 25 is a graph showing a CT method performed by the CT apparatus 100 according to the fifth embodiment. Specifically, FIG. 25 is a graph showing operational states of the plurality of light sources 2231, 2233 and 2235, the first rotation device 2221, the second rotation device 2223, and the transfer unit 2250 over time when the total number of the plurality of light sources 2231, 2233 and 2235 is three.

The CT apparatus 100 according to various embodiments may obtain helical CT images of a subject by an operating method shown in graphs 2500 and create a 3D image of the entire subject using the obtained helical CT images. A description of parts of FIG. 25 that are the same as those of FIG. 24 is omitted here.

According to various embodiments, operational states of the first rotation device 2221, the second rotation device 2223, the first light source 2231, the second light source 2233, and the third light source 2235 from $t_1$ to $t_7$ are the same as the above states described with reference to FIG. 24. Referring to the graphs of the first rotation device 2221, the second rotation device 2223, the first light source 2231, the second light source 2233, and the third light source 2235 among the graphs 2500, the processor 110 may control the first rotation device 2221 to be repeatedly rotated by a determined angle of rotation in a first rotation direction and thereafter rotated in a second rotation direction. The processor 110 may emit X-rays to the subject using one of the plurality of light sources 2231, 2233 and 2235 during the rotation of the first rotation device 2221 in the first rotation direction. For example, as shown in the graphs 2500, the processor 110 may control the plurality of light sources 2231, 2233 and 2235 to emit X-rays to the subject sequentially from the first light source 2231, the second light source 2233, and the third light source 2235.

The processor 110 according to various embodiments may control the second rotation device 2223 to be rotated at the same speed of rotation as the first rotation device 2221 in the first rotation direction while the first rotation device 2221 is repeatedly rotated by the determined angle of rotation in the first rotation direction and thereafter rotated in the second rotation direction. Referring to the graph of the second rotation device 2223 among the graphs 2500, the processor 110 may rotate the second rotation device 2223 in the first rotation direction from $t_1$ to $t_{13}$.

According to various embodiments, referring to the graph of the transfer unit 2250 among the graphs 2500, the processor 110 may control the transfer unit 2250 to be moved constantly at a predetermined speed in a positive direction of an axis of rotation from $t_1$ to $t_7$. Some data of helical CT images of the subject may be lost when the transfer unit 2250 is not stopped during the rotation of the first rotation device 2221 in the second rotation direction, i.e., during restoration of the first rotation device 2221 to an original position. To supplement the lost data, the processor 110 may move the transfer unit 2250 again at the predetermined speed in a negative direction of the axis of rotation. For example, the processor 110 may move the transfer unit 2250 to be moved constantly at the predetermined speed in the negative direction of the axis of rotation from $t_7$ to $t_{13}$.

Referring to the graphs of the first rotation device 2221, the second rotation device 2223, the first light source 2231, the second light source 2233, and the third light source 2235 among the graphs 2500, the processor 110 may control the first rotation device 2221 to be repeatedly rotated by the determined angle of rotation in the first rotation direction and thereafter rotated in the second rotation direction from $t_7$ to $t_{13}$. The processor 110 may emit X-rays to the subject using one of the plurality of light sources 2231, 2233 and 2235 during the rotation of the first rotation device 2221 in the first rotation direction. For example, as shown in the graphs 2500, the processor 110 may control the plurality of light sources 2231, 2233 and 2235 to emit X-rays to the subject sequentially from the third light source 2235, the second light source 2233, and the first light source 2231 from $t_7$ to $t_{13}$.

The processor 110 may create at least one raw image of the subject through the above operations and create a helical CT image of the subject based on the at least one raw image.

FIG. 26 is a flowchart 2600 of operations of the CT apparatus 100 according to the fifth embodiment.

Referring to the flowchart 2600, in operation 2610, the processor 110 of the CT apparatus 100 according to various embodiments may control the first rotation device 2221 to repeatedly perform a first operation of being rotated in the first rotation direction by an angle of rotation determined based on the total number of the plurality of light sources 2231, 2233 and 2235 and a second operation of being rotated by the determined angle of rotation in the second rotation direction. The processor 110 may determine a number of times the first operation and the second operation are repeatedly performed by the first rotation device 2221, for example, based on the total number of the plurality of light sources 2231, 2233 and 2235.

In operation 2620, the processor 110 according to various embodiments may control the second rotation device 2223 to be rotated in the first rotation direction at the same speed of rotation as the first rotation device 2221 while the first and second operations are repeatedly performed by the first rotation device 2221.

In operation 2630, the processor 110 according to various embodiments may emit X-rays to a subject by using one of the plurality of light sources 2231, 2233 and 2235 and detect X-rays passing through the subject by the detector 2240 during the performance of the first operation by the first rotation device 2221. The processor 110 may create at least one raw image of the subject based on the X-rays detected by the detector 2240. The processor 110 may create a 3D image of the subject using the at least one raw image of the subject.

Sixth Embodiment

FIGS. 27A to 30 are diagrams for describing a CT apparatus 100 according to a sixth embodiment and a CT method using the same. A description of parts of the fifth embodiment that are the same as those of the other embodiments is omitted here.

Figure 27A:
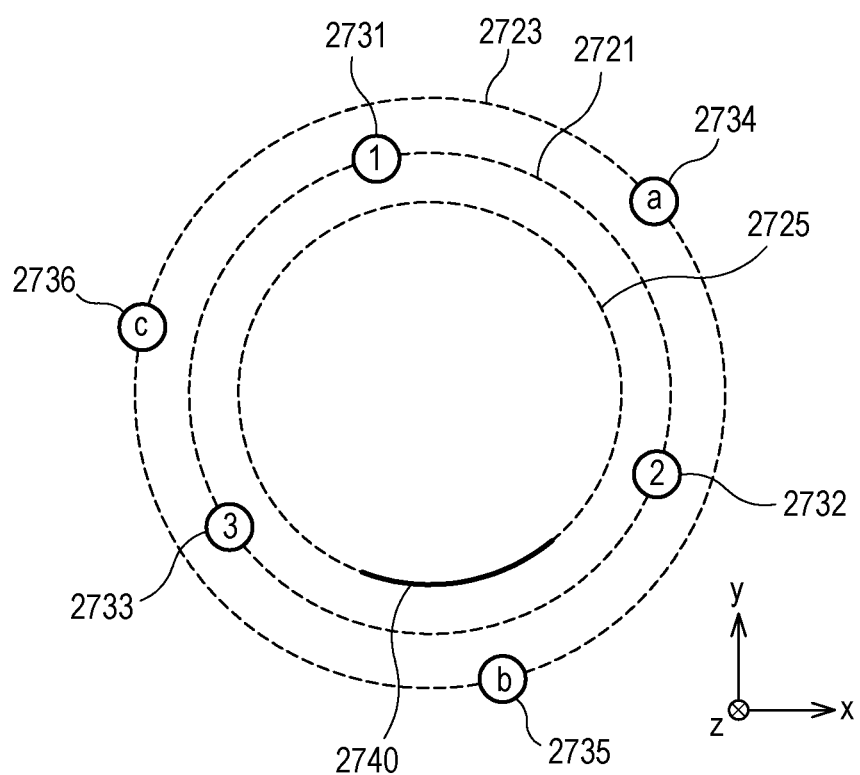
FIG. 27A is a cross-sectional view of an x-y plane of a gantry of a CT apparatus according to a sixth embodiment.
Figure 27B:
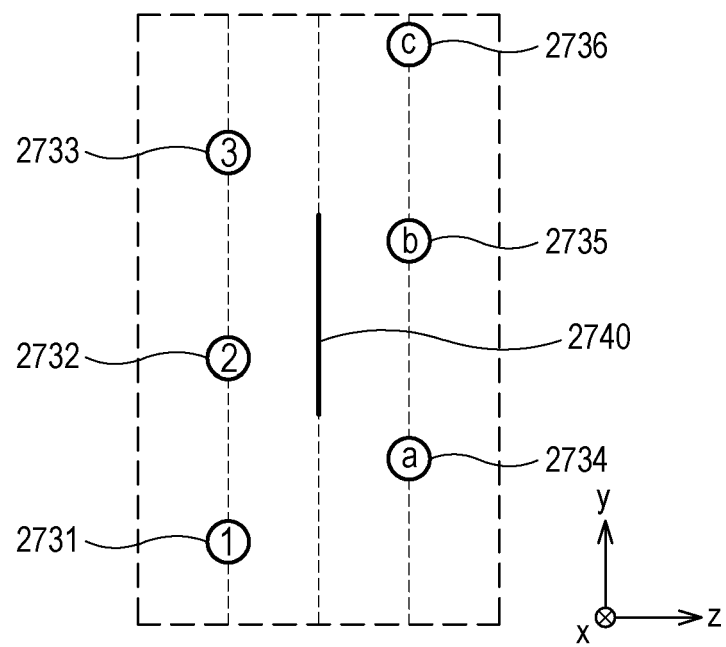
FIG. 27B is a cross-sectional view of a y-z plane of the gantry according to the sixth embodiment.

FIG. 27A is a cross-sectional view of an x-y plane of a gantry of the CT apparatus 100 according to the sixth embodiment, and FIG. 27B is a cross-sectional view of a y-z plane of the gantry according to the sixth embodiment.

Referring to FIG. 27A, the CT apparatus 100 according to various embodiments may include a gantry, a plurality of first light sources 2731, 2732 and 2733, a plurality of second light sources 2734, 2735 and 2736, and a detector 2740. The gantry may include a first rotation device 2721, a second rotation device 2723 and a third rotation device 2725 that have a ring shape, share an axis of rotation, and are rotatable independently of one another. The plurality of first light sources 2731, 2732 and 2733 may be arranged on the first rotation device 2721 at regular intervals. The plurality of second light sources 2734, 2735 and 2736 may be arranged on the second rotation device 2723 at regular intervals. The plurality of first light sources 2731, 2732 and 2733 and the plurality of second light sources 2734, 2735 and 2736 may emit X-rays to a subject loaded on the transfer unit 2750. In this drawing, it is assumed for convenience of description that the total number of the plurality of first light sources is three and the total number of the plurality of second light sources is three, but the light sources are not limited thereto.

The detector 2740 according to various embodiments may be provided in one area of the third rotation device 2725 and detect X-rays passing through the subject. An initial position of the third rotation device 2725 may be set to a position at which the detector 2740 may face and correspond to a light source set to first emit X-rays among the plurality of first light sources 2731, 2732 and 2733 and the plurality of second light sources 2734, 2735 and 2736. For example, when the first light source 2731 is set to first emit X-rays at an initial stage, the processor 110 may set a position at which the detector 2740 may face and correspond to the first light source 2731 to an initial position of the third rotation device 2725.

Referring to FIG. 27B, a layout plan of the first rotation device 2721, a layout plan of the second rotation device 2723, and a layout plan of the third rotation device 2725 may be provided to be parallel to one another. For example, positions of the plurality of first light sources 2731, 2732 and 2733 on a z-axis may be different from those of the plurality of second light sources 2734, 2735 and 2736 on the z-axis. For example, the positions of the first light source 2731, the second light source 2732, and the third light source 2733 on the z-axis may be different from those of the second light source 2734, the $b^{th}$ light source 2735, and the $c^{th}$ light source 2736 on the z-axis.

Figure 28:
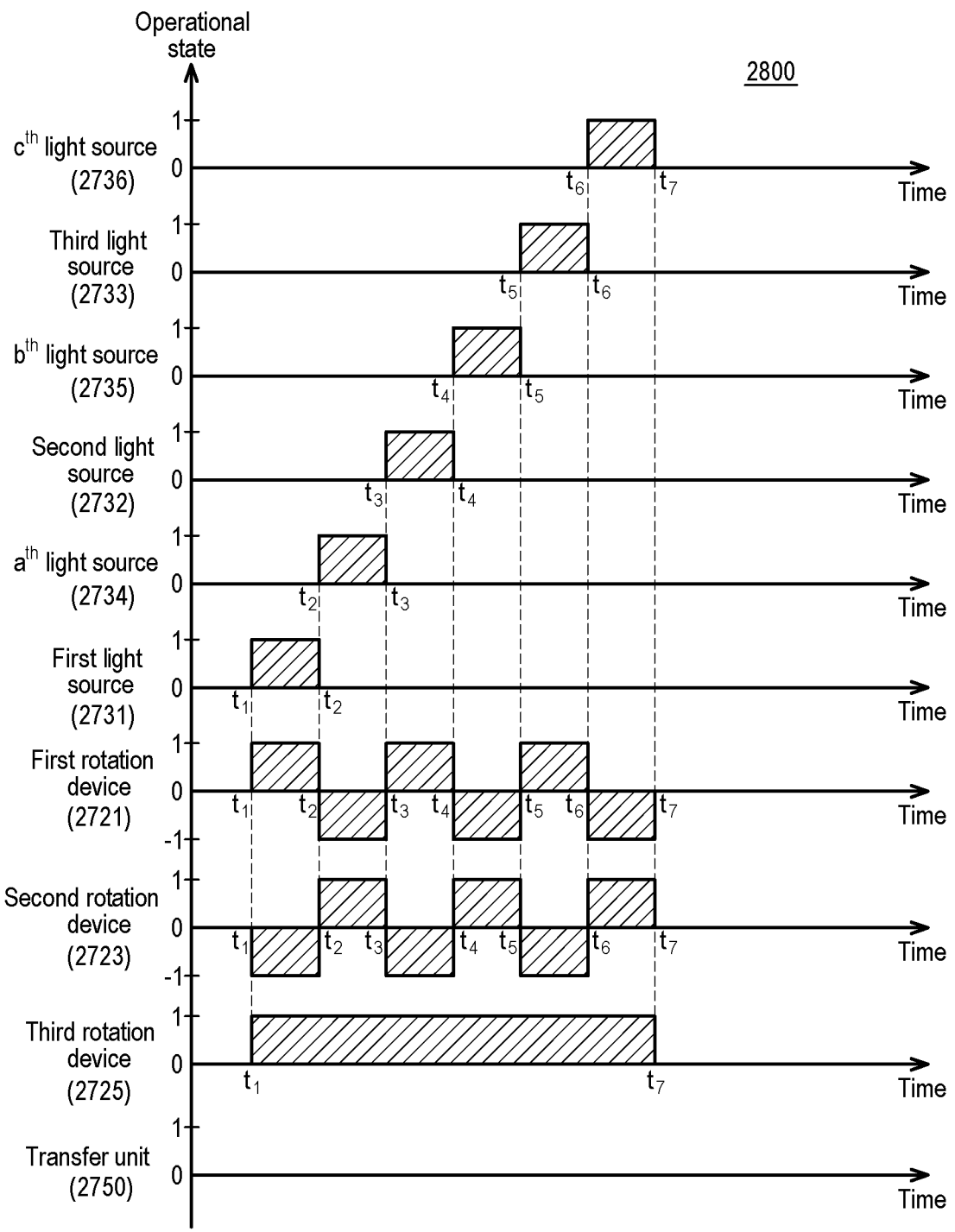
FIG. 28 is a graph showing a CT method performed by the CT apparatus according to the sixth embodiment.

FIG. 28 is a graph showing a CT method performed by the CT apparatus 100 according to the sixth embodiment. Specifically, FIG. 28 is a graph showing operational states of the plurality of first light sources 2731, 2732 and 2733, the plurality of second light sources 2734, 2735 and 2736, the first rotation device 2721, the second rotation device 2723, the third rotation device 2725, and the transfer unit 2750 over time when the total number of the plurality of first light sources 2731, 2732 and 2733 and the total number of the plurality of second light sources 2734, 2735 and 2736 are each three.

In the graphs of the first rotation device 2721, the second rotation device 2723 and the third rotation device 2725 among the graphs 2800, an operational state 1 may represent a state of rotation in a first rotation direction, an operational state 0 may represent a state of non-rotation, and an operational state −1 may represent a state of rotation in a second rotation direction opposite to the first rotation direction. In the graphs of the first light source 2731, the second light source 2732, the third light source 2733, the second light source 2734, the $b^{th}$ light source 2735, and the $c^{th}$ light source 2736 among the graphs 2800, an operational state 1 may represent a state in which X-rays are emitted and an operational state 0 may represent a state in which X-rays are not emitted. In the graph of the transfer unit 2750 among the graphs 2800, an operational state 1 may represent a state of movement in a positive (+) direction of an axis of rotation, and an operational state −1 may represent a state of movement in a negative (−) direction of the axis of rotation.

The CT apparatus 100 according to various embodiments may obtain circular CT images of a subject by an operation method shown in the graphs 2800.

According to various embodiments, the processor 110 may control the first rotation device 2721 to repeatedly perform a first operation of being rotated in the first direction by an angle of rotation determined by the total number of the plurality of first light sources 2731, 2732 and 2733 and the total number of the plurality of second light sources 2734, 2735 and 2736 and a second operation of being rotated by the determined angle of rotation in the second rotation direction. The processor 110 may determine a value obtained by dividing 360 degrees by the total number of the plurality of first light sources 2731, 2732 and 2733 and the total number of the plurality of second light sources 2734, 2735 and 2736 as an angle of rotation of the first rotation device 2721, For example, when the total number of the plurality of first light sources 2731, 2732 and 2733 and the total number of the second light sources 2734, 2735 and 2736 are each three, the processor 110 may determine an angle of rotation of the first rotation device 2721 to be 60 degrees.

According to various embodiments, the processor 110 may determine a number of times the first operation and the second operation are repeatedly performed by the first rotation device 2721 based on the total number of the plurality of first light sources 2731, 2732 and 2733 and the total number of the plurality of second light sources 2734, 2735 and 2736. For example, when the total number of the plurality of first light sources 2731, 2732 and 2733 and the total number of the plurality of second light sources 2734, 2735 and 2736 are each three, the processor 110 may determine a number of times the first operation and the second operation are repeatedly performed by the first rotation device 2721 to be three.

The processor 110 according to various embodiments may control the second rotation device 2723 to repeatedly perform a third operation of being rotated by the determined angle of rotation in the second rotation direction and a fourth operation of being rotated by the determined angle of rotation in the first rotation direction. The processor 110 may control the second rotation device 2723 to be rotated at the same speed of rotation as the first rotation device 2721.

According to various embodiments, the first operation of the first rotation device 2721 and the third operation of the second rotation device 2723 may be performed simultaneously, and the second operation of the first rotation device 2721 and the fourth operation of the second rotation device 2723 may be performed simultaneously. That is, the first rotation device 2721 and the second rotation device 2723 may be rotated in different directions. For example, the processor 110 may rotate the second rotation device 2723 in the second rotation direction during the rotation of the first rotation device 2721 in the first rotation direction and rotate the second rotation device 2723 in the first rotation direction during the rotation of the first rotation device 2721 in the second rotation direction.

The processor 110 according to various embodiments may control the third rotation device 2725 to be rotated in the first rotation direction at the same speed of rotation as the first rotation device 2721 and the second rotation device 2723 while the first rotation device 2721 repeatedly performs the first operation and the second operation and the second rotation device 2723 repeatedly performs the third operation and the fourth operation. For example, at $t_1$, the detector 2740 may be arranged at a position on the third rotation device 2725 to face and correspond to the first light source 2731, and from $t_1$ to $t_7$, the third rotation device 2725 may be rotated in the first rotation direction at the same speed of rotation as the first rotation device 2721 and the second rotation device 2723. In this case, even when X-rays are emitted in an order of the first light source 2731, the second light source 2734, the second light source 2732, the $b^{th}$ light source 2735, the third light source 2733, and the $c^{th}$ light source 2736, the detector 2740 may be always located at a position facing a light source emitting X-rays. Accordingly, the detector 2740 may detect X-rays passing through the subject from $t_1$ to $t_7$.

Referring to the graph of the transfer unit 2750 among the graphs 2800, the processor 110 according to various embodiments may not move the transfer unit 2750 to obtain a circular CT image of the subject.

The processor 110 according to various embodiments may emit X-rays to the subject by using one of the plurality of first light sources 2731, 2732 and 2733 during the rotation of the first rotation device 2721 in the first rotation direction, i.e., the performance of the first operation by the first rotation device 2721. The processor 110 may emit X-rays to the subject using the first light source 2731 during the rotation of the first rotation device 2721 in the first rotation direction from $t_1$ to $t_2$. In this case, neither the second light source 2732 and the third light source 2733 nor the plurality of second light sources 2734, 2735 and 2736 may emit X-rays. The processor 110 may detect X-rays passing through the subject using the detector 2740 during the emission of the X-rays from the first light source 2731. The processor 110 may create at least one raw image of the subject based on the X-rays detected by the detector 2740. As described above, the processor 110 may emit X-rays to the subject only using the second light source 2732 from $t_3$ to $t_4$ and emit X-rays to the subject only using the third light source 2733 from $t_5$ to $t_6$.

The processor 110 according to various embodiments may emit X-rays to the subject using one of the plurality of second light sources 2734, 2735 and 2736 during the rotation of the second rotation device 2723 in the first rotation direction, i.e., the performance of the fifth operation by the second rotation device 2723. The processor 110 may emit X-rays to the subject using the second light source 2734 during the rotation of the second rotation device 2723 from $t_2$ to $t_3$. In this case, neither the $b^{th}$ light source 2735 and the $eh$ light source 2736 nor the plurality of first light sources 2731, 2732 and 2733 may emit X-rays. The processor 110 may detect X-rays passing through the subject using the detector 2740 during the emission of the X-rays from the $a^{th}$ light source 2734. The processor 110 may create at least one raw image of the subject based on the X-rays detected by the detector 2740. As described above, the processor 110 may emit X-rays to the subject only using the $b^{th}$ light source 2735 from $t_4$ to $t_5$, and emit X-rays to the subject only using the $c^{th}$ light source 2736 from $t_6$ to $t_7$.

The processor 110 may create at least one raw image of the subject through the above operations and create a circular CT image of the subject based on the at least one raw image. When the method shown in the graphs 2800 is used, the second rotation device 2723 may be rotated in the first rotation direction to emit X-rays using the plurality of second light sources 2734, 2735 and 2736 during the rotation of the first rotation device 2721 in the second rotation direction, i.e., restoration of the first rotation device 2721 to an original position before the rotation in the first rotation direction.

Figure 29:
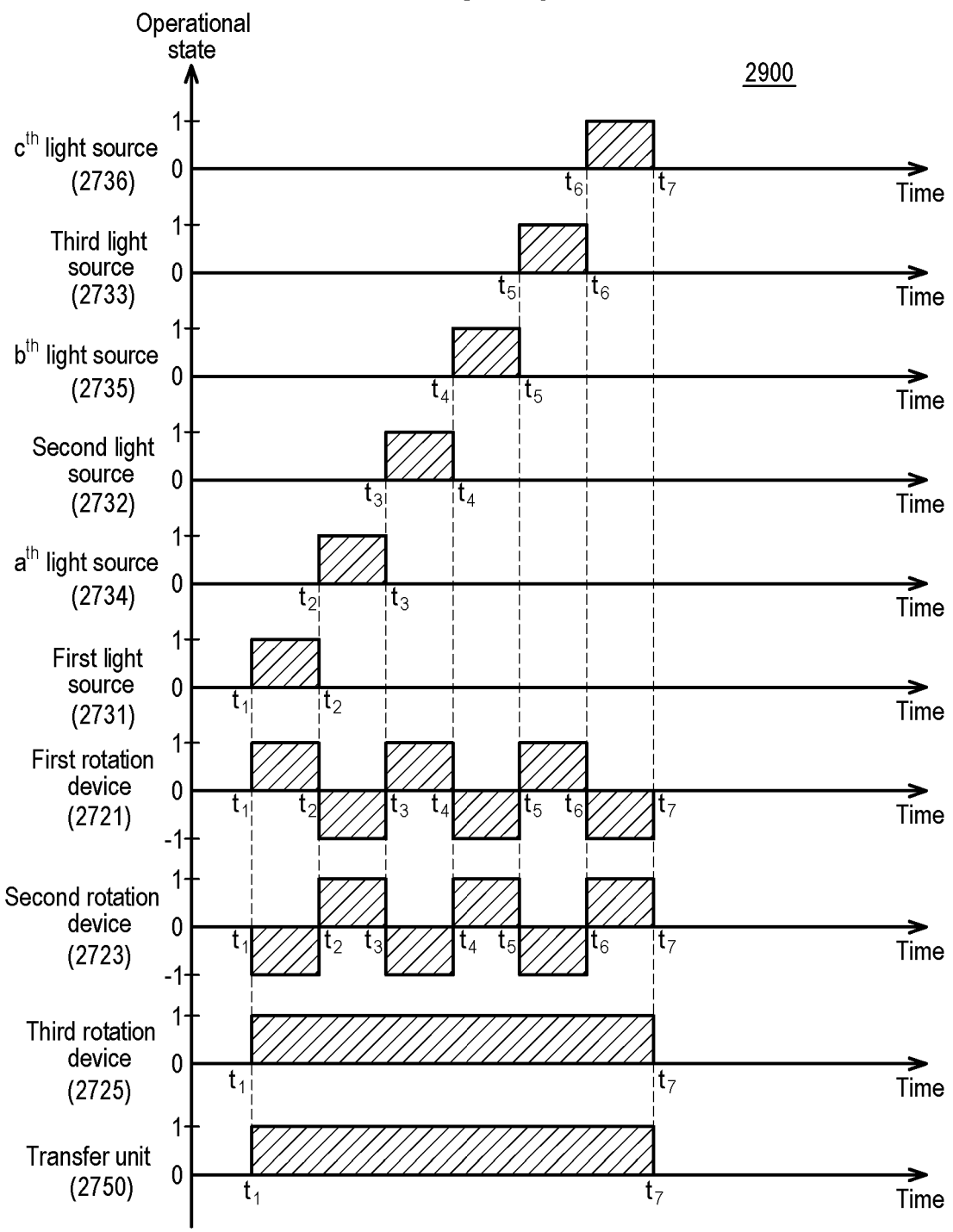
FIG. 29 is a graph showing a CT method performed by the CT apparatus according to the sixth embodiment.

FIG. 29 is a graph showing a CT method performed by the CT apparatus 100 according to the sixth embodiment. Specifically, FIG. 29 is a graph showing operational states of the plurality of first light sources 2731, 2732 and 2733, the plurality of second light sources 2734, 2735 and 2736, the first rotation device 2721, the second rotation device 2723, the third rotation device 2725, and the transfer unit 2750 over time.

The CT apparatus 100 according to various embodiments may obtain helical CT images of a subject by an operating method shown in graphs 2900 and create a 3D image of the entire subject using the obtained helical CT images. A description of parts of FIG. 29 that are the same as those of FIG. 28 is omitted here.

According to various embodiments, operational states of the first rotation device 2721, the second rotation device 2723, the third rotation device 2725, the first light source 2731, the second light source 2732, the third light source 2733, the second light source 2734, the $b^{th}$ light source 2735, and the $c^{th}$ light source 2736 from $t_1$ to $t_7$ are the same as the above states described with reference to FIG. 28. Referring to the graphs of the first rotation device 2721, the second rotation device 2723, the third rotation device 2725, the first light source 2731, the second light source 2732, the third light source 2733, the second light source 2734, the $b^{th}$ light source 2735, and the $c^{th}$ light source 2736 among the graphs 2900, the processor 110 may control the first rotation device 2721 to be repeatedly rotated by a determined angle of rotation in a first rotation direction and rotated in a second rotation direction. The processor 110 may control the second rotation device 2723 to be repeatedly rotated by the determined angle of rotation in the second rotation direction at the same speed of rotation as the first rotation device 2721 and rotated in the first rotation direction while the first rotation device 2721 repeatedly performs the above operations.

According to various embodiments, the processor 110 may emit X-rays to the subject using one of the plurality of first light sources 2731, 2732 and 2733 during the rotation of the first rotation device 2721 in the first rotation direction, and emit X-rays to the subject using one of the plurality of second light sources 2734, 2735 and 2736 during the rotation of the second rotation device 2723 in the first rotation direction. For example, as shown in the graphs 2900, the processor 110 may control the plurality of first light sources 2731, 2732 and 2733 and the plurality of second light sources 2734, 2735 and 2736 to emit X-rays to the subject in the order of the first light source 2731, the $a^{th}$ light source 2734, the second light source 2732, the $b^{th}$ light source 2735, the third light source 2733, and the $c^{th}$ light source 2736.

The processor 110 according to various embodiments may control the transfer unit 2750 to be moved at a predetermined speed in a positive direction of an axis of rotation during the rotation of the first rotation device 2721 and the second rotation device 2723. Referring to the graph of the transfer unit 2750 among the graphs 2900, the processor 110 may move the transfer unit 2750 at the predetermined speed from $t_1$ to $t_7$.

The processor 110 may create at least one raw image of the subject through the above operations and create a helical CT image of the subject based on the at least one raw image.

FIG. 30 is a flowchart 300 of operations of the CT apparatus 100 according to the sixth embodiment.

Referring to the flowchart 300, in operation 3010, the processor 110 of the CT apparatus 100 according to various embodiments may control the first rotation device 2721 to repeatedly perform a first operation of being rotated in a first rotation direction by an angle of rotation determined based on the total number of the plurality of first light sources 2731, 2732 and 2733 and the total number of the plurality of second light sources 2734, 2735 and 2736 and a second operation of being rotated in the second rotation direction by the determined angle of rotation.

In operation 3020, the processor 110 according to various embodiments may control the second rotation device 2723 to repeatedly perform a third operation of being rotated by the determined angle of rotation in the second rotation direction and a fourth operation of being rotated by the determined angle of rotation in the first rotation direction. The first operation of the first rotation device 2721 and the third operation of the second rotation device 2723 may be performed simultaneously, and the second operation of the first rotation device 2721 and the fourth operation of the second rotation device 2723 may be performed simultaneously.

In operation 3030, the processor 110 according to various embodiments may control the third rotation device 2725 to be rotated in the first rotation direction at the same speed of rotation as the first rotation device 2721 and the second rotation device 2723.

In operation 3040, the processor 110 according to various embodiments may emit X-rays to the subject using one of the plurality of first light sources 2731, 2732 and 2733 during the performance of the first operation by the first rotation device 2721, and emit X-rays to the subject using one of the plurality of second light sources 2734, 2735 and 2736 during the performance of the fourth operation by the second rotation device 2723.

In operation 3050, the processor 110 according to various embodiments may detect X-rays passing through the subject by the detector 2740. The processor 110 may create at least one raw image of the subject based on the X-rays detected by the detector 2740. The processor 110 may create a 3D image of the subject using the at least one raw image of the subject.

Other Embodiments

Figure 31A:
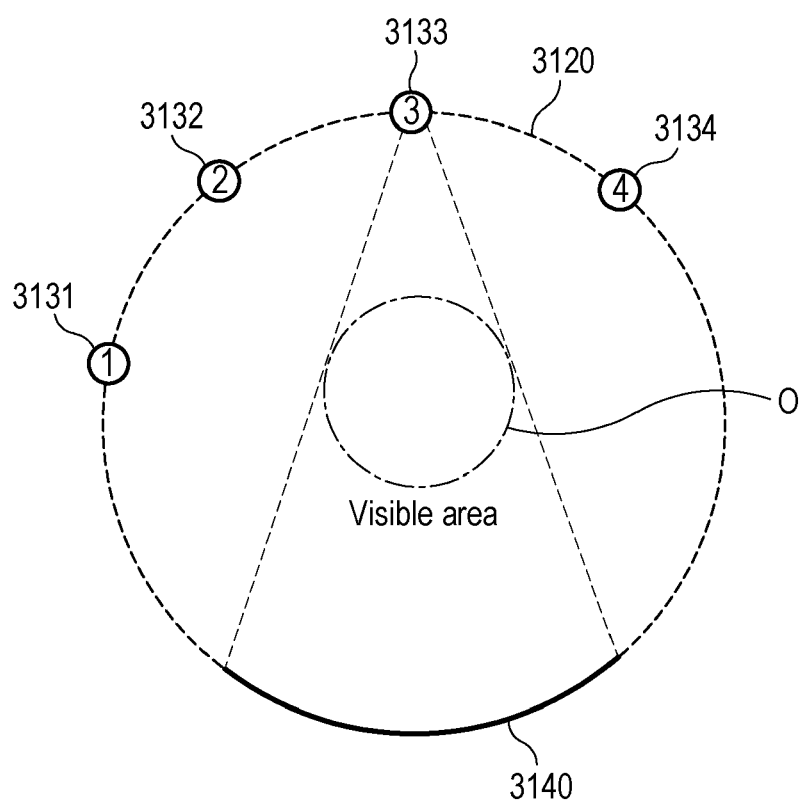
FIGS. 31A and 31B are diagrams illustrating a method of adjusting a visible area of a CT apparatus.
Figure 31B:
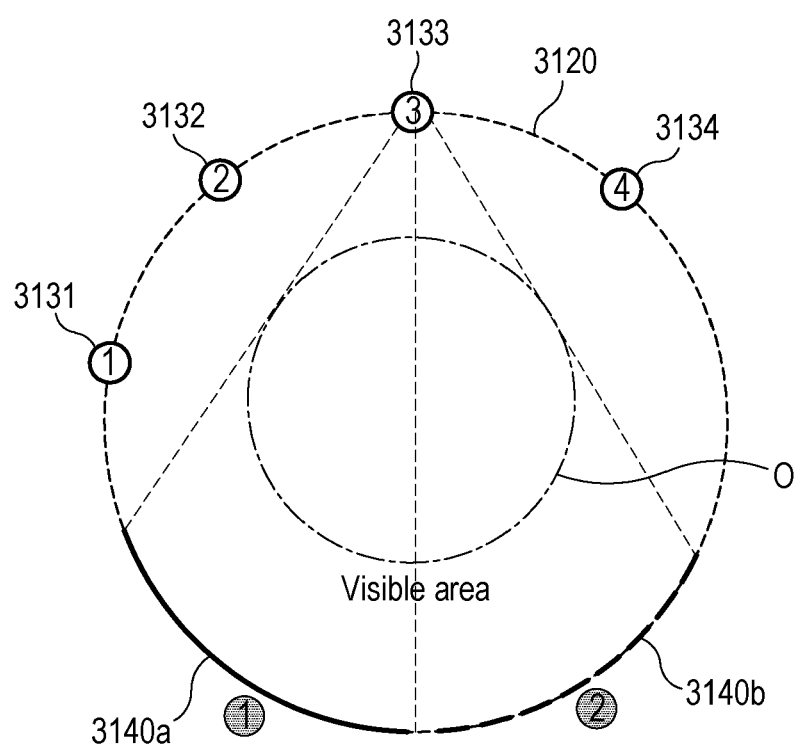
Figure 32:
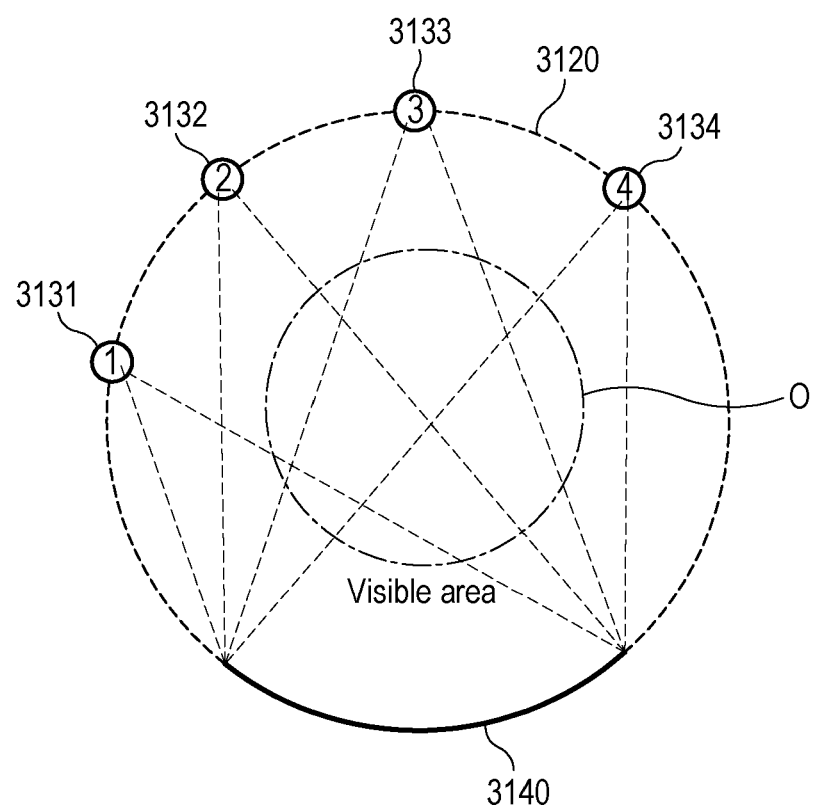
FIG. 32 is a diagram showing a method of adjusting a visible area using a plurality of light sources.

FIGS. 31A and 31B are diagrams illustrating a method of adjusting a visible area of a CT apparatus 100. FIG. 32 is a diagram showing a method of adjusting a visible area using a plurality of light sources. The visible area may be an area in which X-rays passing through a subject O may be detected.

Generally, referring to FIG. 31A, in the CT apparatus 100 according to various embodiments, a visible area may be determined by a cone beam angle of a light source 3133 that is currently being operated among a plurality of light sources 3131, 3132, 3133 and 3134. When a subject O is within a cone beam angle of a light source, the visible area may be determined by the angle of emission. In this case, a detector 3140 may be located in the visible area to detect X-rays passing through the subject O. For example, when the CT apparatus 100 may reduce the visible area to obtain a CT image of the subject O in a narrow area.

Referring to FIG. 31B, in order to obtain a CT image of a subject O in a wide area, a visible area may be set to be wider than a cone beam angle of a light source. In this case, X-rays passing through the subject O may be detected while moving the detector 3140 from a first position 3140a to a second position 3140b. In this case, X-rays need not necessarily be emitted a plurality of times to obtain a CT image of the subject and the amount of X-rays exposed to the subject may decrease.

Referring to FIG. 32, a CT apparatus 100 according to various embodiments may operate all of a plurality of light sources 3131, 3132, 3133 and 3134 to adjust a visible area even when some of the plurality of light sources 3131, 3132, 3133 and 3134 are not located at positions facing the detector 3140. In this case, a CT image of a subject O may be obtained without moving the detector 3140.

Figure 33:
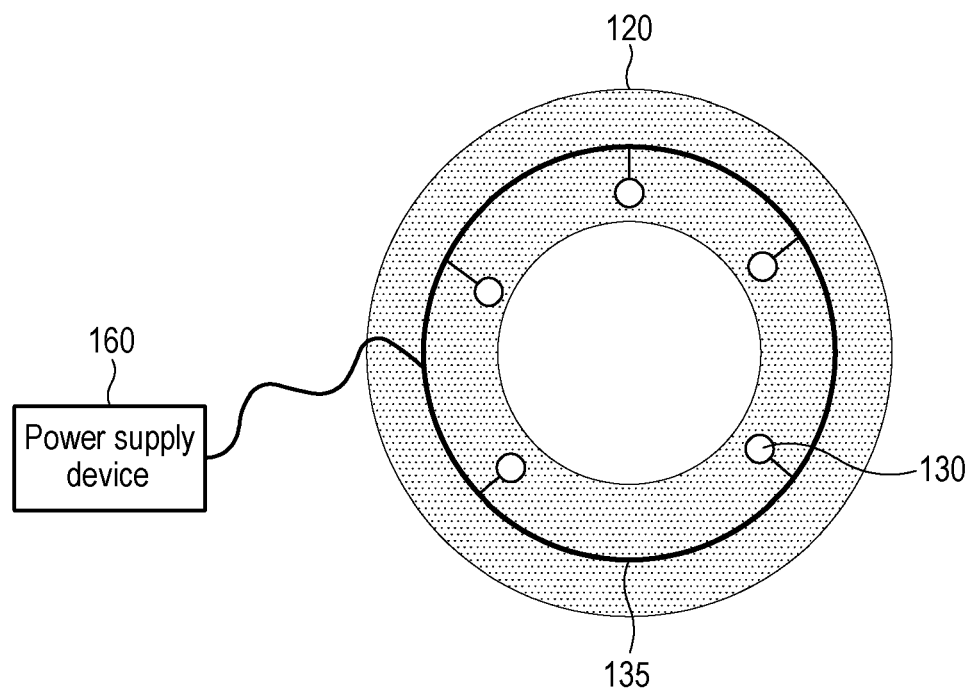
FIG. 33 is a diagram illustrating a CT apparatus according to various embodiments.

FIG. 33 is a diagram illustrating a CT apparatus 100 according to various embodiments of the present embodiment.

A power supply device 160 of the CT apparatus 100 according to various embodiments may be located outside a gantry 120. When the power supply device 160 is located outside the gantry 120, stability may be increased because the power supply device 160 does not rotate even when the gantry 120 is rotated. The power supply device 160 may be connected to a plurality of light sources 130 through cables. The cable may be formed of a flexible material. The plurality of light sources 130 may be supplied with power from the power supply device 160 through a metal part 135, and the vicinity of the metal part 135 may be molded by an insulating material to increase stability. The insulating material may be, for example, insulating oil or silicone.

FIGS. 34A to 35B are diagrams illustrating a CT apparatus 100 according to various embodiments of the present embodiment.

Figure 34A:
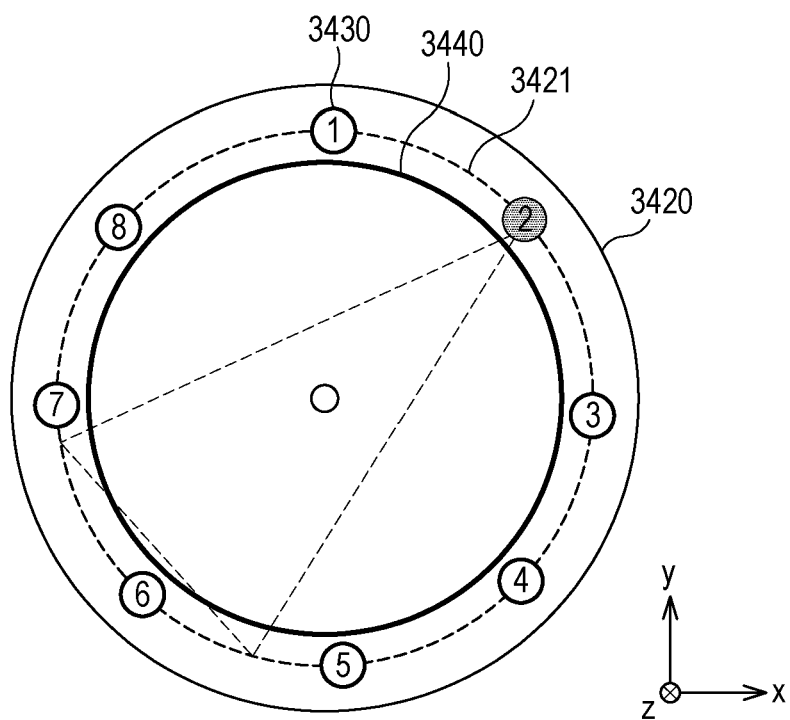
FIG. 34A is a cross-sectional view of an x-y plane of a gantry of a CT apparatus according to various embodiments.
Figure 34B:
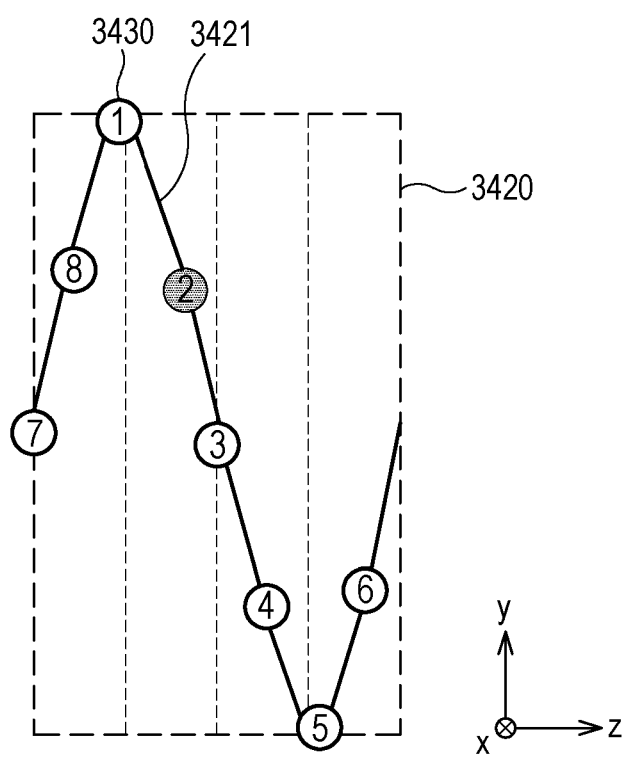
FIG. 34B is a schematic cross-sectional view of a y-z plane of the gantry.

FIG. 34A is a cross-sectional view of an x-y plane of a gantry 3420 of the CT apparatus 100 according to various embodiments, and FIG. 34B is a schematic cross-sectional view of a y-z plane of the gantry 3420.

The CT apparatus 100 according to various embodiments may include a gantry 3420 including a first rotation device 3421 and a second rotation device. A plurality of light sources 3430 may be arranged at regular intervals on the first rotation device 3421. A detector 3440 may be disposed on the second rotation device and configured to surround the second rotation device. In this drawing, it is described that the total number of the plurality of light sources 3430 is eight but the total number of the plurality of light sources 3430 is not limited to eight. When the total number of the plurality of light sources 3430 is eight, the plurality of light sources 3430 may be arranged on the first rotation device 3421 at intervals of 45 degrees.

Figure 35A:
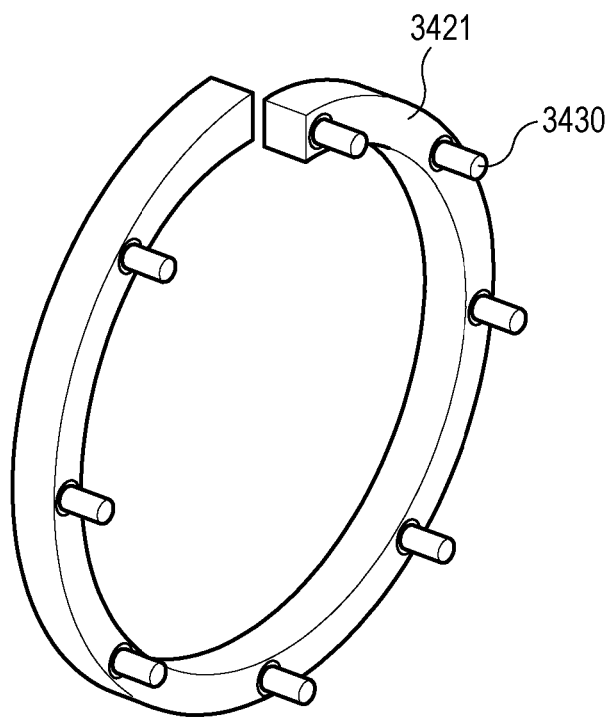
FIG. 35A is a cross-sectional view of an x-y plane of a gantry of a CT apparatus according to various embodiments.
Figure 35B:
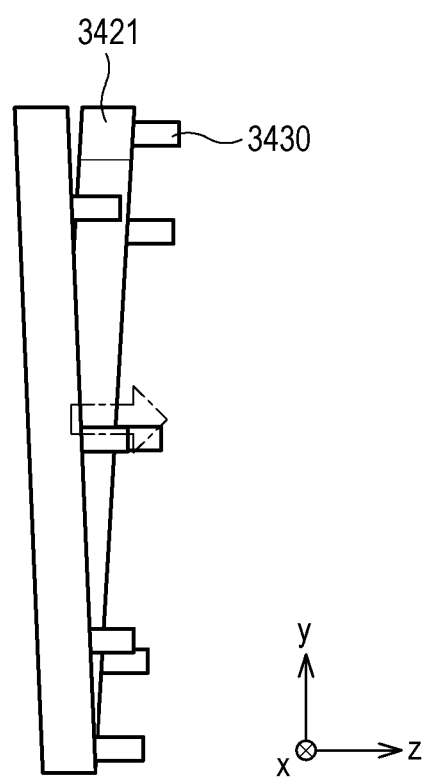
FIG. 35B is a schematic cross-sectional view of a y-z plane of the gantry.

According to various embodiments, positions of the plurality of light sources 3430 on a z-axis may be different from each other. For example, the plurality of light sources 3430 may be arranged as shown in FIG. 34B. As shown in FIGS. 35A and 35B, a structure of the first rotation device 3421 on which the plurality of light sources 3430 are arranged may be changed by applying a force to the first rotation device 3421 in a z-axis direction. When the first rotation device 3421 having the structure shown in FIGS. 35A and 35B is used, the CT apparatus 100 may obtain a helical CT image of a subject.

Although operations of processes, operations of methods, algorithms or the like of flowcharts are described herein in a sequential order, the processes, the methods, the algorithms or the like may be configured to be performed in any appropriate order. In other words, the processes, methods, and algorithms described above in the various embodiments of the present disclosure need not necessarily be performed in the orders described herein. Although some operations are described as being performed asynchronously, the operations may be performed simultaneously in other embodiments. In addition, it should not be understood that examples of a process illustrated in the drawings exclude other changes and modifications, any of the illustrated process or operations thereof are indispensable to at least one of various embodiments of the present disclosure, and the illustrated process is desirable.

While the foregoing methods have been described with respect to particular embodiments, these methods may also be implemented as computer-readable codes on a computer-readable recording medium. The computer-readable recording medium includes any kind of data storage devices that can be read by a computer system. Examples of the computer-readable recording medium include a read-only memory (ROM), a random-access memory (RAM), a compact disc (CD)-ROM, a magnetic tape, a floppy disk, an optical data storage device, and the like. The computer-readable recoding medium can be distributed to the computer systems connected through a network so that the computer-readable codes can be stored and executed in a distribution manner. Functional programs, codes, and code segments for implementing the foregoing embodiments can easily be inferred by programmers in the art to which the present disclosure pertains.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that such substitutions, modifications and changes are intended to fall within the scope of the appended claims.

What is claimed is:

1. A computed tomography (CT) apparatus comprising:
   a gantry including a first rotation device, a second rotation device, and a third rotation device which have a ring shape, share an axis of rotation, and are rotatable independently of one another;
   a plurality of first light sources provided on the first rotation device at regular intervals and configured to emit X-rays to a subject;
   a plurality of second light sources provided on the second rotation device at regular intervals and configured to emit X-rays to the subject;
   a detector provided on a region of the third rotation device and configured to detect X-rays passing through the subject; and
   one or more processors,
   wherein the one or more processors are configured to:
   control the first rotation device to repeatedly perform a first operation of being rotated in a first rotation direction by an angle of rotation determined based on a total number of the plurality of first light sources and a total number of the plurality of second light sources and a second operation of being rotated by the determined angle of rotation in a second rotation direction opposite to the first rotation direction;
   control the second rotation device to repeatedly perform a third operation of being rotated by the determined angle of rotation in the second rotation direction and a fourth operation of being rotated by the determined angle of rotation in the first rotation direction;
   control the third rotation device to be rotated in the first rotation direction at a same speed of rotation as the first rotation device and the second rotation device while the first rotation device repeatedly performs the first operation and the second operation and the second rotation device repeatedly performs the third operation and the fourth operation;
   emit X-rays to the subject from one of the plurality of first light sources during the performance of the first operation by the first rotation device and emit X-rays to the subject from one of the plurality of second light sources during the performance of the fourth operation by the second rotation device; and
   detect X-rays passing through the subject by the detector.

2. The CT apparatus of claim 1, wherein the first operation and the third operation are performed simultaneously, and the second operation and the fourth operation are performed simultaneously.

3. The CT apparatus of claim 1, wherein the one or more processors are configured to change a light source that emits X-rays among the plurality of first light sources and the plurality of second light sources based on a predetermined order, and
   wherein a number of times the first rotation device repeatedly performs the first operation and the second operation and a number of times the second rotation device repeatedly performs third operation and the fourth operation are determined based on the total number of the plurality of first light sources and the total number of the plurality of second light sources.

4. The CT apparatus of claim 3, wherein, when X-rays are set to be emitted starting from a light source among the plurality of first light sources and the plurality of second light sources based on the predetermined order at an initial stage, the one or more processors are configured to control an initial position of the third rotation device to cause the detector to be located at a position facing and corresponding to the light source.

5. The CT apparatus of claim 1, wherein the one or more processors are configured to:

create at least one raw image of the subject in response to the detection of the X-rays passing through the subject by the detector; and create a three-dimensional (3D) image of the subject based on the at least one raw image of the subject.

6. The CT apparatus of claim 1, further comprising a table on which the subject is loaded, wherein the one or more processors are configured to move the table at a predetermined speed in a direction of an axis of rotation.

7. The CT apparatus of claim 1, wherein the determined angle of rotation is a value obtained by dividing 360 degrees by the total number of the plurality of first light sources and the total number of the plurality of second light sources.

8. The CT apparatus of claim 1, wherein the plurality of first light sources and the plurality of second light sources comprise X-ray sources using carbon nanotubes.

9. The CT apparatus of claim 1, wherein a layout plan of the first rotation device, a layout plan of the second rotation device, and a layout plan of the third rotation device, which are perpendicular to the axis of rotation, are parallel to one another.

10. The CT apparatus of claim 1, further comprising a power supply device configured to supply a high voltage to the plurality of first light sources and the plurality of second light sources, wherein the power supply device is provided outside the gantry.

11. A computed tomography (CT) method performed by a CT apparatus including a gantry with a first rotation device, a second rotation device, and a third rotation device that have a ring shape, share an axis of rotation, and are rotatable independently of one another, a plurality of first light sources arranged on the first rotation device at regular intervals and configured to emit X-rays to a subject, a plurality of second light sources arranged on the second rotation device at regular intervals and configured to emit X-rays to the subject, and a detector provided on a region of the third rotation device and configured to detect X-rays passing through the subject, the CT method comprising:

controlling the first rotation device to repeatedly perform a first operation of being rotated in a first rotation direction by an angle of rotation determined based on a total number of the plurality of first light sources and a total number of the plurality of second light sources and a second operation of being rotated by the determined angle of rotation in a second rotation direction opposite to the first rotation direction;

controlling the second rotation device to repeatedly perform a third operation of being rotated by the determined angle of rotation in the second rotation direction and a fourth operation of being rotated by the determined angle of rotation in the first rotation direction;

controlling the third rotation device to be rotated in the first rotation direction at the same speed of rotation as the first rotation device and the second rotation device;

emitting X-rays to the subject from one of the plurality of first light sources during the performance of the first operation by the first rotation device and emitting X-rays to the subject from one of the plurality of second light sources during the performance of the fourth operation by the second rotation device; and detecting X-rays passing through the subject by the detector.

12. The CT method of claim 11, wherein the first operation and the third operation are performed simultaneously, and the second operation and the fourth operation are performed simultaneously.

13. The CT method of claim 11, further comprising changing a light source that emits X-rays among the plurality of first light sources and the plurality of second light sources based on a predetermined order, wherein a number of times the first rotation device repeatedly performs the first operation and the second operation and a number of times the second rotation device repeatedly performs the third operation and the fourth operation are determined based on the total number of the plurality of first light sources and the total number of the plurality of second light sources.

14. The CT method of claim 13, when X-rays are set to be emitted starting from a light source among the plurality of first light sources and the plurality of second light sources based on the predetermined order at an initial stage, the CT method further comprising controlling an initial position of the third rotation device to cause the detector to be located at a position facing and corresponding to the light source.

15. The CT method of claim 11, further comprising:

creating at least one raw image of the subject in response to the detection of the X-rays passing through the subject by the detector; and creating a three-dimensional (3D) image of the subject based on the at least one raw image of the subject.

16. The CT method of claim 11, further comprising moving a table, on which the subject is loaded, at a predetermined speed in a direction of an axis of rotation.

17. The CT method of claim 11, wherein the determined angle of rotation is a value obtained by dividing 360 degrees by the total number of the plurality of first light sources and the total number of the plurality of second light sources.

18. The CT method of claim 11, wherein the plurality of first light sources and the plurality of second light sources comprise X-ray sources using carbon nanotubes.

19. The CT method of claim 11, wherein a layout plan of the first rotation device, a layout plan of the second rotation device, and a layout plan of the third rotation device, which are perpendicular to the axis of rotation, are parallel to one another.

20. The CT method of claim 11, wherein a power supply configured to supply a high voltage to the plurality of first light sources and the plurality of second light sources is provided outside the gantry.

* * * * *